United States Patent [19]

Philion

[11] Patent Number: 4,751,246

[45] Date of Patent: Jun. 14, 1988

[54] COMPOSITIONS AND METHOD

[75] Inventor: Richard E. Philion, Sand Lake, N.Y.

[73] Assignee: Sterling Drug Inc., New York, N.Y.

[21] Appl. No.: 402,732

[22] Filed: Jul. 28, 1982

Related U.S. Application Data

[60] Division of Ser. No. 937,928, Aug. 30, 1978, Pat. No. 4,374,149, which is a continuation-in-part of Ser. No. 803,372, Jun. 3, 1977, abandoned, which is a continuation-in-part of Ser. No. 699,856, Jun. 25, 1976, abandoned.

[51] Int. Cl.$^4$ ............................................. A61K 31/135
[52] U.S. Cl. .................................................. 514/649
[58] Field of Search ............................. 564/344, 342; 260/456 P, 457, 501.18, 508; 424/383, 389, 311, 316, 320; 560/110, 142

[56] References Cited

U.S. PATENT DOCUMENTS

| | | | |
|---|---|---|---|
| 2,431,285 | 11/1946 | Sater et al. | 564/343 X |
| 3,816,516 | 6/1974 | Cox et al. | 564/344 X |
| 3,917,704 | 11/1975 | Kaiser et al. | 260/570.6 |
| 3,954,871 | 5/1976 | Buu-Hoi et al. | 260/570.6 |
| 4,048,229 | 9/1977 | Colella et al. | 564/344 X |

OTHER PUBLICATIONS

Kaiser et al., Abstracts of Papers, ACS Meeting 169: Medi 54 (Apr. 1975).

*Primary Examiner*—Robert V. Hines
*Attorney, Agent, or Firm*—Paul E. Dupont

[57] ABSTRACT

Alpha-(aminoalkyl)-4-hydroxy-3-(alkylsulfinyl)benzenemethanols and 2-[4-hydroxy-3-(alkylsulfinyl)phenyl]ethylamines useful as antihypertensive agents are prepared by oxidation of the corresponding alpha-(aminoalkyl)-4-hydroxy-3-(alkylthio)benzenemethanols and 2-[4-hydroxy-3-(alkylthio)phenyl]ethylamines respectively.

19 Claims, No Drawings

COMPOSITIONS AND METHOD

CROSS-REFERENCE TO RELATED APPLICATIONS

This application is a division of copending application Ser. No. 937,928, filed Aug. 30, 1978 and now U.S. Pat. No. 4,374,149, which is a continuation-in-part of application Ser. No. 803,372, filed June 3, 1977, now abandoned, which is in turn a continuation-in-part of application Ser. No. 699,856 filed June 25, 1976, now abandoned.

BACKGROUND OF THE INVENTION

1. Field of the Invention

The present invention relates to compositions of matter classified in the art of chemistry as α-(aminoalkyl)-4-hydroxy-3-(alkylsulfinyl)benzenemethanols and 2-[4-hydroxy-3-(alkylsulfinyl)phenyl]ethylamines, to processes and intermediates for the preparation thereof, and to a method of using the same for reducing blood pressure in mammals.

2. Prior Art

Continental Pharma British Specification No. 1,321,701, published June 27, 1973, discloses a group of compounds embraced by the generic formula

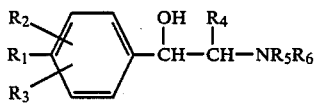

wherein, inter alia:

$R_1$ is RS, RSO or $RSO_2$(R=H, or $C_1$-$C_{10}$ alkyl);

$R_2$ and $R_3$ are hydrogen, $C_1$-$C_4$ alkoxy or $C_1$-$C_4$ alkylthio;

$R_4$ is hydrogen or $C_1$-$C_4$ alkyl; and $R_5$ and $R_6$ are independently hydrogen or $C_1$-$C_{16}$ alkyl optionally substituted by a phenyl or substituted phenyl group. The compounds are stated to exhibit β-adrenergic blocking, peripheral vasodilator, antiarrhythmic and hypotensive activities.

In the field of antihypertensive therapy the use of peripheral vasodilator agents to lower blood pressure has often suffered a serious disadvantage, namely, the reflex tachycardia elicited by the hypotension induced by systemic vasodilation. Recently efforts have been made to overcome this problem by employing hypotensive vasodilators in combination with β-adrenergic blocking agents, the function of the latter being to reduce the reflex tachycardia caused by the vasodilator-induced hypotension. This mode of therapy of course suffers the inconvenience of requiring two separate drugs and the attendant need for separate dosage regulation as well as the increased potential for patient error in failing to administer either one or the other of the drugs.

SUMMARY OF THE INVENTION

The present invention provides novel, therapeutically useful compounds which have both hypotensive vasodilator and β-adrenergic blocking activity and which are therefore indicated for use as antihypertensive agents free of the undesirable tachycardic side effects associated with currently used vasodilator agents. Certain of the compounds also exhibit antiarrhythmic activity.

In a composition of matter aspect the invention relates to α-{[(arylakyl)amino]alkyl}-4-YO-3-(lower alkylsulfinyl)benzenemethanols which are useful as antihypertensive agents. Some species are also useful as antiarrhythmic agents.

In another composition of matter aspect the present invention provides [(arylalkyl)amino]alkyl 4-YO-3-(lower alkylsulfinyl)phenyl ketones which are useful as antihypertensive agents and as intermediates in the preparation of the corresponding benzenemethanols. Certain of the ketones are also useful as antiarrhythmic agents.

In a further composition of matter aspect this invention relates to N-(arylalkyl)-2-[4-YO-3-(lower alkylsulfinyl)phenyl]ethylamines which are useful as antihypertensive agents. Some species are also useful as antiarrhythmic agents.

In yet another composition aspect the present invention provides a pharmaceutical composition comprising an α-{[(arylalkyl)amino]alkyl}-4-YO-3-(lower alkylsulfinyl)benzenemethanol in admixture with a pharmaceutically acceptable excipient.

In a further composition aspect this invention relates to a pharmaceutical composition comprising an [(arylalkyl)amino]alkyl 4-YO-3-(lower alkylsulfinyl)phenyl ketone in admixture with a pharmaceutically acceptable excipient.

In another composition aspect this invention provides a pharmaceutical composition comprising an N-(arylalkyl)-2-[4-YO-3-(lower alkylsulfinyl)phenyl]ethylamine in admixture with a pharmaceutically acceptable excipient.

In one of its process aspect this invention relates to a process for preparing α-{[(arylalkyl)amino]alkyl}-4-YO-3-(lower alkylsulfinyl)benzenemethanols which comprises oxidizing the corresponding α-{[(arylalkyl)amino]alkyl}-4-YO-3-(lower alkylthio)benzenemethanols.

In a further process aspect this invention provides a process for preparing [(arylalkyl)amino]alkyl 4-YO-3-(lower alkylsulfinyl)phenyl ketones which comprises oxidizing the corresponding [(arylalkyl)amino]alkyl 4-YO-3-(lower alkylthio)phenyl ketones.

In yet another process aspect the present invention relates to a process for preparing N-(arylalkyl)-2-[4-YO-3-(lower alkylsulfinyl)phenyl]ethylamines which comprises oxidizing the corresponding N-(arylalkyl)-2-[4-YO-3-lower alkylthio)phenyl]ethylamines.

In a method aspect the present invention provides a method of reducing blood pressure in mammals which comprises administering to said mammals a blood pressure lowering effective amount of an α-{[(arylalkyl)amino]alkyl}-4-YO-3-(lower alkylsulfinyl)benzenemethanol of the invention.

In another method aspect this invention relates to a method of producing vasodilation in mammals which comprises administering to said mammals, in an amount effective to produce vasodilation, an α-{[(arylalkyl)amino]alkyl}-4-YO-3-(lower alkylsulfinyl)benzenemethanol of the invention.

In another method aspect the present invention pertains to a method of reducing blood pressure in mammals which comprises administering to said mammals a blood pressure lowering effective amount of an [(arylalkyl)amino]alkyl 4-YO-3-(lower alkylsulfinyl)phenyl ketone of the invention.

In yet a further method aspect the invention provides a method of reducing blood pressure in mammals which comprises administering to said mammals a blood pressure lowering effective amount of an N-(arylalkyl)-2-[4-YO-3-(lower alkylsulfinyl)phenyl]ethylamine of the invention.

DETAILED DESCRIPTION INCLUSIVE OF THE PREFERRED EMBODIMENTS

More specifically the invention sought to be patented resides, in a composition of matter aspect, in α-{[(arylalkyl)amino]alkyl}-4-YO-3-(lower alkylsulfinyl)-benzenemethanols which are useful as antihypertensive agents having Formula I hereinbelow:

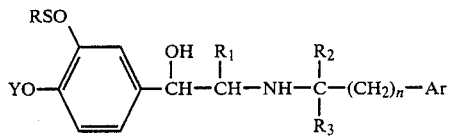

wherein:

$R_1$, $R_2$ and $R_3$ are independently hydrogen or lower alkyl;

n is an integer from 1 to 3;

Ar is phenyl, methylenedioxyphenyl or phenyl having from one to three substituents selected from the group consisting of halo, lower alkyl, hydroxy and lower alkoxy;

R is lower alkyl;

Y is hydrogen, lower alkyl, lower alkoxy-lower alkyl, lower alkanoyl, aroyl, benzenesulfonyl or toluenesulfonyl; and acid-addition salts thereof.

As described more fully hereinbelow certain of these compounds are also useful as antiarrhythmic agents.

In a further composition of matter aspect the invention sought to be patented resides in [(arylalkyl)amino]alkyl 4-YO-3-(lower alkylsulfinyl)phenyl ketones having Formula II hereinbelow:

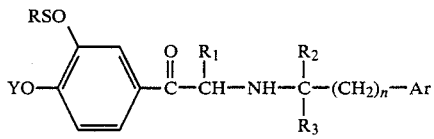

wherein $R_1$, $R_2$, $R_3$, n, Ar, R and Y have the above-given meanings; and acid-addition salts thereof.

These compounds are useful as antihypertensive agents and as intermediates in the preparation of the corresponding benzenemethanols of Formula I hereinabove. As described more fully hereinbelow, certain of the ketones are also useful as antiarrhythmic agents.

Among the foregoing composition aspects, particular embodiments sought to be patented reside in the compounds of Formulas I and II hereinabove wherein $R_1$, $R_2$, $R_3$, n, R and Y have the previously indicated meanings and Ar is phenyl or phenyl having one or two substituents selected from the group consisting of lower alkyl, hydroxy and lower alkoxy.

In another composition of matter aspect the invention sought to be patented resides in N-(arylalkyl)-2-[4-YO-3-(lower alkylsulfinyl)phenyl]ethylamines having Formula III hereinbelow:

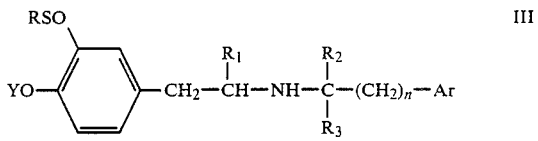

wherein $R_1$, $R_2$, $R_3$, n, Ar, R and Y have the previously indicated meanings; and acid-addition salts thereof.

These compounds are useful as antihypertensive agents and as more fully described hereinbelow, certain of them are also useful as antiarrhythmic agents.

In a further composition aspect the invention sought to be patented resides in a pharmaceutical composition comprising a compound of Formula I hereinabove in admixture with a pharmaceutically acceptable excipient.

In yet another composition of matter aspect the invention sought to be patented resides in a pharmaceutical composition comprising a compound having Formula II hereinabove in admixture with a pharmaceutically acceptable excipient.

The invention sought to be patented resides in a further composition aspect in a pharmaceutical composition comprising a compound having Formula III hereinabove in admixture with a pharmaceutically acceptable excipient.

In one of its process aspects the invention sought to be patented resides in the process for producing the 3-(lower alkylsulfinyl)benzenemethanols of Formula I hereinabove which comprises oxidizing the corresponding 3-(lower alkylthio)benzenemethanols of Formula IV hereinbelow:

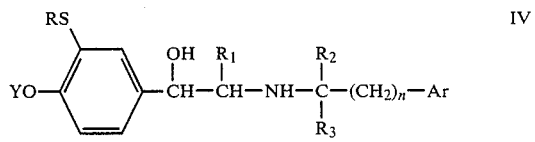

wherein $R_1$, $R_2$, $R_3$, n, Ar, R and Y have the above-given meanings, and acid-addition salts thereof.

In a further process aspect the invention sought to be patented resides in the process for producing the aminoalkyl 3-(lower alkylsulfinyl)phenyl ketones of Formula II hereinabove which comprises oxidizing the corresponding aminoalkyl 3-(lower alkylthio)phenyl ketones of Formula V hereinbelow:

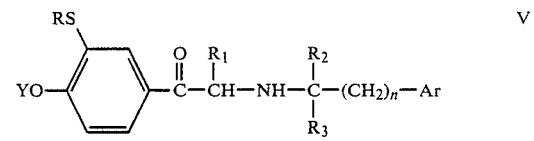

wherein $R_1$, $R_2$, $R_3$, n, Ar, R and Y have the above-given meanings, and acid-addition salts thereof.

In yet a further process aspect the invention sought to be patented resides in the process for producing the 2-[3-(lower alkylsulfinyl)phenyl]ethylamines of Formula III hereinabove which comprises oxidizing the corresponding 2-[3-(lower alkylthio)phenyl]ethylamines of Formula VI hereinbelow:

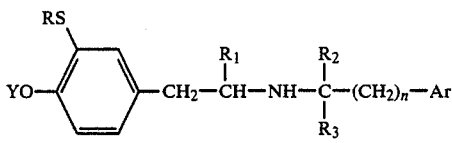

VI wherein $R_1$, $R_2$, $R_3$, n, Ar, R and Y have the above-given meanings, and acid-addition salts thereof.

In a method aspect the invention sought to be patented resides in the method of reducing blood pressure in mammals which comprises administering to said mammals a blood pressure lowering effective amount of a compound of Formula I hereinabove.

In another method aspect the invention sought to be patented resides in the method of producing vasodilation in mammals which comprises administering to said mammals, in an amount effective to produce vasodilation, a compound of Formula I hereinabove.

In yet another method aspect the invention sought to be patented resides in the method of reducing blood pressure in mammals which comprises administering to said mammals a blood pressure lowering effective amount of a compound of Formula II hereinabove.

In a further method aspect the invention sought to be patented resides in the method of reducing blood pressure in mammals which comprises administering to said mammals a blood pressure lowering effective amount of a compound of Formula III hereinabove.

In the terms lower alkyl, lower alkoxy, lower alkylthio and lower alkylsulfinyl, "lower" denotes an alkyl moiety having from 1 to 4 carbon atoms which can be arranged as straight or branched chains. There are included methyl, ethyl, n-propyl, isopropyl, n-butyl, sec-butyl, and the like, methyl and ethyl being preferred.

By "lower alkanoyl" is meant straight or branched chain alkanoyl radicals containing from 1 to 6 carbon atoms as illustrated by formyl, acetyl, propionyl, butyryl, isobutyryl, pivalyl, caproyl and the like.

The term "halo" as used herein denotes fluoro, chloro, bromo or iodo.

The term "aroyl" as used herein is intended to include benzoyl and benzoyl substituted by from one to two lower alkyl groups, for example: o-toluyl, m-toluyl, p-toluyl, 3,4-dimethylbenzoyl, 3,5-dimethylbenzoyl, 2,5-dimethylbenzoyl, m-isopropylbenzoyl, p-tert-butylbenzoyl and the like.

It will be appreciated that Y in Formulas I, II and III can represent acyl residues other than the above without departing from the spirit of the present invention since it is well known that such esters undergo hydrolytic cleavage under physiological conditions to produce in situ the parent phenols which, of course, have the previously indicated biological activity.

As used herein "toluenesulfonyl" is intended to include ortho, metal and para-toluenesulfonyl.

In accordance with one of the process aspects of the invention the 3-(lower alkylsulfinyl)benzenemethanols represented by Formula I hereinabove are obtained by oxidizing the corresponding 3-(lower alkylthio)benzenemethanols of Formula IV hereinabove with an appropriate oxidizing agent such as a peracid, hydrogen peroxide or sodium metaperiodate.

The oxidation is preferably carried out by treating the 3-(lower alkylthio)benzenemethanol with commercial 50% peracetic acid in methanol at about $-10°$ C. to $10°$ C. for approximately 15 minutes to 1.5 hours or until oxidation is substantially complete as indicated by thin layer chromotography.

Alternatively, oxidation is affected with 30% hydrogen peroxide in methanol at about 20° C. to 65° C. for from 24 to 72 hours or until oxidation is substantially complete as indicated by thin layer chromotography. The oxidation product is isolated according to conventional methods.

While it is ordinarily preferred to prepare the 3-(lower alkylsulfinyl)benzenemethanols of Formula I by the above-described oxidation procedures, these compounds can also be prepared by reducing the corresponding aminoalkyl 3-(lower alkylsulfinyl)phenyl ketones of Formula II hereinabove in accordance with the procedures described hereinbelow for the preparation of the intermediate 3-(lower alkylthio)benzenemethanols of Formula IV.

The 3-(lower alkylthio)benzenemethanols of Formula IV hereinabove are obtained by reducing the aminoalkyl 3-(lower alkylthio)phenyl ketones of Formula V with an appropriate reducing agent in a suitable solvent as for example sodium borohydride or lithium borohydride in water or a lower alkanol; lithium aluminum hydride in ether, tetrahydrofuran or dioxane; diborane in tetrahydrofuran or diglyme; aluminum isopropoxide in 2-propanol; or by hydrogenation in the presence of a noble metal catalyst such as palladium or platinum.

When the aminoalkyl 3-(lower alkylthio)phenyl ketone contains a carboxylic ester group (Formula V wherein Y is lower alkanoyl or aroyl), and it is desired to retain the ester group in the reduction product (Formula IV wherein Y is lower alkanoyl or aroyl), the use of reducing means resulting in reduction of carboxylic ester groups should of course be avoided. Accordingly, in such instances reduction is preferably effected with an alkali metal borohydride or by catalytic hydrogenation which reducing means result in selective reduction of the ketone function. When the ultimately desired product is the free phenol (Formula IV wherein Y is hydrogen) the above reduction reaction can be followed by hydrolysis of the ester group, or alternatively, the esterified aminoalkyl 3-(lower alkylthio)phenyl ketone (Formula V wherein Y is lower alkanoyl or aroyl) can be reduced with a reagent capable of reducing both ketone and carboxylic ester functions e.g. lithium aluminum hydride.

The borohydride reduction method is conveniently carried out by treating the aminoalkyl 3-(lower alkylthio)phenyl ketone with sodium borohydride in methanol at about $-10°$ C. to 65° C. for approximately 15 minutes to 2.5 hours or until reduction is substantially complete as indicated by thin layer chromatography. If the starting material contains an ester group (Formula V wherein Y is lower alkanoyl or aroyl) and it is desired to retain the latter in the final product, the reaction mixture is quenched with acid and the esterfied benzenemethanol (Formula IV wherein Y is lower alkanoyl or aroyl) is isolated in conventional fashion. If on the other hand the free phenol (Formula IV wherein Y is hydrogen) is desired the reaction mixture is treated with an equivalent of sodium or potassium hydroxide in water and stirred at about 20° C. to 65° C. for approximately 30 minutes to 15 hours. The resulting phenol is isolated in a conventional manner.

The catalytic hydrogenation process is conveniently carried out in a suitable solvent, for example N,N-dimethylformamide, at 20° C. to 50° C. under a hydrogen pressure of from 20–50 p.s.i. in the presence of a noble metal catalyst such as palladium. The hydrogenation is continued until the theoretical amount of hydrogen is absorbed. After removal of the catalyst, the reduction product is isolated in conventional fashion.

The aminoalkyl 3-(lower alkylsulfinyl)phenyl ketones of Formula II hereinabove are obtained in accordance with this invention by oxidation of the corresponding aminoalkyl 3-(lower alkylthio)phenyl ketones of Formula V as described hereinabove for the preparation of the 3-(lower alkylsulfinyl)benzenemethanols of Formula I.

The aminoalkyl 3-(lower alkylthio)phenyl ketones of Formula V hereinabove are obtained by reacting a haloketone of Formula VII hereinbelow

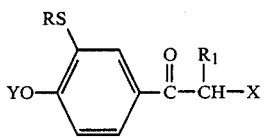

VII wherein $R_1$, Y and R have the previously given meanings and X is chloro, bromo or iodo with an excess of an (arylalkyl)amine of Formula VIII hereinbelow:

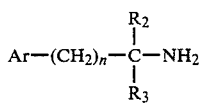

VIII wherein $R_2$, $R_3$, n and Ar have the previously given meanings in a suitable solvent such as acetonitrile, dimethylsulfoxide or N,N-dimethylformamide at about $-65°$ C. to $25°$ C. for from 1 to 4 hours or until the reaction is substantially complete as indicated by thin layer chromatography.

In those instances wherein Y in Formula VII is lower alkanoyl or aroyl reaction with an arylalkyl amine may result in partial cleavage of the ester function. When desired the partially deacylated product can be reesterified according to known procedures, for example, with an acyl halide in the presence of a strong acid such as trifluoroacetic acid.

The (arylalkyl)amines of Formula VIII are generally known, or if specifically new are obtained according to the procedures described for the preparation of the known compounds.

Thus for example tertiary carbinamines, i.e., (arylalkyl)amines of Formula VIII wherein both $R_2$ and $R_3$ are lower alkyl can be obtained from the corresponding generally known tertiary carbinols via the well known Ritter reaction [Organic Reactions 17, 213 (1969)] followed by hydrolysis of the resulting tertiary carbinamides.

(Arylalkyl)amines of Formula VIII wherein one of or both $R_2$ and $R_3$ are hydrogen can be obtained by reaction of an aldehyde or ketone of appropriate carbon content with ammonia or an ammonia derivative in accordance with the procedures described in Organic Reactions 4, 174 (1948) and Organic Reactions 5, 301 (1949).

The haloketones of Formula VII are obtained by halogenating with chlorine or bromine the appropriate phenyl ketone having the Formula IX hereinbelow:

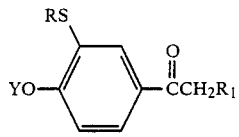

IX wherein R and $R_1$ have the previously given meanings and Y is lower alkyl, lower alkoxy-lower alkyl, lower alkanoyl, aroyl, benzenesulfonyl or toluenesulfonyl. The reaction is conveniently carried out by treating the ketone of Formula IX in an inert solvent such as chloroform with bromine at approximately $25°$ C. optionally in the presence of an inorganic base, e.g. calcium carbonate. The reaction generally has an induction period and in certain instances it may be advantageous to initiate the reaction by exposing the mixture to ultraviolet radiation until bromination has commenced as evidenced by decolorization and concomitant evolution of hydrogen bromide. If desired the Y substituent of the resulting haloketone can be removed according to well known procedures, for example by ester hydrolysis when Y is lower alkanoyl or aroyl and by O-demethylation with a Lewis acid such as aluminum chloride, hydrogen bromide or boron tribromide when Y is methyl.

The corresponding iodoketones (Formula VII wherein X is iodo) can be obtained by reacting the chloro or bromoketones with sodium or potassium iodide in acetone under the conditions of the well known Finkelstein reaction.

The phenyl ketones of Formula IX hereinabove can be obtained by a variety of procedures which are generally known in the art.

Thus for example the 3-(lower alkylthio)phenyl ketones of Formula IX wherein Y is lower alkanoyl or aroyl are obtained by alkylation of the parent 3-mercapto-4-hydroxyphenyl ketones (Formula IX wherein R and Y are hydrogen) with an appropriate lower alkyl halide in a suitable solvent such as a lower alkanone in the presence of an acid acceptor, e.g. an alkali metal carbonate, followed by esterification of the resulting 3-(lower alkylthio)-4-hydroxyphenyl ketones with an appropriate acylating agent such as a lower alkanoyl or aroyl halide or anhydride in an inert solvent such as methylene chloride, chloroform, benzene or toluene in the presence of an acid acceptor such as triethylamine or pyridine. The 3-mercapto-4-hydroxyphenyl ketones are in turn obtained by chlorosulfonation of the generally known alkyl 4-hydroxyphenyl ketones with excess chlorosulfonic acid at about $0°$ C. to $25°$ C. preferably in the absence of a solvent, followed by reduction of the resulting alkyl 3-chlorosulfonyl-4-hydroxyphenyl ketones with a suitable reducing agent such as stannous chloride and hydrochloric acid or zinc and sulfuric acid.

Alternatively the 3-(lower alkylthio)phenyl ketones of Formula IX can be obtained by acylating the generally known o-(lower alkylthio)phenols with an appropriate acyl halide (e.g. $R_1CH_2COCl$) under Friedel-Crafts conditions followed by esterification or alkylation of the resulting 3-(lower alkylthio)-4-hydroxyphenyl ketones.

The lower alkylsulfinyl-substituted 2-phenylethylamines of Formula III hereinabove are obtained in accordance with this invention by oxidizing the corresponding lower alkylthio-substituted 2-phenylethylamines of Formula VI as described hereinabove for the preparation of the 3-(lower alkylsulfinyl)benzenemethanols of Formula I.

The lower alkylthio-substituted 2-phenylethylamines of Formula VI hereinabove are obtained by reducing a 2-halo-2-phenylethylamine of Formula X hereinbelow

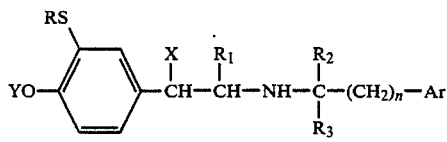

wherein $R_1$, $R_2$, $R_3$, n, Ar, R and Y have the previously indicated meanings and X is chloro, bromo or iodo with a suitable reducing agent such as lithium aluminum hydride in ether, tetrahydrofuran or dioxane, sodium borohydride in a lower alkanol or N,N-dimethylformamide or by catalytic hydrogenation.

Reduction is conveniently achieved employing sodium borohydride in N,N-dimethylformamide at $-10°$ C. to 25° C. for about 0.25 to 2 hours or until the reaction is substantially complete as indicated by thin layer chromatography.

Of course, when the 2-halo-2-phenylethylamine contains another reducible function such as an ester group (e.g. Formula X wherein Y is lower alkanoyl or aroyl) and it is desired to retain such function in the reduction product, the precautions described hereinabove for reducing the aminoalkyl 3-(lower alkylthio)phenyl ketones (Formula V) should be taken.

The 2-halo-2-phenylethylamines of Formula X hereinabove are obtained by reaction of an appropriate benzenemethanol of Formula IV with a halogen acid or an inorganic acid halide in a suitable solvent, e.g. hydrogen chloride in tetrahydrofuran or dioxane, hydrogen bromide in acetic acid, sodium or potassium iodide in phosphoric acid, thionyl chloride, thionyl bromide, phosphorus oxychloride, phosphorus oxybromide, phosphorus trichloride or phosphorus tribromide in benzene, toluene, chloroform or pyridine.

Due to the presence of the basic amino grouping, the free base forms of the products represented by Formulas I, II and III react with organic and inorganic acids to form acid-addition salts. The compounds of the invention are useful both in the free base form and in the form of acid-addition salts, and both forms are within the purview of the invention. The acid-addition salts are simply a more convenient form for use, and in practice, use of the salt form inherently amounts to use of the base form.

The acid-addition salts are prepared from any organic or inorganic acid. They are obtained in conventional fashion, for instance either by direct mixing of the base with the acid, or, when this is not appropriate, by dissolving either or both the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be any acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, dibenzoyltartaric acid, oxalic acid, pyromucic acid, citric acid, lactic acid, mandelic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, cyclohexylsulfamic acid, isethionic acid, methanesulfonic acid, benzenesulfonic acid, p-toluenesulfonic acid, 1,4-naphthalenedisulfonic acid, butylarsonic acid, methanephosphonic acid, acidic resins, hydrofluoric acid, hydrochloric acid, hydrobromic acid, hydriodic acid, perchloric acid, nitric acid, sulfuric acid, sulfamic acid, glutaric acid, phosphoric acid, arsenic acid, and the like.

All the acid-addition salts are useful as sources of the free base form, by reaction with an inorganic base. It will thus be appreciated that if one or more of the characteristics such as solubility, crystallinity, molecular weight, physical appearance, toxicity, or the like of a given base or acid-addition salt thereof render that form unsuitable for the purpose at hand it can be readily converted, in accordance with procedures well known in the art, to another more suitable form.

When the compounds of the invention are to be utilized for pharmaceutical purposes, the acids used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Appropriate medicinally acceptable salts within the scope of the invention are those derived from acids such as hydrochloric acid, acetic acid, lactic acid, tartaric acid, cyclohexylsulfamic acid, methanesulfonic acid, phosphoric acid and the like.

The compounds of the invention represented by Formulas I–III wherein Y is hydrogen are of course amphoteric, having both acidic phenol and basic amino groups, and thus form salts with both acids and bases.

Due to the presence of at least one and as many as four asymmetric centers in the compounds of the invention represented by Formula I (i.e. the carbinol carbon atom, the carbon atoms to which $R_1$, when lower-alkyl, is attached, the carbon atom to which $R_2$ and $R_3$, when dissimilar, are attached, and the sulfur atom), said compounds can exist in as many as 16 stereochemically isomeric forms, all of which either individually or as mixtures of any two or more are considered within the purview of this invention. If desired, the isolation or the production of a particular stereochemical form or of a mixture of two or more stereochemical forms can be accomplished by application of general principles known in the art.

Similarly, the aminoalkyl phenyl ketones of Formula II and the 2-phenylethylamines of Formula III each having three potential centers of asymmetry can exist in as many as eight stereochemically isomeric forms. All such forms, either individually or as mixtures of any two or more, are of course considered within the ambit of the present invention.

When preparing either a particular stereoisomer or a specific mixture of any two or more stereoisomers it is advantageous to employ intermediates of fixed stereochemical configuration thereby limiting the number of stereoisomeric forms present in the final product and thus simplifying isolation of the desired components. Accordingly, prior to reaction with a haloketone of Formula VII an (arylalkyl)amine of Formula VIII containing an asymmetric center (i.e. the carbon bearing nonidentical substituents $R_2$ and $R_3$) is resolved into its (+) and (−) optical antipodes according to conventional techniques and employing conventional resolving agents such as optically active tartaric acid, O,O-dibenzoyl tartaric acid, mandelic acid, malic acid, and the like. As desired, either the (+) or the (−)-(arylalkyl)amine can then be reacted with a haloketone according to the previously described procedure to produce an aminoalkyl phenyl ketone of Formula V having a fixed stereochemical configuration at the carbon bearing substituents $R_2$ and $R_3$.

When the haloketone also contains an asymmetric center (Formula VII wherein $R_1$ is lower alkyl) reaction with either the (+) or (−)-(arylalkyl)amine produces a pair of diastereomeric aminoalkyl phenyl ketones of Formula V ($R_1$ is lower alkyl) which can be separated according to conventional methods, e.g. fractional crystallization of a suitable acid addition salt.

Of course, when the haloketone contains no asymmetric center (Formula VII wherein $R_1$ is hydrogen) reaction with either the (+) or (−)-(arylalkyl)amine produces directly a single (+) or (−) stereoisomer of the aminoalkyl 3-(lower alkylthio)phenyl ketone of Formula V ($R_1$ is hydrogen). Oxidation of the latter affords a pair of diastereomeric aminoalkyl 3-(lower alkylsulfinyl)phenyl ketones of Formula II which, if desired, can be separated using conventional procedures.

Reduction of the stereochemically fixed aminoalkyl phenyl ketone of Formula V as described hereinabove creates a new asymmetric center (i.e. the carbinol carbon atom) and therefore produces a pair of diastereomeric benzenemethanols of Formula IV. If desired the diastereomers can be separated according to known methods, for example, by fractional crystallization of the acid-addition salt of an optically active acid such as (+) or (−) mandelic acid, tartaric acid, O,O-dibenzoyltartaric acid, malic acid and the like, or by converting the diastereomeric mixture to a suitable ester derivative (i.e. Y in Formula I is lower alkanoyl, aroyl, benzenesulfonyl or p-toluenesulfonyl) e.g. the acetate, benzoate, or p-toluenesulfonate and separating the esters by chromatography or by fractional crystallization of a suitable acid-addition salt thereof.

Each of the individual diastereomers of the 3-(lower alkylthio)benzenemethanol of Formula IV as above-produced can be oxidized as described hereinabove again giving rise to a new center of asymmetry (i.e. the sulfur atom) and producing thereby a pair of diastereomeric sulfoxides of Formula I which also can be separated in accordance with the conventional procedures described above.

Alternatively the pair of diastereomeric 3-(lower alkylthio)benzenemethanols can be oxidized directly to give a mixture of four diastereomeric sulfoxides which if desired can also be separated according to the above-described procedures, for example by fractional crystallization of a suitable acid-addition salt such as the hydrochloride or cyclohexylsulfamate.

The pair of diastereomeric 3-(lower alkylthio)benzenemethanols of Formula IV can also be halogenated and reduced to give a single stereoisomer of the lower alkylthio-substituted 2-phenylethylamine of Formula VI. The latter can then be oxidized to give a pair of diastereomeric sulfoxides of Formula III which also can be separated in accordance with the conventional procedures described above.

The compounds of the present invention having Formula I hereinabove exhibit useful antihypertensive, vasodilator and β-adrenergic blocking activity. Of particular advantage is the combination in a single compound of vasodilator and β-adrenergic blocking activity whereby the reflex tachycardia associated with the reduction in blood pressure through vasodilation is effectively reduced or eliminated by β-adrenergic blockade. The compounds are therefore effective in lowering blood pressure without causing undesirable tachycardic effects.

It should be noted, however, that although both vasodilator and β-adrenergic blocking activity reside in the same compound, the time of onset of each of these actions appears to be somewhat different, vasodilation usually preceding β-adrenergic blockade. This can of course give rise to a moderate transient increase in heart rate observable on the first day or two of repeated medication. Thereafter, however, β-adrenergic blockade takes full effect and subsequent continuous medication effects sustained blood pressure lowering with no appreciable elevation of heart rate. Moreover as opposed to the antihypertensive response which is directly dose-related, the heart rate elevation observed at the lower doses tested is not appreciably increased either in magnitude or in duration at higher doses. It is therefore possible to raise the dosage level in order to achieve a further reduction in blood pressure without causing a corresponding increase in heart rate.

A preferred embodiment of this invention is 4-hydroxy-α-<{[3-(4-methoxyphenyl)-1-methylpropyl]amino}-methyl>-3-(methylsulfinyl)benzenemethanol (Formula I wherein $R_1$, $R_2$ and Y are hydrogen; $R_3$ is methyl; n is 2, Ar is 4-methoxyphenyl; and R is methyl) which has high antihypertensive activity and a particularly effective distribution of vasodilator and β-adrenergic blocking activity and is accordingly especially efficacious as an antihypertensive agent with no undesirable tachycardic side effects.

The above-described compound contains three centers of asymmetry (i.e. the carbon atom bearing the methyl group, the carbinol carbon atom and the sulfur atom) and can therefore exist as a mixture of up to eight stereoisomers. Particularly preferred among these are the four diastereomers derived from (+)-4'-hydroxy-2-{[3-(4-methoxyphenyl)-1-methylpropyl]amino}-3'-(methylthio)acetophenone (Formula V wherein $R_1$, $R_2$ and Y are hydrogen; $R_3$ is methyl; n is 2; Ar is 4-methoxyphenyl; and R is methyl) by reduction of the carbonyl group followed by oxidation of the methylthio group. These isomers either individually or as mixtures of any two or more exhibit potent antihypertensive activity with no undesirable tachycardic side effects. Although each of the four diastereomers can be separated from the mixture as described hereinabove this is generally unnecessary and it is therefore economically advantageous to use the mixture as produced.

In carrying out the method aspect of this invention, i.e. the method of reducing hypertension in mammals which comprises administering to said mammals an antihypertensively effective amount of a compound having Formula I, II or III, said compounds can be administered orally in the form of pills, tablets, capsules, e.g. in admixture with talc, starch, milk sugar or other inert, i.e. non-toxic or pharmacologically acceptable pharmaceutical carrier, or in the form of aqueous solutions, suspensions, encapsulated suspensions, gels, elixirs, aqueous alcoholic solutions, e.g. in admixture with sugar or other sweetening agents, flavorings, colorants, thickeners and the other conventional pharmaceutical excipients. When injected subcutaneously, intramuscularly or intravenously, they can be administered, e.g., as an aqueous or peanut oil solution or suspension using excipients and carriers conventional for this node of administration. The best route of administration and the best dosage will be apparent from the laboratory tests for activity and toxicity of the selected compound conventionally undertaken as part of the development phase of a pharmaceutical.

Ordinarily, an oral dosage unit contains about 1 to 50 mg. of the active medicament and is administered as often as required to maintain the desired blood pressure reduction, for example, 1 to 3 times daily.

The molecular structures of the compounds of the invention were assigned on the basis of the method of their preparation and study of their IR and NMR spectra, and confirmed by the correspondence between calculated and found values for the elemental analyses of representative examples.

The identity and purity of individual stereoisomers as well as the composition of stereoisomeric mixtures were determined on the basis of optical rotation and high pressure liquid chromatography.

The invention is illustrated by the following examples without, however, being limited thereto. Unless otherwise specified optical rotations were determined on a 2% solution of the compound in methanol.

EXAMPLE 1

A. To 100 g (0.085 mole) of chlorosulfonic acid at 5° C. was added over a period of 25 minutes 20 g. (0.15 mole) of p-hydroxyacetophenone. The temperature was allowed to gradually rise to 22° C. as the reaction was stirred overnight. The temperature was then raised to 55°–60° C. and stirring was continued an additional hour. The reaction mixture was quenched in ice-water and the precipitated solid was collected and washed with water. The product was dissolved in ethyl acetate and the resulting solution was dried and evaporated to dryness. The residue was recrystallized from benzene to give 12.5 g. of 4'-hydroxy-3'-(chlorosulfonyl)acetophenone, m.p. 138°–142° C. The filtrate afforded a second crop of 5.0 g., m.p. 124°–136° C.

B. Hydrogen chloride was bubbled into a stirred mixture containing 105 g. (0.46 mole) of stannous chloride dihydrate and 400 ml. of glacial acetic acid until a nearly clear solution was obtained. To the latter solution was added portionwise over 20 minutes 18 g. (0.077 mole) of crude 4'-hydroxy-3'-(chlorosulfonyl)acetophenone while the temperature was maintained at 25°–30° C. After the addition was complete stirring was continued an additional 0.5 hours. The reaction mixture was then poured into 400 ml. of 12N hydrochloric acid, diluted with 800 ml. of water and extracted with chloroform. The extracts were washed with saturated aqueous sodium chloride and evaporated to dryness. The residue was recrystallized from benzene to give 4 g. of 4-hydroxy-3'-mercaptoacetophenone, m.p. 117°–120° C.

C. A mixture containing 1.0 g. (0.006 mole) of 4'-hydroxy-3'-mercaptoacetophenone, 0.9 g. (0.0063 mole) of methyl iodide, 0.83 g. (0.006 mole) of potassium carbonate and 12 ml. of acetone was stirred 2.5 hours at room temperature. The reaction mixture was filtered and the filtrate evaporated to dryness. The residue was dissolved in chloroform and the resulting solution was washed with 1N hydrochloric acid, dried over anhydrous sodium sulfate and evaporated to dryness. The residue was dissolved in hot benzene and the solution was filtered through a ¼" pad of silica gel in order to remove a colored impurity. Evaporation of the filtrate afforded 0.9 g. of 4'-hydroxy-3'-(methylthio)acetophenone, m.p. 117°–120° C.

D. Alternatively, to a stirred solution containing 61.4 g. (0.435 mole) of o-(methylthio)phenol and 35 g. (0.45 mole) of acetyl chloride in 170 ml. of nitrobenzene was added portionwise over a period of 20 minutes 80 g. (0.60 mole) of aluminum chloride. The reaction mixture was stirred overnight at room temperature and then one hr. at 65° C. The reaction mixture was cooled, diluted with ice and water and extracted with methylene chloride. The organic extracts were evaporated in vacuo, the residue diluted with ether and allowed to stand two days in the refrigerator. The precipitated product was collected and dried to give 27 g. of 4'-hydroxy-3'-(methylthio)acetophenone.

E. To a cooled, stirred solution containing 24.5 g. (0.134 mole) of 4'-hydroxy-3'-(methylthio)acetophenone and 21 g. (0.21 mole) of triethylamine in 400 ml. of methylene chloride was added dropwise over a period of 30 minutes 16.4 g. (0.21 mole) of acetyl chloride. After stirring overnight at room temperature the reaction mixture was washed with water, dried over anhydrous sodium sulfate, and concentrated to a small volume. The concentrate was diluted with ether and cooled in an ice bath. The resulting precipitate was collected to give 23.5 g. of 4'-hydroxy-3'-(methylthio)acetophenone 4'-acetate.

F. To a stirred mixture containing 23.2 g. (0.108 mole) of 4'-hydroxy-3'-(methylthio)acetophenone 4'-acetate and 9 g. of calcium carbonate in 300 ml. of chloroform was added dropwise over a period of two hours a solution containing 6 ml. (0.108 mole) of bromine in 30 ml. of chloroform. The reaction mixture was filtered, and the filtrate washed with saturatrd aqueous sodium bicarbonate, and evaporated to dryness. The residue was dissolved in ether and the ethereal solution diluted with cyclohexane and cooled in ice. The resulting precipitate was collected and dried to give 26.5 g. of 2-bromo-4'-hydroxy-3'-(methylthio)acetophenone 4'-acetate.

G. To a stirred solution containing 16.5 g. (0.10 mole) of 2-(4-methoxyphenyl)-1-methylethylamine and 5 g. (0.051 mole) of triethylamine in 40 ml. of N,N-dimethylformamide at −65° C. was added dropwise over a period of 2 hours 15.5 g. (0.051 mole) of 2-bromo-4'-hydroxy-3'-(methylthio)acetophenone 4'-acetate in 40 ml. of N,N-dimethylformamide. After the addition was complete stirring at −65° C. was continued an additional hour. The reaction mixture was then acidified with 10 ml. of 12N hydrochloric acid and diluted with 100 ml. of water. Upon shaking the aqueous solution with 200 ml. of a 2:1 mixture of ether-methylene chloride the product began to precipitate from the aqueous phase. The layers were separated and the aqueous portion was cooled in ice. The resulting precipitate was collected and dried 3 hours over phosphorous pentoxide in a 65° vacuum oven to give 12.1 g. of 4'-hydroxy-2-{[2-(4-methoxyphenyl)-1-methylethyl]amino}-3'-(methylthio)acetophenone 4'-acetate hydrochloride.

H. A stirred solution containing 12.5 g. (0.029 mole) of 4'-hydroxy-2-{[2-(4-methoxyphenyl)-1-methylethyl]amino}-3'-(methylthio)acetophenone 4'-acetate hydrochloride in 200 ml. of methanol was cooled in an ice-acetone bath and treated portionwise over 15 minutes with 0.9 g. of sodium borohydride. After the addition was complete stirring was continued an additional 20 minutes. The reaction mixture was then brought to pH 7 with glacial acetic acid and evaporated to dryness. The residue was diluted with ether and washed thoroughly with saturated aqueous sodium bicarbonate. The ethereal solution was dried over anhydrous sodium sulfate and concentrated to a small volume. The concentrate was acidified with ethereal hydrogen chloride and cooled overnight in a refrigerator. The precipitated product was collected and recrystallized from methanol-isopropyl alcohol to give 2.1 g. of 4-hydroxy-α-<{[2-(4-methoxyphenyl-1-methylethyl]amino}methyl>-3-(methylthio)benzenemethanol 4-acetate hydrochloride, m.p. 143°–145° C.

I. A solution containing 1.5 ml. of 30% hydrogen peroxide and the free base liberated from 9 g. of 4-hydroxy-α-<{[2-(4-methoxyphenyl)-1-methylethyl]amino}methyl>-3-(methylthio)benzenemethanol 4-acetate hydrochloride in 150 ml. of methanol was stirred 2 days at room temperature and then 1.5 hours at reflux. The reaction mixture was then evaporated to dryness. The residue was dissolved in water, and the solution filtered to remove insoluble impurities. The filtrate was acidified with 12N hydrochloric acid and evaporated to dryness. The residue was triturated with ether-isopropyl acetate at −65° C. The resulting amorphous solid was dissolved in hot water, filtered to remove insoluble impurities, and the filtrate evaporated to dryness. The residue was triturated with ether and cyclohexane and the resulting solid was collected and dried over phosphorus pentoxide 6 hours at 85° C. affording 4.6 g. of 4-hydroxy-α-<{[2-(4-methoxyphenyl)-1-methylethyl]amino}methyl>-3-(methylsulfinyl)benzenemethanol hydrochloride as an amorphous tan solid, m.p. 115° C.

In addition to its antihypertensive activity this compound was also found to possess β-adrenergic stimulant activity as evidenced by its ability to block histamine-induced bronchoconstriction in the dog.

EXAMPLE 2

A. To a stirred solution containing 24 g. (0.135 mole) of 3-(4-methoxyphenyl)-1-methylpropylamine in 40 ml. of N,N-dimethylformamide at −50° C. was added dropwise over 15 minutes a solution containing 15 g. (0.05 mole) of 2-bromo-4'-hydroxy-3'-(methylthio)acetophenone 4'-acetate in 35 ml. of N,N-dimethylformamide. After the addition was complete stirring was continued an additional 1.25 hours. The reaction mixture was then treated with 4 ml. of 12N hydrochloric acid, diluted with 100 ml. of water and extracted with ether-ethyl acetate. The organic extracts were dried over anhydrous sodium sulfate, acidified with ethanolic hydrogen chloride and evaporated to dryness. The crude product containing both the 4'-acetate and 4'-hydroxy compounds was dissolved in a solution containing 10 ml. of acetyl chloride in 120 ml. of trifluoroacetic acid and stirred 2 hours at room temperature. The solution was then evaporated to dryness and the residue partitioned between ether and water. The ether layer was dried over anhydrous sodium sulfate and acidified with ethanolic hydrogen chloride. The resulting precipitate was collected and triturated with acetone-ether to give 6.0 g. of 4'-hydroxy-2-{[3-(4-methoxyphenyl)-1-methylpropyl]amino}-3'-(methylthio)acetophenone 4'-acetate hydrochloride, m.p. 160°–165° C.

B. To a stirred mixture of 9.0 g. (0.021 mole) of 4'-hydroxy-2-{[3-(4-methoxyphenyl)-1-methylpropyl]amino}-3'-(methylthio)acetophenone 4'-acetate hydrochloride and 100 ml. of methanol at −5° to 0° C. there was added portionwise 0.5 g. (0.015 mole) of sodium borohydride. After stirring an additional 0.5 hour, a solution containing 1.0 g. of potassium hydroxide in 10 ml. of water was added and the resulting mixture was stirred at room temperature under nitrogen overnight, and then at reflux 0.5 hour. The pH was adjusted to 7 with glacial acetic acid and the resulting solution was concentrated to a small volume, diluted with saturated aqueous sodium bicarbonate and extracted with ethyl acetate. The ethyl acetate solution was dried over anhydrous sodium sulfate, acidified with glacial acetic acid, concentrated to a small volume and cooled. The product which separated was collected and recrystallized from ethyl acetate-ethanol affording 7.2 g. of 4-hydroxy-α-<{[3-(4-methoxyphenyl)-1-methylpropyl]amino}methyl>-3-(methylthio)benzenemethanol acetate salt, m.p. 132°–134° C.

C. The latter compound was also prepared as described in following parts C–F. To a stirred solution containing 100 g. (0.55 mole) of 4'-hydroxy-3'-(methylthio)acetophenone in 600 ml. of pyridine at 15°–18° C. there was added dropwise over one hour 68 ml. (0.58 mole) of benzoyl chloride. After addition was complete stirring was continued at room temperature for 1.5 hours. The reaction mixture was then quenched in 1.5 liters of ice-cold water. The solid which precipitated was collected by filtration, washed successively with water, cold 2-propanol, and n-hexane and dried to give 146 g. of 4'-hydroxy-3'-(methylthio)acetophenone 4'-benzoate, m.p. 126°–131° C.

D. To a stirred suspension containing 145 g. (0.51 mole) of 4'-hydroxy-3'-(methylthio)acetophenone 4'-benzoate in 1200 ml. of benzene at 20° C. was added 15 ml. of a solution containing 85 g. (0.53 mole) of bromine in 100 ml. of benzene. The mixture was irradiated with uv light for about 1 hour in order to initiate the reaction. When the reaction commenced (as indicated by decolorization) a slow stream of nitrogen was bubbled through the reaction mixture and the remainder of the bromine solution was added over a period of 2 hours while the temperature was maintained at 20°–24° C. The reaction mixture was stirred an additional 0.5 hour and then cooled to 16° C. The solid which precipitated was collected by filtration, washed with water and n-hexane, and dried to give 90 g. of 2-bromo-4'-hydroxy-3'-(methylthio)acetophenone 4'-benzoate, m.p. 127°–129° C. The benzene solution afforded an additional 21 g. of produce m.p. 126°–129° C.

E. To a stirred solution containing 36 g. (0.2 mole) of 3-(4-methoxyphenyl)-1-methylpropylamine in 175 ml. of N,N-dimethylformamide at −60° C. was added over one hour a solution containing 25 g. (0.068 mole) of 2-bromo-4'-hydroxy-3'-(methylthio)acetophenone 4'-benzoate in 120 ml. of N,N-dimethylformamide. After the addition was complete, stirring at −60° C. was continued an additional 20 minutes. The reaction mixture was then diluted with 200 ml. of chloroform, treated with 20 ml. of 45% hydrogen bromide and further diluted with 200 ml. of cold water. The layers were separated and the aqueous layer was reextracted with chloroform. The organic layers were combined, washed with water, dried over anhydrous magnesium sulfate and concentrated to about 100 ml. The concentrate was diluted with 400 ml. of ether and cooled. The resulting precipitate was collected by filtration, washed successively with cold 2-propanol and ether and dried to give 26 g. of 4'-hydroxy-2-{[3-(4-methoxyphenyl)-1-methylpropyl]amino}-3'-(methylthio)acetophenone 4'-benzoate hydrobromide.

F. To a stirred mixture of 25 g. (0.046 mole) of 4'-hydroxy-2-{[3-(4-methoxyphenyl)-1-methylpropyl]amino}-3'-(methylthio)acetophenone 4'-benzoate hydrobromide and 160 ml. of methanol at 0° C. was added portionwise over 0.5 hour 1.4 g. (0.037 mole) of sodium borohydride. After stirring an additional 20 minutes the reaction mixture was treated with a solution containing 2.5 g. of potassium hydroxide in 30 ml. of water and heated under reflux 40 minutes. The reaction mixture was concentrated in vacuo until a cloudy suspension formed. The suspension was brought to pH 3 with 6N hydrochloric acid and then made basic with saturated aqueous sodium bicarbonate. The remaining methanol was removed by evaporation in vacuo. The resulting suspension was diluted with 200 ml. of ethyl acetate and the resulting biphasic mixture was allowed to stand overnight. The solid which precipitated was collected, washed with water followed by n-pentane and recrystallized from 2-propanol to give 6 g. of 4-hydroxy-α-<{3-(4-methoxyphenyl)-1-methylpropyl]amino}-methyl>-3-(methylthio)benzenemethanol, m.p. 126°-129° C.

The ethyl acetate layer in the filtrate was separated, washed successively with dilute aqueous sodium bicarbonate and water, and dried over anhydrous magnesium sulfate. The resulting solution was diluted with 120 ml. of isopropyl acetate, treated with 3 ml. of glacial acetic acid, seeded and cooled. The resulting precipitate was collected, washed with isopropyl acetate and dried at 65° C. in vacuo affording 7 g. of product as the acetate salt, m.p. 132°-134° C.

G. To a stirred solution solution containing 3.5 g. (0.0083 mole) of 4-hydroxy-α-<{[3-(4-methoxyphenyl)-1-methylpropyl]amino}methyl>-3-(methylthio)benzenemethanol acetate salt in 100 ml. of methanol at −5° C. was added dropwise over 0.05 hour a solution containing 630 mg. (0.0083 mole) of commercial 40% peracetic acid in 10 ml. of methanol. When the addition was complete the reaction mixture was evaporated to dryness. The resulting oil was diluted with ethyl acetate and the gum which separated was allowed to stand 2 days in a refrigerator under a mixture of ethyl acetate and ethanol. The resulting off-white amorphous solid was collected affording 3.2 g. of 4-hydroxyα-<{[3-(4-methoxyphenyl)-1-methylpropyl]amino}methyl>-3-(methylsulfinyl)benzenemethanol acetate salt, which softened at 95° C. and melted at 100°-105° C.

H. The latter compound was also prepared as follows: To a stirred solution containing 50 g. (0.119 mole) of 4-hydroxy-α-<{[3-(4-methoxyphenyl)-1-methylpropyl]amino}methyl>-3-(methylthio)benzenemethanol acetate salt in 500 ml. of methanol at 0° C. there was added dropwise over 70 minutes 20.2 ml. (0.119 mole) of commercial 40% peracetic acid. When the addition was complete the reaction mixture was evaporated to dryness in vacuo. The residual oil was taken up in 50 ml. of ethyl acetate and again evaporated to dryness in vacuo. The remaining oil was dissolved in 350 ml. of tetrahydrofuran and the resulting clear solution was stirred and made slightly cloudy by the gradual addition of ether. After seeding, the mixture was stirred 2 days at room temperature at which point a fine, white solid had begun to precipitate. The mixture was treated dropwise with 50 ml. of ether and stirred 5 hours followed by the dropwise addition of another 50 ml. of ether and stirring an additional 4 hours. After stirring overnight in a refrigerator the mixture was cooled to 0° C. while 200 ml. of ether was added dropwise over 3 hours. Stirring at 0° C. was continued an additional 3 hours. The precipitated product was then collected and redissolved in 1250 ml. of tetrahydrofuran. The resulting solution was filtered to remove a small amount of insoluble material, and concentrated to a volume of 250 ml. The concentrate was cooled in a refrigerator overnight. The resulting white crystalline precipitate was collected, washed with tetrahydrofuran and ether and dried affording 14.5 g. of 4-hydroxy-α-<{[3-(4-methoxyphenyl)-1-methylpropyl]amino}methyl>-3-(methylsulfinyl)benzenemethanol acetate salt, m.p. 131°-133° C.

EXAMPLE 3

A. To a stirred solution containing 376 g. (1.0 mole) of (−)-dibenzoyltartaric acid in a mixture of 5 l. of methanol and 550 ml. of water at 42° C. there was added 179 g. (1.0 mole) of (+)-3-(4-methoxyphenyl)-1-methylpropylamine. The mixture was stirred 26 hours at 40° C. and then 20 hours at room temperature. The resulting precipitate was collected and dried affording a first crop of 176.5 g. of (−)-3-(4-methoxyphenyl)-1-methylpropylamine (−)-dibenzoyltartrate salt, m.p. 175°-176° C. (dec.), $[\alpha]_D^{25} = -88.0°$. By cooling the filtrate at 0° C. for 7 hours a second crop of 58.5 g. was obtained, m.p. 167°-171° C. (dec.) $[\alpha]_D^{25} = -86.3°$. The final mother liquors were set aside for use in part B below. The first crop was recrystallized from 90% methanol to give 145.3 g., m.p. 179°-180.5° C. $[\alpha]_D^{25} = -87.5°$. This salt was treated with aqueous sodium hydroxide and the liberated amine extracted into chloroform. The chloroform extracts were dried over anhydrous potassium carbonate and evaporated to dryness. The residual oil was dissolved in 2-propanol, the resulting solution acidified with 25 ml. of 12N hydrochloric acid, and evaporated to dryness. The solid residue was dried, recrystallized from 2-propanol and dried again to give 52.0 g. of (−)-3-(4-methoxyphenyl)-1-methylpropylamine hydrochloride, m.p. 126°-129° C., $[\alpha]_D^{25} = -6.0°$ (2% in water).

B. The mother liquors remaining after isolation of (−)-3-(4-methoxyphenyl)-1-methylpropylamine (−)-dibenzoyltartrate salt were concentrated to a volume of 500 ml. and cooled at 0° C. for 2 hours. The resulting precipitate was collected and dried to give 283 g. of (+)-3-(4-methoxyphenyl)methylpropylamine (−)-dibenzoyltartrate salt, m.p. 159°-162° C. (dec.). This salt was treated with aqueous sodium hydroxide and the liberated amine extracted into chloroform. Evaporation of the chloroform left 80 g. of oil which was then added to a solution containing 168 g. of (+)-dibenzoyltartaric acid in 1860 ml. of 90% methanol. After stirring 20 hours at room temperature the precipitated salt was collected and dried affording 173.5 g. of (+)-3-(4-methoxyphenyl)-1-methylpropylamine (+)-dibenzoyltartrate, m.p. 179°-180° C. (dec.), $[\alpha]_D^{25} = +87.1°$. Recrystallization from 90% methanol afforded 149 g., m.p. 181° C. (dec.), $[\alpha]_D^{25} = +90.3°$. Following the procedure described in part A the amine was liberated from the (+)-dibenzoyltartrate salt and converted to the hydrochloride to give 55.0 g. of (+)-3-(4-methoxyphenyl)-1-methylpropylamine hydrochloride, m.p. 127°–130° C., $[\alpha]_D^{25} = +5.6°$ (2% in water). The nmr spectrum of this product in the presence of the shift reagent tris[(trifluoromethyl)hydroxymethylene-α-camphorato]europium III, Eu(TFC)$_3$ indicated contamination by approximately 10–15% of the levo isomer.

C. (+)-3-(4-Methoxyphenyl)-1-methylpropylamine (−)-dibenzoyltartrate salt (8781 g.) prepared according to part B above was recrystallized from aqueous methanol to give 7690 g., m.p. 163°–165° C. A 700-gram sample was recrystallized twice from aqueous methanol affording 558 g. of the salt which was then converted to the free amine and distilled under reduced pressure to give 180.5 g. of (+)-3-(4-methoxyphenyl)-1-methylpropylamine, b.p. 88°–100° C./0.1 mm. The nmr spectrum of this product in the presence of the shift reagent Eu(TFC)$_3$ indicated an optical purity ≧97%.

D. Alternatively (+)-3-(4-methoxyphenyl)-1-methylpropylamine was obtained as follows:

A solution of 300 g. (1.67 moles) of (±)-3-(4-methoxyphenyl)-1-methylpropylamine in 2 l. of 95% ethanol was added in one portion to a stirred warm solution (40°–45° C.) of 250 g. (1.67 moles) of d-tartaric acid in 2.6 l. of water and 4.2 l. of 95% ethanol. The clear solution was seeded at about 38° C. and was then allowed to come to room temperature overnight with stirring. The crystallized solid was filtered and pressed thoroughly with a rubber dam; it was washed twice with enough ice-cold 8% aqueous ethanol to cover the cake and was thoroughly pressed dry. The product was dried at 60° in vacuo for five hours to afford 276 g. of crude d-amine bitartrate, m.p. 181°–182° C. Five recrystallizations from aqueous ethanol afforded 125 g. of the bitartrite, m.p. 188°–190° C. The optical purity of the liberated (+)-3-(4-methoxyphenyl)-1-methylpropylamine was shown to be ≧97%.

EXAMPLE 4

A. To a stirred solution containing 35.7 g. (0.172 mole) of incompletely resolved (−)-3-(4-methoxyphenyl)-1-methylpropylamine hydrochloride, $[\alpha]_D^{25} = -6.0°$ (2% in water) in 125 ml. of N,N-dimethylformamide was added 25 ml. of triethylamine causing immediate precipitate of triethylamine hydrochloride. The mixture was stirred 20 minutes and then cooled to −50° C. The remainder of the preparation was carried out following a procedure similar to that in Example 2A but using 20 g. (0.66 mole) of 2-bromo-4'-hydroxy-3'-(methylthio)acetophenone 4'-acetate and 8 ml. of acetyl chloride to give 15 g. of incompletely resolved (−)-4'-hydroxy-2-{[3-(4-methoxyphenyl)-1-methylpropyl]amino}-3'-(methylthio)acetophenone 4'-acetate hydrochloride, m.p. 179°–181° C., $[\alpha]_D^{25} = 10.3°$.

B. To a stirred solution containing 12 g. (0.027 mole) of incompletely resolved (−)-4'-hydroxy-2-{[3-(4-methoxyphenyl)-1-methylpropyl]amino}-3'-(methylthio)acetophenone 40'-acetate hydrochloride (m.p. 179°–181° C., $[\alpha]_D^{25} = -10.3°$) in 150 ml. of methanol at 0° C. was added portionwise 0.8 g. (0.020 mole) of sodium borohydride. After stirring an additional 15 minutes, a solution containing 1.6 g. of potassium hydroxide in 25 ml. of water was added and the resulting mixture was heated at reflux under nitrogen 0.5 hours. The reaction mixture was concentrated to a small volume, acidified with 3N hydrochloric acid, then made basic with saturated aqueous sodium bicarbonate and extracted with ethyl acetate. After drying over anhydrous sodium sulfate the ethyl acetate solution was evaporated to dryness leaving 11 g. of pale yellow oil. This oil was dissolved in 200 ml. of ethyl acetate and a 40 ml. aliquot was absorbed on a column of silica gel and the product eluted with 92:8 ethyl acetate-methanol to give 1.7 g. of oil which was converted to the acetate salt affording 1.22 g. of levorotatory 4-hydroxy-α-<{[3-(4-methoxyphenyl)-1-methylpropyl]amino}methyl>-3-(methylthio)benzenemethanol acetate salt, m.p. 124°–125° C., $[\alpha]_D^{25} = -6.4°$.

C. Following a procedure similar to that described in Example 2G but using 1.2 g. (0.0028 mole) of levorotatory 4-hydroxy-α-<{[3-(4-methoxyphenyl)-1-methylpropyl]amino}methyl>-3-(methylthio)benzenemethanol acetate salt (m.p. 124°–125° C., $[\alpha]_D^{25} = -6.4°$) and 216 mg. of commercial 40% peracetic acid there was obtained 0.9 g. of levorotatory 4-hydroxy-α-<{[3-(4-methoxyphenyl)-1-methylpropyl]amino}methyl>-3-(methylsulfinyl)benzenemethanol acetate salt, m.p. 103°–106° C., $[\alpha]_D^{25} = -3.0°$.

EXAMPLE 5

A. Following a procedure similar to that described in Example 4A but using 43 g. (0.20 mole) of incompletely resolved (+)-3-(4-methoxyphenyl)-1-methylpropylamine hydrochloride, $[\alpha]_D^{25} = +5.6°$ (2% in water) and 23 g. (0.077 mole) of 2-bromo-4'-hydroxy-3'-(methylthio)acetophenone 4'-acetate there was obtained 17.1 g. of incompletely resolved (+)-4'-hydroxy-2-{[3-(4-methoxyphenyl)-1-methylpropyl]amino}-3'-(methylthio)acetophenone 4'-acetate hydrochloride, m.p. 178°–180° C., $[\alpha]_D^{25} = +10.2°$.

B. Following a procedure similar to that described in Example 4B but using 17.1 g. (0.039 mole) of (+)-4'-hydroxy-2-{[3-(4-methoxyphenyl)-1-methylpropyl]amino}-3'-(methylthio)acetophenone 4'-acetate hydrochloride (m.p. 178°–180° C., $[\alpha]_D^{25} = +10.2°$), 1.0 g. (0.025 mole) of sodium borohydride and 2.0 g. of potassium hydroxide there was obtained 15 g. of 4-hydroxy-α-<{[3-(4-methoxyphenyl)-1-methylpropyl]amino}methyl>-3-(methylthio)benzenemethanol as a dextrorotatory pair of diastereomeric benzenemethanols. A 3.0-gram sample was dissolved in isopropyl acetate and the resulting solution acidified with glacial acetic acid. The product was allowed to crystallize slowly over 2 days to give 2.75 g. of crystalline acetate salt, m.p. 124°–126° C., $[\alpha]_D^{25} = +7.7°$.

C. Following a procedure similar to that described in Example 2F but employing 40 g. (0.0758 mole) of optically pure (+)-4'-hydroxy-2-[3-(4-methoxyphenyl)-1-methylpropyl]amino-3'-(methylthio)acetophenone 4'-benzoate hydrobromide (m.p. 171°–175° C., $[\alpha]_D^{25} = +11.8°$) prepared according to Example 7B hereinbelow, 1.5 g. of sodium borohydride and 4.5 g. of potassium hydroxide there was obtained 25.1 g. of 4-hydroxy-α-<{[3-(4-methoxyphenyl)-1-methylpropyl]amino}methyl>-3-(methylthio)benzenemethanol acetate salt, m.p. 125°–127° C., $[\alpha]_D^{25} = +7.3°$, as a dextrorotatory pair of diastereomeric benzenemethanols. Another similar run afforded a product with m.p. 129°–130° C., $[\alpha]_D^{25} = +7.1°$. The hydrochloride had m.p. 153°–155° C. Another run produced a hydrochloride m.p. 155°–157° C., $[\alpha]_D^{25} = +8.8°$.

The pair of diastereomeric benzenemthanols of this Example correspond to the products of Examples 6C and 9C.

D. Following a procedure similar to that described in Example 2G but using 2.5 g. (0.0049 mole) of dextrorotatory 4-hydroxy-α-<{[3-(4-methoxyphenyl)-1-methylpropyl]amino}methyl>-3-(methylthio)benzenemethanol acetate salt (m.p. 124°–126° C., $[\alpha]_D^{25} = +7.7°$) and 375 mg. of commercial 40% peracetic acid there was obtained 2.0 g. of 4-hydroxy-α-<}[3-(4-methoxyphenyl)-1-methylpropyl]amino}methyl>-3-(methylsulfinyl)benzenemethanol acetate salt as an amorphous yellow powder $[\alpha]_D^{25} = +4.2°$ containing a mixture of 4 diastereomeric sulfoxides. In addition to its antihypertensive activity this product was found equiactive with procaine as a local anesthetic when tested according to the method of Bulbring and Wadja, J. Pharm. Exp. Therap. 85, 78 (1945).

E. When the above oxidation was carried out on dextrorotatory 4-hydroxy-α-<{[3-(4-methoxyphenyl)-1-methylpropyl]amino}methyl>-3-(methylthio)benzenemethanol acetate salt prepared according to the method of part C above the product had m.p. 103°–110° C. and $[\alpha]_D^{25} = -1.1°$ and consisted of a mixture of 4 diastereomeric sulfoxides.

F. A sample of 4-hydroxy-α-<}[3-(4-methoxyphenyl)-1-methylpropyl]amino}methyl>-3-(methylsulfinyl)benzenemethanol acetate salt prepared by a procedure similar to that described in part E above was converted by a conventional procedure to the corresponding phosphate, m.p. 136°–153° C., $[\alpha]_D^{25} = 0.0°$.

G. A sample of 4-hydroxy-α-<{[3-(4-methoxyphenyl)-1-methylpropyl]amino}methyl>-3-(methylsulfinyl)benzenemethanol acetate salt prepared by a procedure similar to that described in part E above was converted by a conventional procedure to the corresponding methanesulfonate, m.p. 142°–148° C., $[\alpha]_D^{25} = +5.0$.

H. A sample of 4-hydroxy-α-<{[3-(4-methoxyphenyl)-1-methylpropyl]amino}methyl>-3-(methylsulfinyl)benzenemethanol acetate salt prepared by a procedure similar to that described in part E above was converted by a conventional procedure to the corresponding hydrochloride, m.p. 172°–175° C., $[\alpha]_D^{25} = -8.1°$.

I. Alternatively the hydrochloride salt was prepared directly as follows:

To a stirred solution containing 844 g. (2 moles) of 4-hydroxy-α-<{[3-(4-methoxyphenyl)-1-methylpropyl]amino}methyl>-3-(methylthio)benzenemethanol acetate salt in 7 liters of methanol at 0° C. was added in 25-ml. portions over a period of about 40 minutes 308 ml. of 40% commercial peracetic acid. Stirring was continued at 0°–3° C. an additional 45 minutes. The reaction mixture was then evaporated under reduced pressure while maintaining the temperature below 35° C. The residue was diluted with 1 liter of 2-propanol and the solution evaporated to dryness in vacuo. This was repeated once more and then the residue was dissolved in 6 liters of 2-propanol, and the resulting solution treated with a solution containing 2.14 moles of hydrogen chloride in 2-propanol. The resulting pale yellow solution was cooled in ice. The precipitated product was collected, washed with 2-propanol-ether and dried to give 705 g. of 4-hydroxy-α-<{[3-(4-methoxyphenyl)-1-methylpropyl]amino}methyl>-3-(methylsulfinyl)benzenemethanol hydrochloride, $[\alpha]_D^{25} = -1.6°$.

The four diastereomeric sulfoxides produced in accordance with the foregoing examples correspond to the sulfoxides of Examples 10, 11, 12 and 13.

The products of several preparations carried out as described above in Example 5I were converted to the phenol p-toluenesulfonates with p-toluenesulfonyl chloride in excess sodium hydroxide and analyzed by high pressure liquid chromatography on microparticulate silica gel using n-hexane-2-propanol-2-propylamine (85:15:0.4) as eluent at a flow rate of 0.54 ml./min. and a pressure of about 1200 p.s.i. and were found to have the following composition:

| Sulfoxide of Ex. No. | Concentration |
| --- | --- |
| 10 | 19–23% |
| 11 | 23–25.5% |
| 12 | 25.5–28% |
| 13 | 28–30% |

The product obtained according to part H or I above, when tested in one or more of the standard biological test procedures described hereinbelow, was found to possess useful cardiotonic activity. The efficacy of this compound was judged, in vitro, on the basis of percent increase in contractile force in isolated cat atria and papillary muscle and, in vitro, on the basis of percent increase in cardiac contractile force in the intact anesthetized dog.

The in vitro test procedures used are described as follows:

Cardiotonic Test Procedure I—Male cats weighing from 0.8 to 1.5 kg. were anesthetized with α-chloralose (80 mg./kg. i.p.). The chest was opened, the heart excised and the two atria dissected. A silk suture was tied to each of two opposite sides of the right atrium. One side of the atrium was tied to a glass rod and then mounted in a 50 ml. organ bath filled with Tyrode's solution. The second suture was attached to a force displacement transducer and the tension on the atrium was adjusted to 1.5±0.5 grams. The transducer was then connected to a Grass polygraph and the force and rate of atrial contraction was recorded continuously. The left atrium was treated similarly using silver wire instead of silk sutures. The silver wire also served as a stimulating electrode. Both atria were mounted in the same bath. The right atrium was beating spontaneously due to the presence of the sinoatrial node, while the left atrium was stimulated electrically at a rate of 3 beats/sec. by suprathreshold rectangular pulses of 5 millisecond duration. The Tyrode's solution bathing the atria was of the following composition (in mM): NaCl 136.87, KCl 5.36, $NaH_2PO_4$ 0.41, $CaCl_2$ 1.80, $MgCl_2 6H_2O$ 1.05, $NaHCO_3$ 11.90, glucose 5.55 and EDTA 0.04. The solution was equilibrated with a gas mixture consisting of 95% $O_2$ and 5% $CO_2$. The preparation was left to equilibrate for one hour before any drug was added. The bathing fluid was changed 3 to 4 times during the equilibration time. At the end of equilibration period, the drug dissolved in a vehicle or the vehicle alone was added to the tissue bath and the full response recorded. The vehicle used was Tyrode's solution to which, if required, sufficient acid was added to cause solution of the drug. When the response reached a maximum it was abolished by 3 washes at 10 min. intervals or until pre-drug values of force of contraction were reached. Generally, a dose response study of at least 3 doses was done in the same preparation.

Cardiotonic Test Procedure IB—Male cats 0.8 to 1.5 kg. were anethetized with α-chloralose (80 mg./kg. i.p.). The chest was opened and the heart excised. The heart was dipped and shaken in Tyrode's solution for the removal of blood from the cavities. The right ventricle was then slit open and the small and thin (about 1 mm. in diameter and 4 to 7 mm. in length) papillary muscles were dissected out. A silver wire was attached to each of the two ends of the papillary muscle. The ventricular end was attached to a platinum electrode and mounted in a tissue bath containing Tyrode's solution described above. The silver wire on the valvular end of the muscle was attached to a force displacement transducer for the measurement of the force and rate of muscle contraction. The muscle was stimulated at a rate of 3 beats/sec. by suprathreshold rectangular pulses of 5 millisecond duration. The rest of the procedure was continued as described above.

Cardiotonic Test Procedure II—The in vivo test procedure used is described as follows: Mongrel dogs of both sexes and varying in weight from 9 to 15 kg. were anesthetized with 30 mg./kg. pentobarbital sodium administered intravenously. The trachea was exposed and cannulated. The tracheal cannula was then attached to a Harvard respiratory pump using room air. The right femoral artery and vein were cannulated. The arterial cannula was attached to a Statham P23A pressure transducer connected to a Grass polygraph for the continuous recording of arterial blood pressure. The venous cannula was used for the intravenous administration of drugs. Pin electrodes were attached to the right forelimb and left hindlimb. The electrodes were then connected to a Grass polygraph for the continuous recording of the standard limb lead II electrocardiogram. A ventro-dorsal incision at the third inter-costal space was made, the ribs laterally retracted and the pericardium slit open to expose the myocardium. The base of the aorta was dissected and a flow probe was fitted around it. The flow probe was attached to a square wave electromagnetic flowmeter (Carolina Medical Electronics). The flowmeter was then connected to a Grass polygraph for the continuous recording of aortic blood flow. This flow was used as an index of cardiac output (actual cardiac output is aortic blood flow+coronary blood flow). Cardiac contractile force was measured by suturing a Walton-Brodie strain gauge to the wall of the right ventricle. At the end of the surgical procedure, the animal was left to rest and equilibrate for one hour with continuous recording of blood pressure, EKG, cardiac contractile force and aortic blood flow. After the equilibration period, the vehicle or the drug dissolved in the vehicle was administered by intravenous infusion (i.v. inf.), intravenous bolus (i.v. bol.) or intraduodenally (i.d.) and the response of all the parameters measured to drug administration was recorded continuously for different period of times depending on the route of drug administration. When the route of administration was i.v. inf., the drug was administered until a peak effect was reached and infusion was then maintained for ten minutes. The above-described test systems were standardized using dopamine.

The product obtained according to part H and I above, when tested in vitro as above-described at a dose of 1 mg./ml. caused increases of 62 and 52 percent in right atrial rate and right atrial force respectively and a decrease of 14 percent in papillary muscle force. At a dose of 10 mcg./ml. increases of 53 and 46 percent in right atrial rate and right atrial force respectively and a decrease of 12 percent in papillary muscle force were observed.

When infused intravenously at a dose of 10 mcg./kg./min. over 3 hrs. in 3 intact anesthetized dogs the product of this example caused a maximum increase in cardiac contractile force of 25 and 42 percent in 2 of 3 dogs with no significant change in heart rate. In the remaining dog decreases in contractile force and heart rate of 30 and 33 percent respectively were observed.

EXAMPLE 6

A. A solution containing 10.5 g. of dextrorotatory 4-hydroxy-α-<{[3-(4-methoxyphenyl)-1-methylpropyl]amino}methyl>-3-methylthio)benzenemethanol prepared as described in Example 5B and 2.25 g. of (−)-mandelic acid in 60 ml. of isopropyl acetate was stirred 4.5 hours. The precipitated solid was collected to give 3.7 g. of white crystalline solid, m.p. 99°–100° C., $[\alpha]_D^{25} = -20.9°$ which was labeled "solid A" and set aside. The filtrate was washed with saturated aqueous sodium bicarbonate, dried over anhydrous sodium sulfate and evaporated to dryness. The residual 6 g. of gum was dissolved in 40 ml. of isopropyl acetate and treated with a solution of 2.0 g. of (+)-mandelic acid in 20 ml. of isopropyl acetate and the resulting solution stirred overnight. The precipitated product was collected giving 4.1 g. of tan crystalline solid m.p. 89°–93° C., $[\alpha]_D^{25} = +35.4°$. The filtrate was labeled "filtrate A" and set aside. The solid was recrystallized by dissolving in 55 ml. of 10:1 isopropyl acetate-isopropyl alcohol and stirring overnight. After removing a small amount of solid impurity the clear solution was concentrated to a volume of 30 ml. whereupon the product crystallized to give 1.6 g. of tan crystals m.p. 89°–106° C., $[\alpha]_D^{25} = +48.7°$, which was labeled "solid B" and set aside. The filtrate was labeled "filbrate B".

"Filtrate A" was washed with saturated aqueous sodium bicarbonate, dried over anhydrous sodium sulfate and evaporated to dryness. The resulting 4.0 g. of yellow gum was dissolved in 40 ml. of ethyl acetate and treated with 1.0 g. of (−)-mandelic acid. After standing overnight the precipitated product was collected to give 2.5 g. of crystalline solid m.p. 108°–110.5° C., $[\alpha]_D^{25} = -33°$ which was labeled "solid C" and set aside. The filtrate was combined with "filtrate B" above and evaporated to dryness, and the residue combined with "solid A". The combined materials were dissolved in ethyl acetate, the resulting solution washed with saturated aqueous sodium bicarbonate, dried over anhydrous sodium sulfate and evaporated to dryness. The residual 6.4 g. of yellow syrup was dissolved in 40 ml. of ethyl acetate and treated with 1.5 g. of (+)-mandelic acid. After stirring overnight the precipitated solid was collected to give a first crop of 1.0 g. of tan solid m.p. 105°–110° C. Cooling the filtrate in ice afforded a second crop of 1.3 g. m.p. 86°–89° C. $[\alpha]_D^{25} = +48°$. The filtrate was labeled "filtrate C" and set aside. The first crop was combined with "solid B" above and recrystallized from ethyl acetate to give 1.65 g. of tan solid m.p. 90.5°–92° C., $[\alpha]_D^{25} = +52.2°$. This material was combined with the second crop and the whole recrystallized from isopropyl acetate affording 2.7 g. of tan crystalline solid m.p. 89°–92.5° C., $[\alpha]_D^{25} = +51.8°$. The latter was dissolved in 50 ml. of ethyl acetate and the resulting solution washed with saturated aqueous sodium bicarbonate, dried over anhydrous sodium sulfate and evaporated to dryness leaving 1.7 g. of product which corresponds to the dextrorotatory member of the pair of diastereomeric benzenemethanols present in the product of Example 5B. A 650-mg. sample was dissolved in isopropyl acetate and the resulting solution acidified with glacial acetic acid and evaporated to dryness. The residue was crystallized from a small volume of isopropyl acetate to give 700 mg. of the acetate salt, m.p. 70°-72° C., $[\alpha]_D^{25} = +31.3°$.

B. "Filtrate C" was evaporated to dryness. The residue was dissolved in ether-ethyl acetate and the resulting solution washed with saturated aqueous sodium bicarbonate, treated with 2 g. of decolorizing carbon, filtered and the filtrate evaporated to dryness leaving 3.8 g. of residue. This material was dissolved in 25 ml. of isopropyl acetate and the resulting solution treated with a solution containing 1.3 g. of (−)-mandelic acid in 10 ml. of isopropyl acetate. After stirring 2 days the precipitated product was collected to give 3.25 g. of white crystalline solid, m.p. 104°-106° C., $[\alpha]^{D25} = -30.4°$. This material was combined with "solid C" above and the whole recrystallized successively from 25 ml. of ethyl acetate, 40 ml. of ethyl acetate and finally from isopropyl alcohol-ethyl acetate in each instance allowing the product to crystallize slowly at room temperature. There was thus obtained 3.5 g. of white needles m.p. 110°-111° C., $[\alpha]_D^{25} = -33.4°$. The latter was dissolved in 50 ml. of ethyl acetate, and the resulting solution washed with saturated aqueous sodium bicarbonate, dried over anhydrous sodium sulfate and evaporated to dryness to give 2.4 g. of product $[\alpha]_D^{25} = -5.1°$ which corresponds to the levorotatory member of the pair of diastereomeric benzenemethanols present in the product of Example 5B. A 1.1-gram sample was converted to the acetate salt as described above for the dextrorotatory diastereomer affording the crystalline acetate salt as white platelets m.p. 124°-124.5° C., $[\alpha]_D^{25} = -5.4$.

C. A 99-gram sample of dextrorotatory 4-hydroxy-α-<{[3-(4-methoxyphenyl)-1-methylpropyl]amino}methyl>-3-(methylthio)benzenemethanol acetate salt (m.p. 129°-130° C., $[\alpha]_D^{25} = +7.1°$) prepared as described in Example 5C was treated with aqueous sodium carbonate and the free base was extracted into 1 liter of ethyl acetate. The ethyl acetate solution was washed with water and saturated aqueous sodium chloride, dried over anhydrous sodium sulfate and evaporated to dryness. The residual oil was dissolved in hot ether and the solution was filtered through a 1-inch pad of silica gel in order to remove a colored impurity. Evaporation of the ether left 83 g. of a pale yellow gum which was dissolved in 200 ml. of ethyl acetate and treated with a solution containing 22 g. of (+)-mandelic acid in 200 ml. of ethyl acetate. The mixture was stirred overnight at room temperature and then overnight at 5° C. The precipitated product was collected by filtration and washed with isopropyl acetate and ether. The mother liquors were set aside. The collected solid was recrystallized from isopropyl acetate containing a small amount of 2-propanol to give 27 g. of product m.p. 89°-91° C., $[\alpha]_D^{25} = +49.4°$. The mother liquors which had been set aside were reconverted to the free base and again treated with 20 g. of (+)-mandelic acid to give after two recrystallizations from isopropyl acetate and one from ethyl acetate an additional 6.0 g. of product $[\alpha]_D^{25} = +47.6°$. The mother liquors from this second treatment with (+)-mandelic acid were enriched in the levorotatory diastereomer and were set aside for use in part D. The solids were combined and recrystallized twice from ethyl acetate to give 22 g. of the (+)-mandelate salt, m.p. 94°-95.5° C. $[\alpha]_D^{25} = +54.0°$. This salt was treated with 80 ml. of 10% aqueous sodium carbonate and the free base extracted into 300 ml. of ethyl acetate. The ethyl acetate solution was washed with saturated aqueous sodium chloride, dried over anhydrous sodium sulfate and acidified with 2 ml. of acetic acid. The solution was concentrated and the resulting precipitate was collected and recrystallized from ethyl acetate containing a few drops of acetic acid to give 4.3 g. of 4-hydroxy-α-<{[3-(4-methoxyphenyl)-1-methylpropyl]amino}methyl>-3-(methylthio)benzenemethanol acetate salt, m.p. 133°-134° C., $[\alpha]_D^{25} = +33.3°$, corresponding to the dextrorotatory member of the pair of diastereomeric benzenemathanols present in the product of Example 5C.

A sample of this material was reacted with p-toluenesulfonyl chloride in the presence of sodium hydroxide to afford the corresponding 4-p-toluenesulfonate acetate salt m.p. 90°-92° $[\alpha]_D^{25} = +23.0°$ which was shown by high pressure liquid chromatography to have a isomeric purity $\geq 99\%$.

D. The mother liquors from part C which were enriched in the levoratatory diastereomer were combined and evaporated to dryness. The residue was treated with aqueous sodium carbonate and the free base extracted into ethyl acetate. Evaporation of the ethyl acetate left 58 g. of oil. This material was dissolved in 200 ml. of ethyl acetate, treated with a solution containing 20 g. of (−)-mandelic acid in 200 ml. of ethyl acetate and the resulting mixture stirred overnight. The precipitated salt was collected and recrystallized successively from acetone-ether, ethyl acetate, and eight times from methylene chloride-ethyl acetate to give 23 g. of incompletely resolved (as determined by thin layer chromatography) (−)-mandelate salt, m.p. 116°-117° C., $[\alpha]_D^{25} = -37.1°$ which was converted by a conventional procedure to the acetate salt $[\alpha]_D^{25} = -10.6°$. Chromatography of a 5.5-gram sample of the latter on a column of silica gel and elution with 7% methanol in ethyl acetate failed to substantially further purify the acetate salt. A 2.6-gram fraction of material which had been eluted from the column was stirred with 25 ml. of 35% aqueous sodium hydroxide and the mixture treated dropwise over 15 minutes with a solution containing 1.33 g. of p-toluenesulfonyl chloride in 30 ml. of acetone. Over the next 5 minutes the reaction mixture was treated with two additional 150-mg. portions of p-toluenesulfonyl chloride. The acetone layer was separated, diluted with an equal volume of isopropyl acetate, washed with water followed by saturated aqueous sodium chloride, and evaporated to dryness. The residue was dissolved in ethyl acetate and the solution acidified with acetic acid. The acetate salt which precipitated was recrystallized from ethyl acetate to give 1.0 g. m.p. 115°-117° C., $[\alpha]_D^{25} = -7.9°$. The filtrate afforded an additional 0.5 g., m.p. 115°-117° C. The crops were combined and converted to 1.2 g. of the (+)-mandelate salt, m.p. 154°-156° $[\alpha]_D^{25} = +14.9°$ according to the procedure described above in part C. This material was combined with another 250 mg. m.p. 157°-158° C. $[\alpha]_D^{25} = +14.3°$ obtained in a similar run, recrystallized from ethyl acetate, and then converted by a conventional procedure to the corresponding acetate salt to give 700 ml. of isomerically pure levorotatory 4-hydroxy-α-<{[3-(4-methoxyphenyl)-1-methylpropyl]-amino}methyl>-3-(methylthio)benzenemethanol-4-p-toluenesulfonate acetate salt, m.p. 117°-119° C. $[\alpha]_D^{25} = -9.6°$ corresponding to the 4-p-toluenesulfonate ester of the levorotatory member of the pair of diastereomeric benzenemanthanols present in the product of Example 5C. This product was shown by high pressure liquid chromatography to have an isomeric purity $\geq 98\%$.

Attempts to cleave the p-toluenesulfonate ester in order to obtain the isomerically pure levorotatory phenol were unsuccessful, however the latter compound was obtained from the corresponding benzoate as described in Example 9C hereinbelow.

E. To a stirred solution containing 1.05 g. (0.003 mole) of dextrorotatory 4-hydroxy-α-<{[3-(4-methoxyphenyl)-1-methylpropyl]amino}methyl>-3-(methylthio)benzenemethanol prepared according to the method of part A above in 15 ml. of methanol at 0° C. there was added dropwise over 0.5 hour a solution of 0.45 ml. (0.003 mole) of commercial 40% peracetic acid in 5 ml. of methanol. When the addition was complete the reaction mixture was evaporated to dryness in vacuo. The residue was dissolved in 45:5 ethyl acetate-methanol and absorbed on a column of silica gel. Following elution with ethyl acetate the product was eluted with 90:10 ethyl acetate-methanol. The material so-obtained was dissolved in ethyl acetate-methanol, the resulting solution acidified with glacial acetic acid and evaporated to dryness. The residue was taken up in 5 ml. of chloroform, the resulting solution cooled to −65° C. and diluted with ether. The resulting solid was dissolved in tetrahydrofuran, the solution acidified with glacial acetic acid and evaporated to dryness. The residue was dissolved in chloroform, the solution cooled to −65° C. and diluted with ether. The resulting solid was collected and dried affording 550 mg. of 4-hydroxy-α-<{[3-(4-methoxyphenyl)-1-methylpropyl]amino}methyl>-3-(methylsulfinyl)benzenemethanol acetate salt as a dextrorotatory pair of diastereomeric sulfoxides, $[\alpha]_D^{25} = +28.5°$.

F. A 5.0-gram sample of isomerically pure dextrorotatory 4-hydroxy-α-<{[3-(4-methoxyphenyl)-1-methylpropyl]-amino}methyl>-3-(methylthio)benzenemethanol acetate salt ($[\alpha]_D^{25} = +31.5°$) prepared according to the method of part C above oxidized as described in part E above. When oxidation was complete the reaction mixture was evaporated to dryness and the residue crystallized from ethyl acetate to give 4.2 g. of crystalline product, m.p. 107°–115° C., $[\alpha]_D^{25} = +28.2°$. A small sample was dissolved in acetone-methanol and the solution treated with cyclohexylsulfamic acid. The precipitated salt was collected to give, after drying, 4-hydroxy-α-<{[3-(4-methoxyphenyl)-1-methylpropyl]amino}methyl>-3-(methylsulfinyl)benzenemethanol cyclohexylsulfamate salt as a dextrorotatory pair of diastereomeric sulfoxides, m.p. 152°–154° C., $[\alpha]_D^{25} = +35.9°$.

The pair of diastereomeric sulfoxides of this example correspond to the products of Examples 10 and 12.

EXAMPLE 7

A. Following a procedure similar to that described in Example 2E but employing 128 g. (0.72 mole) of incompletely resolved (+)-3-(4-methoxyphenyl)-1-methylpropylamine, $[\alpha]_D^{25} = +4.4°$ (2% in water), and 120 g. (0.33 mole) of 2-bromo-4'-hydroxy-3'-(methylthio)acetophenone 4'-benzoate there was obtained a first crop of 82 g., m.p. 172°–174° C. and a second crop of 43 g., m.p. 171°–174° C. The crops were combined and a 16-gram sample was recrystallized from 95% ethanol to give 10 g. of incompletely resolved (+)-4'-hydroxy-2-{[3-(4-methoxyphenyl)-1-methylpropyl]amino}-3'-(methylthio)acetophenone 4'-benzoate hydrobromide, m.p. 174°–175° C., $[\alpha]_D^{25} = +8.4°$.

B. To a vigorously stirred solution containing 180 g. (1.0 mole) of (+)-3-(4-methoxyphenyl)-1-methylpropylamine [optical purity ≧97% as indicated by nmr spectroscopy in the presence of Eu(TFC)₃] and 55 ml. of triethylamine in 300 ml. of N,N-dimethylformamide at −60° C. there was added over 1.5 hours a solution containing 106 g. (0.384 mole) of 2-bromo-4'-hydroxy-3'-(methylthio)acetophenone 4'-benzoate in 500 ml. of N,N-dimethylformamide. Stirring was continued an additional 0.5 hour. The reaction mixture was acidified with 48% hydrogen bromide and extracted with methylene dichloride. The organic extracts were washed with water and concentrated to about 320 ml. The concentrate was diluted with 400 ml. of isopropyl acetate and cooled. The solid which precipitated was collected and dried to give 167 g. of optically pure (+)-4'-hydroxy-2-{[3-(4-methoxyphenyl)-1-methylpropyl]amino}-3'-(methylthio)acetophenone 4'-benzoate hydrobromide, m.p. 171°–173° C., $[\alpha]_D^{25} = +11.8°$. A 7.0-gram sample was recrystallized from aqueous methanol containing a small amount of HBr to give, after drying, 5.9 g., m.p. 175°–177° C., $[\alpha]_D^{25} = 11.6°$.

C. To a solution containing 106 g. (0.195 mole) of incompletely resolved (+)-4'hydroxy-2-{[3-(4-methoxyphenyl)-1-methylpropyl]amino}-3'-(methylthio)acetophenone 4'-benzoate hydrobromide prepared according to the procedure of part A in 700 ml. of methanol at 0° C. was added over 0.5 hour 6 g. (0.16 mole) of sodium borohydride. Stirring at 0° C. was continued an additional 0.5 hour. A 150-ml. aliquot of the reaction mixture was concentrated under reduced pressure below 50° C. The concentrate was dissolved in ether and the ethereal solution was washed thoroughly with water, dried over anhydrous magnesium sulfate and evaporated to dryness. The residue was dissolved in 75 ml. of isopropyl acetate and the resulting solution was acidified with acetic acid then diluted with ether until cloudy and stirred for 3 hours. The solid which precipitated was collected by filtration, washed with isopropyl acetate and ether and dried to give 6.4 g. of 4-hydroxy-α-<{[3-(4-methoxyphenyl)-1-methylpropyl]amino}methyl>-3-(methylthio)benzenemethanol 4-benzoate acetate salt, m.p. 107°–110° C.

D. To a solution containing 10.0 g. (0.0188 mole) of optically pure (+)-4'-hydroxy-2-{[3-(4-methoxyphenyl)-1-methylpropyl]amino}-3'-(methylthio)acetophenone 4'-benzoate hydrobromide (m.p. 171°–173° C., $[\alpha]_D^{25} = +11.8°$) in 100 ml. of methanol at 0° C. was added portionwise 380 mg. of sodium borohydride. Following the addition of several ml. of acetic acid, the mixture was evaporated to dryness. The residue was dissolved in a mixture of ethyl acetate and ether and the resulting solution was washed with saturated aqueous sodium bicarbonate, dried over anhydrous sodium sulfate, acidified with 2.5 ml. of acetic acid and evaporated to dryness. Recrystallization of the residue from isopropyl acetate-ether afforded 6 g. of 4-hydroxy-α-<{[3-(4-methoxyphenyl)-1-methylpropyl]amino}methyl>-3-(methylthio)benzenemethanol 4-benzoate acetate salt $[\alpha]_D^{25} = +6.4°$ as a dextrorotatory pair of diastereomeric benzenemethanols corresponding to the products of Example 9A and B. Another similar run afforded a product having m.p. 101°–102.5° C., $[\alpha]_D^{25} = +7.6°$.

E. To a stirred solution containing 8.0 g. (0.0147 mole) (+)-4'-hydroxy-2-{[3-(4-methoxyphenyl)-1-methylpropyl]amino}-3'-(methylthio)acetophenone 4'-benzoate hydrobromide $[\alpha]_D^{25} = +11.1°$ in 60 ml. of trifluoroacetic acid at 0° C. was added dropwise 3 ml. of commercial 40% peracetic acid. When the addition was complete the reaction mixture was evaporated to dryness. The residue was dissolved in benzene and the resulting solution was evaporated to dryness. The residual gum was dissolved in isopropyl acetate and acidified with ethanolic hydrogen chloride. The precipitated solid was collected and recrystallized from methanol-isopropyl acetate to give 6.0 g. of 4'-hydroxy-2-{[3-(3-bromo-4-methoxyphenyl)-1-methylpropyl]-amino}-3'-(methylsulfinyl)acetophenone 4'-benzoate hydrochloride, m.p. 165°–167° C.

The product obtained in this example was erroneously identified in parent application Ser. No. 699,856 as being 4'-hydroxy-2-{[3-(4-methoxyphenyl)-1-methylpropyl]amino}-3-(methylsulfinyl)acetophenone 4'-benzoate hydrochloride.

EXAMPLE 8

4-Hydroxy-α-<{[3-(4-methoxphenyl)-1-methylpropyl]amino}methyl>benzenemethanol 4-benzoate acetate salt (5.0 g., 0.0095 mole) prepared according to a procedure similar to that of Example 7D was oxidized with 1.5 ml. of commercial 40% peracetic acid following a procedure similar to that of Example 6E. When the oxidation was complete the reaction mixture was treated with 0.9 g. of sulfuric acid and cooled. The solid which precipitated was collected and dried to give 2.8 g. of 4-hydroxy-α-<{[3-(4-methoxyphenyl)-1-methylpropyl]amino}methyl>-3-(methylsulfinyl)benzenemethanol 4-benzoate hemi-sulfate, m.p. 193°–195° C.

EXAMPLE 9

A. To a solution containing 7.4 g. of the free base derived from dextrorotatory 4-hydroxy-α-<{[3-(4-methoxhphenyl)-1-methylpropyl]amino}methyl>-3-(methylthio)benzenemethanol 4-benzoate acetate salt, $[\alpha]_D^{25} = +6.4°$ in 60 ml. of isopropyl acetate was added a solution containing 1.8 g. of (+)-mandelic acid in 20 ml. of isopropyl acetate. The resulting solution was diluted with ether until slightly turbid and stirred two days at room temperature. The precipitate was collected and the mother liquors which were enriched in the levorotatory diastereomer were set aside for use in part B below. The collected solid was recrystallized eight times from methylene chloride-ether to give 3.3 g. of the (+)-mandelate salt, m.p. 126°–127° C., $[\alpha]_D^{25} = +49.1°$ which was subsequently converted to the acetate salt to give 2.1 g. of 4-hydroxy-α-<{[3-(4-methoxyphenyl)-1-methylpropyl]amino}methyl<-3-(methylthio)benzenemethanol 4-benzoate acetate salt, m.p. 88.5°–90° C., $[\alpha]_D^{25} = +26.7°$, corresponding to the dextrorotatory member of the pair of diastereomeric benzenemethanols present in the product of Example 7D.

B. The mother liquors from part A above were converted to the free base, dissolved in isopropyl acetate, treated with 1.5 g. of (−)-mandelic acid, and the solution diluted with ether. The precipitate was collected, recrystallized once from isopropyl acetate-ether to give 2.7 g. of the (−)-mandelate salt, m.p. 120°–120.5° C., $[\alpha]_D^{25} = -35.0°$ which was subsequently converted to 4-hydroxy-α-<{[3-(4-methoxyphenyl)-1-methylpropyl]amino}methyl>-3-(methylthio)benzenemethanol 4-benzoate acetate salt, m.p. 82°–83° C., $[\alpha]_D^{25} = -10.0°$, corresponding to the levorotatory member of the pair of diastereomeric benzenemethanols present in the product of Example 7D.

C. A mixture containing 600 mg. of 4-hydroxy-α-[3-(4-methoxyphenyl)-1-methylpropyl]amino methyl-3-(methylthio)benzenemethanol 4-benzoate acetate salt (m.p. 82°–83° C., $[\alpha]_D^{25} = -10.0°$, 5 ml. of 35% aqueous sodium hydroxide and several ml. of methanol was stirred 10 minutes at room temperature, then diluted with 20 ml. of water and stirred an additional 10 minutes in a warm-water bath. The pH was adjusted to 9 with acetic acid and the methanol was evaporated under reduced pressure. The residue was extracted with ethyl acetate, and after drying over anhydrous sodium sulfate the extracts were evaporated to dryness. The residue was dissolved in isopropyl acetate, the resulting solution acidified with acetic acid and cooled. The precipitated solid was collected by filtration and dried under vacuum to give 500 mg. of 4-hydroxy-α-<{[3-(4-methoxyphenyl)-1-methylpropyl]amino}methyl>-3-(methylthio)benzenemethanol acetate salt, m.p. 117°–120° C., $[\alpha]_D^{25} = -17.0°$ (average of two determinations) corresponding to the levorotatory member of the pair of diastereomeric benzenemethanols present in the product of Example 5C.

D. To a stirred solution containing 1.0 g. (0.003 mole) of 4-hydroxy-α-<{[3-(4-methoxyphenyl)-1-methylpropyl]amino}methyl>-3-(methylthio)benzenemethanol $[\alpha]_D^{25} = -5.0°$) prepared according to the method of Example 6B, in 15 ml. of methanol at 0° C. there was added dropwise over 0.5 hour a solution of 0.45 ml. of commercial 40% peracetic acid in 5 ml. of methanol. When the addition was complete the reaction mixture was evaporated to dryness in vacuo. The residue was diluted with 10 ml. of benzene, the resulting solution acidified with glacial acetic acid and evaporated to dryness. The residual gum was crystallized from tetrahydrofuran-ether and then recrystallized from ethyl acetate-2-propanol to give 1.05 g. of 4-hydroxy-α-<{[3-(4-methoxyphenyl)-1-methylpropyl]amino}methyl>-3-(methylsulfinyl)benzenemethanol acetate salt as a levorotatory pair of diastereomeric sulfoxides, m.p. 90°–95° C., $[\alpha]_D^{25} = -9.4°$.

E. When the above oxidation was carried out starting with isomerically pure levorotatory 4-hydroxy-α-<{[3-(4-methoxyphenyl)-1-methylpropyl]amino}methyl >-3-(methylthio)benzenemethanol acetate salt (m.p. 117°–120° C., $[\alpha]_D^{25} = -17.0°$) prepared according to the method of part C above the resulting pair of diastereomeric sulfoxides had $[\alpha]_D^{25} = -18.8°$ (determined on the reaction mixture).

The pair of diastereomeric sulfoxides of this example correspond to the products of Examples 11 and 13.

EXAMPLE 10

Mother liquors obtained in the preparation of several batches of 4-hydroxy-α-<{[3-(4-methoxyphenyl)-1-methylpropyl]amino{methyl>-3-(methylsulfinyl)benzenemethanol acetate salt according to a procedure similar to that described in Example 5E were combined and evaporated to dryness. The residual oil was triturated successively with ether and isopropyl acetate. The residue (90 g.) was dissolved in 300 ml. acetone and the resulting solution treated with 33 g. of cyclohexylsulfamic acid in 200 ml. of acetone. The precipitated cyclohexylsulfamate was collected and recrystallized five times from aqueous methanol to give 7.3 g of product which was combined with 7.4 g. of material obtained in previous runs and converted to the hydrochloride. Recrystallization of the latter from methanol-isopropyl alcohol afforded 6.3 g. of 4-hydroxy-α-<{[3-(4-methoxyphenyl)-1-methylpropyl]amino}methyl>-3-(methylsulfinyl)benzenemethanol hydrochloride, m.p.

206°-207° C., $[\alpha]_D^{25} = +126.6°$, corresponding to the dextrorotatory member of the pair of diastereomeric sulfoxides present in the product of Example 6F.

EXAMPLE 11

The mother liquors resulting from the fractional crystallization of the product of Example 10 were evaporated and the residue crystallized from acetone. The resulting 12.4 g. of solid was recrystallized twice from methanol-acetone to give 5.1 g. of product $[\alpha]_D^{25} = +49.3°$. The latter material was combined with 3.5 g. obtained in a previous run and converted to the hydrochloride which was crystallized from 2-propanol to give 4-hydroxy-α-<{[3-(4-methoxyphenyl)-1-methylpropyl]amino}methyl>-3-(methylsulfinyl)benzenemethanol hydrochloride, m.p. 204°-205° C., $[\alpha]_D^{25} = +70.5°$, corresponding to the dextrorotatory member of the diastereomeric pair of sulfoxides present in the product of Example 9E.

EXAMPLE 12

The reaction mixture resulting from the oxidation of 12.1 g. of dextrorotatory 4-hydroxy-α-<{[3-(4-methoxyphenyl)-1-methylpropyl]amino}methyl>-3-(methylthio)benzenemethanol (+)-mandelate salt according to the procedure of Example 6F was evaporated to dryness, the residue dissolved in a mixture of 70 ml. of methanol and 15 ml. of water, treated with a molar equivalent of cyclohexylsulfamic acid and seeded wth the cyclohexylsulfamate salt of the product of Example 10. The 7.9 g. of product which crystallized was collected and set aside. The mother liquors were evaporated to dryness and the residue crystallized from acetone-methanol. The product was converted to 1.1 g. of the hydrochloride and combined with an additional 850 mg. obtained from the mother liquors resulting from the fractional crystallization of the diastereomer of Example 11. The combined solids were recrystallized from 2-propanol to give 1.4 g. of 4-hydroxy-α-<{[3-(4-methoxyphenyl)-1-methylpropyl]amino}methyl>-3-(methylsulfinyl)benzenemethanol hydrochloride, m.p. 138°-140° C., $[\alpha]_D^{25} = -48.2°$, corresponding to the levorotatory member of the pair of diastereomeric sulfoxides present in the product of Example 6F.

EXAMPLE 13

A. The reaction mixture resulting from the oxidation of 3 g. of levorotatory 4-hydroxy-α-<{[3-(4-methoxyphenyl)-1-methylpropyl]amino}methyl>-3-(methylthio)benzenemethanol acetate salt according to the procedure of Example 9E was evaporated to dryness, the residue dissolved in a 90:10 mixture of acetone-methanol, treated with a molar equivalent of cyclohexylsulfamic acid, and seeded with the cyclohexylsulfamate salt of the product of Example 11. The 1.6 g. of product which crystallized was collected and set aside. The mother liquors were evaporated to dryness and the residue crystallized twice from aqueous methanol to give 1.85 g. of crystalline solid, $[\alpha]_D^{25} = -67.5°$.

B. Alternatively, 10.0 g. of 4-hydroxy-α-<{[3-(4-methoxyphenyl)-1-methylpropyl]amino}methyl>-3-(methylthio)benzenemethanol 4-p-toluenesulfonate (+)-mandelate salt prepared according to the procedure of Example 6D was oxidized following a procedure similar to that of Example 9D and the product was isolated as the free base to give 10 g. of crude 4-hydroxy-α-<{[3-(4-methoxphenyl)-1-methylpropyl]amino}methyl>-3-(methylsulfinyl)benzenemethanol 4-p-toluenesulfonate as a pair of diastereomeric sulfoxides.

A solution containing the latter product and 15 ml. of 10% aqueous potassium hydroxide in 100 ml. of ethanol was stirred 1.5 hours at 45° C. The reaction mixture was then concentrated, diluted with saturated aqueous sodium bicarbonate and extracted with chloroform. The organic extracts were dried over anhydrous sodium sulfate and evaporated to dryness. The residue was dissolved in acetone and treated with a molar equivalent of cyclohexylsulfamic acid. The product which precipitated and collected, and recrystallized from acetone-methanol to give 1.15 g. of salt corresponding to the cyclohexylsulfamate salt of the product of Example 11. The mother liquors were evaporated to dryness and the residue crystallized from acetone. Four recrystallizations from aqueous methanol afforded 450 mg. of crystalline solid $[\alpha]_D^{25} = -66.2°$.

C. The levorotatory product of parts A and B were combined, recrystallized once from aqueous methanol and then converted to the hydrochloride to give 1.1 g. of 4-hydroxy-α-<{[3-(4-methoxyphenyl)-1-methylpropyl]amino}methyl>-3-(methylsulfinyl)benzenemethanol hydrochloride, m.p. 178°-180° C., $[\alpha]_D^{25} = -102.3°$, corresponding to the levorotatory member of the pair of diastereomeric sulfoxides present in the product of Example 9E.

EXAMPLE 14

A. To a stirred solution containing 20 g. (0.134 mole) of 1,1-dimethyl-2-phenylethylamine in 40 ml. of N,N-dimethylformamide at −50° C. was added dropwise over 15 minutes a solution containing 14.5 g. (0.048 mole) of 2-bromo-4'-hydroxy-3'-(methylthio)acetophenone 4'-acetate in 35 ml. of N,N-dimethylformamide. After the addition was complete stirring was continued an additional 1.25 hours. The reaction mixture was then treated with 3.5 ml. of 12N hydrochloric acid, diluted with 100 ml. of water and extracted thoroughly with ether. The ethereal extracts were dried over anhydrous sodium sulfate, acidified with ethanolic hydrogen chloride and cooled in a refrigerator overnight. The 12.5 g. of precipitated product was collected and combined with 6.0 g. of product obtained from a previous run and recrystallized twice from chloroform-methanol affording 15 g. of 2-[(1,1-dimethyl-2-phenylethyl)amino]-4'-hydroxy-3'-(methylthio)acetophenone 4'-acetate hydrochloride, m.p. 205° C. (dec.).

B. To a stirred suspension of 15 g. (0.037 mole) of 2-[(1,1-dimethyl-2-phenylethyl)amino]-4'-hydroxy-3'-(methylthio)acetophenone 4'-acetate hydrochloride in 200 ml. of methanol at −5° C. was added portionwise over 10 minutes 750 mg. (0.020 mole) of sodium borohydride. After stirring an additional 10 minutes the reaction mixture was brought to pH 7 with glacial acetic acid and evaporated to dryness. The residue was dissolved in ether-ethyl acetate and the resulting solution washed with saturated aqueous sodium bicarbonate. The organic layer was dried over anhydrous sodium sulfate, acidified with methanesulfonic acid and concentrated to a small volume. The concentrate was diluted with benzene and evaporated to dryness. The proces was then repeated employing toluene. The resulting solid residue was recrystallized from ethanol-ether to give 12 g. of α-{[(1,1-dimethyl-2-phenylethyl)amino]methyl}-4-hydroxy-3-(methylthio)benzenemethanol 4-acetate methanesulfonate, m.p. 112°-115° C.

C. A solution containing 9.5 g. (0.020 mole) of α-{[(1,1-dimethyl-2-phenylethyl)amino]methyl}-4-hydroxy-3-(methylthio)benzenemethanol 4-acetate methanesulfonate, 3 g. (0.045 mole) of potassium hydroxide and 20 ml. of water in 200 ml. of 95% ethanol was stirred overnight under nitrogen. The reaction mixture was neutralized and glacial acetic acid and concentrated to a small volume. The concentrate was diluted with saturated aqueous sodium bicarbonate and extracted with ethyl acetate. The organic extracts were dried over anhydrous sodium sulfate and concentrated to a volume of 100 ml. The concentrated solution was brought to a pale yellow color by dropwise addition of glacial acetic acid whereupon crystallization began. The product was collected by filtration and recrystallized from chloroform-methanol to give 5.1 g. of α-{[(1,1-dimethyl-2-phenylethyl)amino]methyl}-4-hydroxy-3-(methylthio)benzenemethanol acetate salt, m.p. 165°–167° C.

D. To a stirred solution containing 4.7 g. (0.012 mole) of α-{[(1,1-dimethyl-2-phenylethyl)amino]methyl}-4-hydroxy-3-(methylthio)benzenemethanol acetate salt in 100 ml. of methanol at 0° C. was added dropwise over 0.5 hours a solution containing 2 ml. (0.012 mole) of commercial 40% peracetic acid in 10 ml. of methanol. After the addition was complete the reaction mixture was evaporated to dryness and the residue was crystalized from ethanol-ether to give 4.3 g. of α-{[(1,1-dimethyl-2-phenylethyl)amino]methyl}-4-hydroxy-3-(methylsulfinyl)benzenemethanol acetate salt which softened at 100° C. and melted at 138°–140° C.

EXAMPLE 15

A. To a stirred solution containing 35 g. (0.25 mole) of o-(methylthio)phenol and 27.6 g. (0.30 mole) of propionyl chloride in 100 ml. of nitrobenzene there was added portionwise over 25 minutes 46.5 g. (0.35 mole) of aluminum chloride. The reaction was exothermic and the temperature rose to 45°–50° C. When the addition was complete the reaction mixture was stirred 2 hours at 60° C. and 1 hour at 70° C. The reaction mixture was cooled, diluted with water and extracted with ether. The ethereal extracts were dried over anhydrous sodium sulfate and evaporated to dryness in vacuo. The residual oil was adsorbed on a column of silica gel and continuously eluted with boiling methylene chloride. The eluate was evaporated to dryness and the residue recrystallized from ether giving 25 g. of crystalline product which was then triturated with ether at −65° C. to give 17 g. of pure 4'-hydroxy-3'-(methylthio)propiophenone.

B. To a stirred solution containing 17.4 g. (0.089 mole) of 4'-hydroxy-3'-(methylthio)propiophenone and 13 ml. (0.090 mole) of triethylamine in 200 ml. of methylene chloride there was added dropwise over 0.5 hour 7.65 g. (0.098 mole) of acetyl chloride. After the addition was complete stirring was continued an additional 2 hours. The reaction mixture was then washed successively with 3N hydrochloric acid and water and evaporated to dryness. The residual oil was dissolved in ether, treated with decolorizing carbon and filtered through a bed of silica gel. The filtrate was evaporated to dryness affording 21.4 g. of 4'-hydroxy-3'-(methylthio)propiophenone 4'-acetate as a pale yellow oil.

C. To a stirred solution containing 21.4 g. (0.088 mole) of 4'-hydroxy-3'-(methylthio)propiophenone 4'-acetate in 250 ml. of chloroform was added a solution containing 14.4 g. (0.090 mole) of bromine in 40 ml. of chloroform. After a 15-minute induction period the bromide began to be consumed. After 1 hour the reaction mixture was washed with 5% aqueous sodium bicarbonate and then water. The chloroform solution was dried over anhydrous sodium sulfate and evaporated to dryness to give 19 g. of 2-bromo-4'-hydroxy-3'-(methylthio)propiophenone 4'-acetate.

D. To a stirred solution containing 30 g. (0.185 mole) of 2-(4-methoxyphenyl)-1-methylethylamine in 150 ml. of N,N-dimethylformamide there was added dropwise 19.6 g. (0.062 mole) of 2-bromo-4'-hydroxy-3'-(methylthio)propiophenone 4'-acetate. After the addition was complete stirring was continued an additional 2 hours. The reaction mixture was then diluted with chloroform and washed successively with water, dilute hydrochloric acid and saturated aqueous sodium bicarbonate. The chloroform solution was dried over anhydrous sodium sulfate and evaporated to dryness. The residue was dissolved in ether, acidified with glacial acetic acid and cooled. The precipitated product was collected and triturated with chloroform to give 6.35 g. of 4'-hydroxy-2-{[2-(4-methoxyphenyl)-1-methylethyl]amino}-3'-(methylthio)propiophenone acetate salt, m.p. 110°–112° C.

E. To a stirred solution containing 6.2 g. (0.0148 mole) of 4'-hydroxy-2-{[2-(4-methoxyphenyl)-1-methylethyl]amino}-3'-(methylthio)propiophenone acetate salt in 100 ml. of methanol at 0° C. there was added portionwise 0.5 g. of sodium borohydride. After the addition was complete stirring was continued an additional 0.5 hour. The reaction mixture was then acidified with glacial acetic acid and evaporated to dryness. The residue was diluted with saturated aqueous sodium bicarbonate and extracted with ethyl acetate. The organic extracts were evaporated to dryness and the residue dissolved in ether. The ethereal solution was acidified with glacial acetic acid and cooled. The precipitated product was collected and dried to give 5.0 g. of 4-hydroxy-α-<{[2-(4-methoxyphenyl)-1-methylethyl]amino}ethyl>-3-(methylthio)benzenemethanol acetate salt, m.p. 160°–162° C.

F. To a stirred mixture of 2.35 g. (0.0056 mole) of 4-hydroxy-α-<{[2-(4-methoxyphenyl)-1-methylethyl]amino}ethyl>-3-(methylthio)benzenemethanol acetate salt and 40 ml. of methanol at −10° C. there was added dropwise a solution containing 1 ml. (0.0056 mole) of commercial 40% peracetic acid in 5 ml. of methanol. After the addition was complete stirring was continued an additional 0.5 hour. The reaction mixture was then evaporated to dryness and the residual oil suspended in chloroform and diluted with ether producing a granular solid which was collected and dried to give 2.2 g. of 4-hydroxy-α-<{1-[2-(4-methoxyphenyl)-1-methylethyl]amino}ethyl>-3-(methylsulfinyl)benzenemethanol acetate salt, m.p. 110° C.

EXAMPLE 16

A. To a stirred solution containing 16 g. (0.082 mole) of 2-(3,4-dimethoxyphenyl)-1-methylethylamine and 6 ml. (0.041 mole) of triethylamine in 60 ml. of N,N-dimethylformamide at −65° C. there was added dropwise over 0.75 hour a solution containing 12.5 g. (0.041 mole) of 2bromo-4'-hydroxy-3'-(methylthio)acetophenone 4'-acetate in 40 ml. of N,N-dimethylformamide. After the addition was complete stirring was continued an additional hour. The reaction mixture was then made slightly acidic with 5 ml. of 12N hydrochloric acid and extracted with chloroform. The organic extracts were evaporated to dryness and the residue was dissolved in trifluoroacetic acid and treated with excess acetyl chloride. After stirring 1 hour the mixture was diluted with water and evaporated to dryness. The residue was partitioned between ethyl acetate and saturated aqueous sodium bicarbonate. The organic layer was dried over anhydrous sodium sulfate and evaporated to dryness to give 12 g. of crude 2-{[2-(3,4-dimethoxyphenyl)-1-methylethyl]amino}-4'-hydroxy-3'-(methylthio)acetophenone 4'-acetate.

B. Following a procedure similar to that described in Example 2B but using 12 g. of 2-{[2-(3,4-dimethoxyphenyl)-1-methylethyl]amino}-4'-hydroxy-3'-(methylthio)acetophenone 4'-acetate, 870 mg. of sodium borohydride and 1.4 g. of potassium hydroxide there was obtained 2.2 g. of α-<{[2-(3,4-dimethoxyphenyl)-1-methylethyl]amino}methyl <-4-hydroxy-3-(methylthio)benzenemethanol acetate salt, m.p. 141°–144° C.

C. Following a procedure similar to that described in Example 15F but using 2.30 g. (0.0052 mole) of α-<{[2-(3,4-dimethoxyphenyl)-1-methylethyl]amino}methyl>-4-hydroxy-3-(methylthio)benzenemethanol acetate salt and 0.95 ml. (0.0052 mole) of commercial 40% peracetic acid there was obtained 1.9 g. of α-<{[2-(3,4-dimethoxyphenyl)-1-methylethyl]amino}methyl>-4-hydroxy-3-(methylsulfinyl)benzenemethanol acetate salt as a light-yellow amorphous solid.

EXAMPLE 17

A. To a stirred solution containing 19.5 g. (0.12 mole) of 1,1-dimethyl-3-phenylpropylamine in 100 ml. of N,N-dimethylformamide under nitrogen at −60° C. there was added dropwise over 0.5 hour a solution containing 12 g. (0.04 mole) of 2-bromo-4'-hydroxy-3'-(methylthio)acetophenone 4'-acetate in 40 ml. of N,N-dimethylformamide. After the addition was complete stirring was continued 1 hr. at −35° C. The reaction was then acidified with 10 ml. of 12N hydrochloric acid, diluted with 150 ml. of chloroform and the resulting solution washed with water. The chloroform solution was cooled to −65° C. and diluted with ether. The resulting precipitate was collected and recrystallised from ethanol to give 12 g. of 2-[(1,1-dimethyl-3-phenylpropyl)amino]-4'-hydroxy-3'-(methylthio)acetophenone 4'-acetate hydrochloride, m.p. 188°–193° C.

B. Following a procedure similar to that described in Example 2B but using 11.0 g. (0.026 mole) of 2-[(1,1-dimethyl-3-phenylpropyl)amino]-4'-hydroxy-3'-(methylthio)acetophenone 4'-acetate hydrochloride, 750 mg. (0.02 mole) of sodium borohydride and 1.4 g. (0.026 mole) of potassium hydroxide there was obtained 9.2 g. of α-{[(1,1-dimethyl-3-phenylpropyl)amino]methyl}-4-hydroxy-3-(methylthio)benzenemethanol acetate salt, m.p. 171°–172° C.

C. Following a procedure similar to that described in Example 2G but using 6.2 g. (0.015 mole) of α-{[(1,1-dimethyl-3-phenylpropyl)amino]methyl}-4-hydroxy-3-(methylthio)benzenemethanol acetate salt and 1.17 g. (0.015 mole) of commercial 40% peracetic acid there was obtained 5.5 g. of crude α-{[(1,1-dimethyl-3-phenylpropyl)amino]methyl}-4-hydroxy-3-(methylsulfinyl)benzenemethanol acetate salt. Following recrystallization twice from chloroform-methanol and once from ethyl acetate-acetone-ethanol the product was dissolved in ethyl acetate-methanol and the resulting solution acidified with glacial acetic acid and evaporated to dryness. Recrystallization of the residue from ethanol-ethyl acetate afforded 1.4 g. of analytically pure material, m.p. 155°–157° C.

EXAMPLE 18

A. To a stirred solution containing 65 g. (1.0 mole) of potassium cyanide and 73.7 g. (0.38 mole) of 4-(p-methoxyphenyl)-2-methyl-2-butanol in 300 ml. of n-butyl ether at 60° C. there was added dropwise over 1 hour 120 ml. of concentrated sulfuric acid. When the addition was complete stirring was continued an additional hour at 50°–55° C. The reaction mixture was then poured over 1200 g. of ice, made basic with sodium carbonate and extracted with ether. The ethereal extracts were dried over anhydrous sodium sulfate and evaporated to dryness. The 76.5 g. of residual oil was heated under reflux 3 hours in 175 ml. of 12N hydrochloric acid. The mixture was cooled, washed with ether, made basic with 35% aqueous sodium hydroxide and extracted with ether. The ethereal extracts were dried over anhydrous sodium sulfate and evaporated to dryness. The residual oil was distilled under reduced pressure and the fraction boiling at 161°–162° C./22 mm. was collected affording 35 g. of 1,1-dimethyl-3-(4-methoxyphenyl)propylamine.

B. Following a procedure similar to that described in Example2A but using 29 g. (0.15 mole) of 1,1-dimethyl-3-(4-methoxyphenyl)propylamine, 15 g. (0.05 mole) of 2-bromo-4'-hydroxy-3'-(methylthio)acetophenone 4'-acetate and 10 ml. of acetyl chloride there was obtained 9.5 g. of 2-{[1,1-dimethyl-3-(4-methoxyphenyl)propyl]amino}-4'-hydroxy-3'-(methylthio)acetophenone 4'-acetate hydrochloride m.p. 186°–190° C.

C. Following a procedure similar to that described in Example 2B but using 9.5 g. (0.021 mole) of 2-{[1,1-dimethyl-3-(4-methoxyphenyl)propyl]amino}-4'-hydroxy-3'-(methylthio)acetophenone 4'-acetate hydrochloride, 600 mg. (0.015 mole) of sodium borohydride and 1.2 g. of potassium hydroxide there was obtained 2.3 g. of α-<{[1,1-dimethyl-3-(4-methoxyphenyl)propyl]amino}methyl>-4-hydroxy-3-(methylthio)benzenemethanol acetate salt, m.p. 173°–174° C.

D. Following a procedure similar to that described in Example 2G but using 3.9 g. (0.009 mole) of α-<{[1,1-dimethyl-3-(4-methoxyphenyl)propyl]amino}methyl>-4-hydroxy-3-(methylthio)benzenemethanol acetate salt and 680 mg. of commercial 40% peracetic acid there was obtained 3.0 g. of α-<{[1,1-dimethyl-3-(4-methoxyphenyl)propyl]amino}methyl>-4-hydroxy-3-(methylsulfinyl)benzenemethanol acetate salt, m.p. 115° C.

EXAMPLE 19

A. Following a procedure similar to that described in Example 2A but using 18 g. (0.12 mole) of 1-methyl-3-phenylpropylamine, 12 g. (0.04 mole) of 2-bromo-4'-hydroxy-3'-(methylthio)acetophenone 4'-acetate and 8 ml. of acetyl chloride there was obtained 8.3 g. of 4'-hydroxy-2-[(1-methyl-3-phenylpropyl)amino]-3'-(methylthio)acetophenone 4'-acetate hydrochloride.

B. Following a procedure similar to that described in Example 2B but using 8.1 g. (0.02 mole) of 4'-hydroxy-2-[(1-methyl-3-phenylpropyl)amino]-3'-(methylthio)acetophenone 4'-acetate hydrochloride, 500 mg. of sodium borohydride and 1.2 g. of potassium hydroxide there was obtained 6.2 g. of 4-hydroxy-α-{[(1-methyl-3-phenylpropyl)amino]methyl}-3-methylthio)benzenemethanol acetate salt, m.p. 140°–142° C.

C. Following a procedure similar to that described in Example 2G but using 4.2 g. (0.011 mole) of 4-hydroxyy-α-{[(1-methyl-3-phenylpropyl)amino]methyl}-3-(methylthio)benzenemethanol acetate salt and 815 mg. (0.011 mole) of commercial 40% peracetic acid there was obtained 4.0 g. of 4-hydroxy-α-{[(1-methyl-3-phenylpropyl)amino]methyl}-3-(methylsulfinyl)benzenemethanol acetate salt as a pale yellow amorphous solid.

EXAMPLE 20

A. Following a procedure similar to that described in Example 14A but using 18.2 g. (0.11 mole) of 3-(4-methoxyphenyl)propylamine and 11.2 g. (0.037 mole) of 2-bromo-4'-hydroxy-3'-(methylthio)acetophenone 4'-acetate there was obtained 9 g. of crude 4'-hydroxy-2-{[3-(4-methoxy phenyl)propyl]amino}-3'-(methylthio)acetophenone 4'-acetate hydrochloride which was suitable for use in the next step.

B. Following a procedure similar to that described in Example 2B but using 9 g. of crude 4'-hydroxy-2-{[3-(4-methoxyphenyl)propyl]amino}-3'-(methylthio)acetophenone 4'-acetate hydrochloride, 600 mg. of sodium borohydride and 2.0 g. of potassium hydroxide there was obtained 1.2 g. of 4-hydroxy-α-<{[3-(4-methoxyphenyl)propyl]amino}methyl>-3-(methylthio)benzenemethanol acetate salt, m.p. 123°–125° C.

C. Following a procedure similar to that described in Example 2G but using 1.2 g. (0.003 mole) of 4-hydroxy-α-<{[3-(4-methoxyphenyl)propyl]amino}methyl>-3-(methylthio)benzenemethanol acetate salt and 0.44 ml. (0.003 mole) of commercial 40% peracetic acid there was obtained 1.1 g. of 4-hydroxy-α-<{[3-(4-methoxyphenyl)propyl]amino}methyl>-3-(methylsulfinyl)benzenemethanol acetate salt as an amorphous tan solid.

EXAMPLE 21

A. A stirred mixture containing 64 g. (0.334 mole) of 5-(4-methoxyphenyl)-2-pentanone, 80 g. (1.77 moles) of formamide and 6 ml. of formic acid was slowly heated to 165° C. and treated dropwise over 3.5 hours with 50 ml. of formic acid while the water formed during the reaction was allowed to distill slowly. Stirring at 165° C. was continued an additional 3 hours. The reaction mixture was then cooled, diluted with 1 liter of ice and water and extracted with a mixture of ether and benzene. The organic extracts were evaporated and the residual oil was heated under reflux 1.5 hours in 130 ml. of 12N hydrochloric acid. The mixture was cooled, diluted with 300 ml. of water and washed with a mixture of ether and benzene. The aqueous layer was made basic with 35% aqueous sodium hydroxide and extracted with a mixture of ether and benzene. The organic layer was extracted with 1N hydrochloric acid, and the acidic aqueous layer was made basic with 35% aqueous sodium hydroxide and extracted with an etherbenzene mixture. The extracts were dried over anhydrous sodium sulfate and the solvent evaporated in vacuo. The residual oil was distilled under reduced pressure to give 37 g. of 4-(4-methoxyphenyl)-1-methylbutylamine, b.p. 163°–166.5° C./18 mm.

B. To a stirred solution containing 15.5 g. (0.08 mole) of 4-(4-methoxyphenyl)-1-methylbutylamine in 80 ml. of N,N-dimethylformamide at −60° C. there was added dropwise over 0.75 hour a solution containing 8.0 g. (0.027 mole) of 2-bromo-4'-hydroxy-3'-(methylthio)acetophenone 4'-acetate in 25 ml. of N,N-dimethylformamide. After the addition was complete stirring at −60° to −45° C. was continued an additional hour. The reaction mixture was then acidified with 48% hydrobromic acid and extracted with chloroform. The chloroform solution was diluted with 2.5 volumes of ether and cooled to −65° C. The resulting precipitate was collected, redissolved in chloroform and the resulting solution washed thoroughly with water. The chloroform solution was then dried over anhydrous sodium sulfate and evaporated to dryness to give 9 g. of crude 4'-hydroxy-2-{[4-(4-methoxyphenyl)-1-methylbutyl]amino}-3'-(methylthio)acetophenone 4'-acetate hydrobromide.

C. Following a procedure similar to that described in Example 2B but using 9 g. of crude 4'-hydroxy-2-{[4-(4-methoxyphenyl)-1-methylbutyl]amino}-3'-(methylthio)acetophenone 4'-acetate hydrobromide, 500 mg. of sodium borohydride and 1 g. of potassium hydroxide there was obtained 5.5 g. of 4-hydroxy-α-<{[4-(4-methoxyphenyl)-1-methylbutyl]amino}methyl>-3-(methylthio)benzenemethanol acetate salt, m.p. 155°–157° C.

D. Following a procedure similar to that described in Example 2G but using 3.0 g. (0.007 mole) of 4-hydroxy-α-<{[4-(4-methoxyphenyl)-1-methylbutyl]amino}methyl>-3-(methylthio)benzenemethanol acetate salt and 1.04 ml. (0.007 mole) of commercial 40% peracetic acid there was obtained 2.6 g. of 4-hydroxy-α-<{[4-(4-methoxyphenyl)-1-methylbutyl]amino}methyl>-3-(methylsulfinyl)benzenemethanol acetate salt as an amorphous yellow solid.

EXAMPLE 22

A. To a stirred mixture of 52.5 g. (0.253 mole) of 4-(4-methoxyphenyl)-1,1-dimethylbutyl alcohol, and 44.5 g. (0.685 mole) of powdered potassium cyanide in 200 ml. of n-butyl ether at 60° C. was added dropwise over 1 hour 80 ml. of concentrated sulfuric acid. The temperature was maintaind at 60°–65° C. throughout the addition and stirring was continued at 50°–55° C. an additional hour after the addition was complete. The reaction mixture was then poured into 850 ml. of ice, made basic with 35% aqueous sodium hydroxide and extracted with ether. The ethereal extracts were evaporated to dryness and the residual oil heated under reflux 3 hours in 125 ml. of 12N hydrochloric acid. The resulting mixture was diluted with 300 ml. of water and washed with a mixture of ether and benzene. The aqueous layer was made basic with 35% aqueous sodium hydroxide and extracted with a mixture of ether and benzene. The organic layer was then extracted with 1N hydrochloric acid, the acidic aqueous layer made basic with 35% aqueous sodium hydroxide and extracted with an etherbenzene mixture. The extracts were dried over anhydrous sodium sulfate and evaporated to dryness in vacuo affording 12.2 g. of 4-(4-methoxyphenyl)-1,1-dimethylbutylamine as a straw-colored oil.

B. Following a procedure similar to that described in Example 21B but using 19 g. (0.09 mole) of 4-(4-methoxyphenyl)-1,1-dimethylbutylamine and 10.0 g. (0.033 mole) of 2-bromo-4'-hydroxy-3'-(methylthio)acetophenone 4'-acetate and allowing the final product to crystallize from acetone in a refrigerator overnight, there was obtained 10.5 g. of crystalline 4'-hydroxy-2-{[4-(4-methoxyphenyl)-1,1-dimethylbutyl]amino}-3'-(methylthio)acetophenone 4'-acetate hydrobromide, m.p. 180°–181° C.

C. Following a procedure similar to that described in Examples 2B but using 10.5 g. (0.021 mole) of 4'i-hydroxy-2-{[4-(4-methoxyphenyl)-1,1-dimethylbutyl]amino}-3'-(methylthio)acetophenone 4'-acetate hydrobromide, 250 mg. of sodium borohydride and 1 g. of potassium hydroxide, and recrystallizing the product from methanol-ether there was obtained 4 g. of 4-hydroxy-α-<{[4-(4-methoxyphenyl)-1,1-dimethylbutyl]amino}-methyl>-3-(methylthio)benzenemethanol as the free base m.p. 179°–180° C.

D. Following a procedure similar to that described in Example 15F but employing 2.7 g. (0.007 mole) of 4-hydroxy-α-<{[4-(4-methoxyphenyl)-1,1-dimethylbutyl]amino}methyl>-3-(methylthio)benzenemethanol there was obtained 1.8 g. of 4-hydroxy-α-<{[4-(4-methoxyphenyl)-1,1-dimethylbutyl]amino}methyl>-3-(methylsulfinyl)benzenemethanol as an amorphous white powder.

EXAMPLE 23

A. A stirred mixture containing 7.4 g. (0.015 mole) of optically pure (+)-4'-hydroxy-2-{[3-(4-methoxyphenyl)-1-methylpropyl]amino}-3'-(methylthio)acetophenone 4'-benzoate hydrobromide and 100 ml. of 48% hydrobromic acid was heated under reflux 1.5 hours. The reaction mixture was then evaporated to dryness and the residue triturated with ethanol and isopropyl acetate to give 5.3 g. of (+)-4'-hydroxy-2-{[3-(4-hydroxyphenyl)-1-methylpropyl]amino}-3'-(methylthio)acetophenone hydrobromide.

B. Following a procedure similar to that described in Example 15E but employing 5.0 g. (0.012 mole) of (+)-4'-hydroxy-2-{[3-(4-hydroxyphenyl)-1-methylpropyl]amino}-3'-(methylthio)acetophenone hydrobromide and 0.455 g. of sodium borohydride, there was obtained 4.2 g. of 4-hydroxy-α-<{[3-(4-hydroxyphenyl)-1-methylpropyl]amino}methyl>-3-(methylthio)benzenemethanol acetate salt, $[\alpha]_D^{25} = +5°$.

C. Following a procedure similar to that described in Example 6E but employing 4.2 g. (0.01 mole) of crude 4-hydroxy-α-<{[3-(4-hydroxyphenyl)-1-methylpropyl]amino}methyl>-3-(methylthio)benzenemethanol acetate salt and eluting the oxidation product from a short (1.5 m.) column of silica gel followed by conversion to the cyclohexylsulfamate salt afforded 2.3 g. of dextrorotatory 4-hydroxy-α-<{[4-(hydroxyphenyl)-1-methylpropyl]amino}methyl>-3-(methylsulfinyl)benzenemethanol cyclohexylsulfamate salt, m.p. 149°–151° C., $[\alpha]_D^{25} = +2.1°$.

EXAMPLE 24

A. Following a procedure similar to that described in Example 7B but employing 25 g. of 2-bromo-4'-hydroxy-3'-(methylthio)acetophenone 4'-benzoate and 32 g. of (−)-3-(4-methoxyphenyl)-1-methylpropylamine (optical purity≧94%), there was obtained 29.6 g. of (−)-4'-hydroxy-2-{[3-(4-methoxyphenyl)-1-methylpropyl]amino}-3'-(methylthio)acetophenone 4'-benzoate hydrobromide.

B. Following a procedure similar to that described in Example 2F but employing 29.6 g. (0.055 mole) of (−)-4'-hydroxy-2-{[3-(4-methoxyphenyl)-1-methylpropyl]amino}-3'-(methylthio)acetophenone 4'-benzoate hydrobromide, 1.55 g. (0.041 mole) of sodium borohydride and 30 ml. of 35 percent aqueous sodium hydroxide; and isolating the product as the hydrochloride salt there was obtained 18.6 g. of 4-hydroxy-α-<{[3-(4-methoxyphenyl)-1-methylpropyl]amino}methyl>-3-(methylthio)benzenemethanol hydrochloride.

C. Following a procedure similar to that described in Example 2G but employing 17.6 g. (0.044 mole) of 4-hydroxy-2-<{[3-(4-methoxyphenyl)-1-methylpropyl]amino}methyl>-3-(methylthio)benzenemethanol hydrochloride prepared according to the method of Example 24B and 3.36 g. (0.044 mole) of commercial 50% peracetic acid, there was obtained 12.5 g. of 4-hydroxy-2-<{[3-(4-methoxyphenyl)-1-methylpropyl]amino}methyl>-3-(methylsulfinyl)benzenemethanol hydrochloride, m.p. 107°–117° C., $[\alpha]_D^{25} = +7.6°$, as a mixture of four diastereome

EXAMPLE 25

A chloroform solution containing 10 g. (0.0185 mole) of (+)-4'-hydroxy-2-{[3-(4-methoxyphenyl)-1-methylpropyl]amino}3'-(methylthio)acetophenone 4'-benzoate hydrobromide was washed thoroughly with saturated aqueous sodium bicarbonate. The chloroform solution was then acidified with acetic acid and evaporated to dryness. The residue was oxidized with 2.2 ml. of commercial 50% peracetic acid in trifluoroacetic acid according to the method described in Example 7E to give 6.4 g. of 4'-hydroxy-2-{[3-(4-methoxyphenyl)-1-methylpropyl]amino}-(methylsulfinyl)acetophenone 4'-benzoate hydrochloride as a mixture of diastereomeric sulfoxides, m.p. 158°–159° C.

EXAMPLE 26

A. A mixture containing 15 g. of (+)-4'-hydroxy-2-{[3-(4-methoxyphenyl)-1-methylpropyl]amino}-3'-(methylthio)acetophenone 4'-benzoate hydrobromide, 140 ml. of acetonitrile and 40 ml. of concentrated aqueous ammonia was stirred 5 minutes whereupon a solid began to precipitate. The mixture was cooled to 0° C. and the precipitated product was collected and washed with ether. Drying at 60° C. caused the product to turn to a black gum. The latter was dissolved in methanol-ethyl acetate and filtered through silica gel. The filtrate was evaporated to dryness and the residue was dissolved in ethyl acetate. Acidification of the resulting solution with ethanolic hydrogen chloride afforded 2.5 g. of pale yellow crystalline (+)-4'-hydroxy-2-{[3-(4-methoxyphenyl)-1-methylpropyl]-amino}-3'-(methylthio)acetophenone hydrochloride.

B. Following a procedure similar to that described in Example 7E but employing 2.46 ml. (0.016 mole) of commercial 50% peracetic acid and 5.7 g. (0.016 mole) of (+)-4'-hydroxy-2-{[3-(4-methoxyphenyl)-1-methylpropyl]amino}-3'-(methylthio acetophenone which was prepared as the free base according to the method of part A and used immediately after drying 4 hrs. under vacuum at 45° C., there was obtained after precipitation with ethanolic hydrogen chloride from acetone/2-propanol, 2.5 g. of 4'-hydroxy-2-[3-(4-methoxyphenyl)-1-methylpropyl]amino-3'-(methylsulfinyl)-acetophenone hydrochloride as a mixture of diastereomeric sulfoxides, m.p. 192°–194° C. (dec.) $[\alpha]_D^{25} = +19.2°$.

In addition to antihypertensive and antiarrhythmic activity this compound has also been found to possess cardiotonic activity when tested according to the procedures described in Example 5 hereinabove. In the in vitro test this compound at doses of 10, 30 and 100 /ml. caused increases in right atrial rate of 0, 3 and 8 percent respectively; in right atrial force of 1, 5 and 6 percent respectively; and in papillary muscle force of 7, 23 and 38 percent respectively. In the in vitro test, at doses of 1.0, 3.0 and 10.0 mg./kg., the compound caused increases in cardiac contractile force of 22, 25 and 59 percent respectively. In a second, similar series of in vitro tests, increases in cardiac contractile force of 4, 12 and 50 percent were observed.

EXAMPLE 27

A. To a stirred solution containing 45 g. (0.25 mole) of 3,4-dimethoxyphenethylamine in 120 ml. of N,N-dimethylformamide at −55° C. was added dropwise over 25 min. a solution containing 26.1 g. (0.1 mole) of 2-bromo-4'-hydroxy-3'-(methylthio)acetophenone in 60 ml. of N,N-dimethylformamide. After addition was complete, stirring at −48° C. to −55° C. was continued an additional hour. The reaction mixture was then acidified by dropwise addition of 50 ml. of 48% hydrobromic acid diluted with 60 ml. of water and washed with benzene and ether. The aqueous solution was evaporated to dryness under vacuum. The residue was treated with hot methanol and the insoluble N,N-bis-[4-hydroxy-3-(methylthio)phenacyl]-3,4-dimethoxyphenethylamine was filtered off. The filtrate was concentrated, diluted with 2-propanol and cooled. The resulting solid was recrystallized from water, again filtering off insoluble by-product. The product thus obtained was recrystallized from aqueous ethanol, and a 5.5-gram sample was converted to the hydrochloride salt in conventional fashion affording 4.6 g. of 2-{[2-(3,4-dimethoxyphenyl)ethyl]amino}-4'-hydroxy-3'-(methylthio)acetophenone hydrochloride, m.p. 208°–212° C.

B. Following a procedure similar to that described in Example 15E but employing 13.1 g. (0.033 mole) of 2-{[2-(3,4-dimethoxyphenyl)ethyl]amino}-4'-hydroxy-3'-(methylthio)acetophenone hydrochloride and 2.0 g. (0.053 mole) of sodium borohydride; acidifying the reaction mixture with 6N hydrochloric acid and isolating the hydrochloride salt afforded 11.5 g. of α-<{[2-(3,4-dimethoxyphenyl)ethyl]amino}methyl>-4-hydroxy-3-(methylthio)benzenemethanol hydrochloride, m.p. 124°–126° C.

C. Following a procedure similar to that described in Example 2G but employing 5.6 g. (0.014 mole) of α-<{[2-(3,4-dimethoxyphenyl)ethyl]amino}methyl>-4-hydroxy-3-(methylthio)benzenemethanol hydrochloride and 2.13 ml. of commercial 50% peracetic acid there was obtained upon crystallization from 2-propanol, 4.9 g. of α-<{[2-(3,4-dimethoxyphenyl)ethyl]amino}methyl>-4-hydroxy-3-(methylsulfinyl)benzenemethanol hydrochloride m.p. 173°–175° C.

EXAMPLE 28

A. Following a procedure similar to that described in Example 27A but employing 61 g. (0.29 mole) of mescaline and 28 g. (0.107 mole) of 2-bromo-4'-hydroxy-3'-(methylthio)acetophenone there was obtained 33 g. of crystalline product contaminated with a small amount of N,N-bis-[4-hydroxy-3-(methylthio)phenacyl]-3,4,5-trimethoxyphenethylamine. The product was taken up in boiling water and the insoluble by-product was filtered off. Concentration of the filtrate to a small volume produced 18.2 g. of 4'-hydroxy-3'-(methylthio)-2-{[2-(3,4,5-trimethoxyphenyl)ethyl]amino}acetophenone hydrobromide. The hydrochloride isolated as the monohydrate had m.p. 193°–195° C.

B. Following a procedure similar to that described in Example 15E but employing 16 g. of 4'-hydroxy-3'-(methylthio)-2-{[2-(3,4,5-trimethoxyphenyl)ethyl]amino}acetophenone hydrobromide and 2.5 g. of sodium borohydride; and isolating the product as the hydrochloride there was obtained 14.6 g. of 4-hydroxy-3-(methylthio)-α-<{[2-(3,4,5-trimethoxyphenyl)ethyl]amino}methyl>benzenemethanol hydrochloride, m.p. 168°–169.5° C.

C. Following a procedure similar to that described in Example 2G but employing 7.7 g. (0.0175 mole) of 4-hydroxy-3-(methylthio)-α-<{[2-(3,4,5-trimethoxyphenyl)ethyl]amino}-methyl>benzenemethanol hydrochloride and 2.66 ml. (0.0175 mole) of commercial 50 percent peracetic acid; and crystallizing the product from methanol-ether there was obtained 6.8 g. of 4-hydroxy-3-(methylsulfinyl)-α-<{[2-(3,4,5-trimethoxyphenyl)ethyl]amino}methyl>benzenemethanol hydrochloride, m.p. 164°–166° C.

EXAMPLE 29

A. To a stirred solution containing 12 g. of 4-hydroxy-α-<{[3-(4-methoxyphenyl)-1-methylpropyl]amino}methyl>-3-(methylthio)benzenemethanol prepared according to Example 5C in 50 ml. of chloroform at 50° C. was added 20 ml. of thionyl chloride. The temperature was maintained at 50° C. and after stirring a short time the product began to crystallize. After stirring 2 hrs. the mixture was cooled and the precipitated product was collected and washed with benzene to give after drying, 11 g. of 4-hydroxy-α-<{[3-(4-methoxyphenyl)-1-methylpropyl]amino}methyl>-3-(methylthio)benzyl chloride hydrochloride.

B. To a stirred solution containing 9.6 g. (0.0226 mole) of 4-hydroxy-α-<{[3-(4-methoxyphenyl)-1-methylpropyl]amino}methyl>benzyl chloride hydrochloride in 80 ml. of N,N-dimethylformamide at 0° to 10° C. under nitrogen was added portionwise over 0.25 hr. 1.9 g. (0.05 mole) of sodium borohydride. After stirring an additional hour the reaction mixture was neutralized with glacial acetic acid, diluted with chloroform and washed with saturated aqueous sodium bicarbonate. The chloroform solution was dried over anhydrous sodium sulfate and evaporated to dryness. The residue was dissolved in 9:1 2-propanol-methanol and the resulting solution was acidified with ethereal hydrogen chloride. On concentration and cooling there was obtained 5.5 g. of (+)-4-<2-{[3-(4-methoxyphenyl)-1-methylpropyl]amino}ethyl>-2-(methylthio)phenol hydrochloride, m.p. 184°–185° C.

C. To a stirred solution containing 5.0 g. (0.0135 mole) of (+)-4-<2-{[3-(4-methoxyphenyl)-1-methylpropyl]amino}ethyl>-2-(methylthio)phenol hydrochloride in 50 ml. of methanol was added 10 ml. of commercial 50% peracetic acid. The reaction mixture was then cooled to 0°–5° C. and treated with an additional 10 ml. of peracetic acid. After the addition was complete the reaction mixture was concentrated to 20 ml. and diluted with 50 ml. of 2-propanol. On standing at 5° C. overnight the product crystallized. It was collected and dried to give 4.5 g. of 4-<2-{[3-(4-methoxyphenyl)-1-methylpropyl]amino}ethyl>-2-(methylsulfinyl)phenol hydrochloride, m.p. 205°–208° C.

EXAMPLE 30

A. A mixture of 50 g. (0.925 mole) of (+)-4'-hydroxy-2-{3-(4-methoxyphenyl)-1-methylpropyl]amino}-3'-(methylthio)acetophenone 4'-benzoate hydrobromide and 500 ml. of 48 percent hydrobromic acid was stirred and heated under reflux 1 hr. On cooling the product crystallized. It was collected and recrystallized from ethanol-isopropyl acetate to give 26.7 g. of (+)-4'-hydroxy-2-{[3-(4-hydroxyphenyl)-1-methylpropyl]amino}-3'-(methylthio)acetophenone hydrobromide.

B. Following a procedure similar to that described in Example 27B but employing 33 g. (0.0765 mole) of (+)-4'-hydroxy-2-{[3-(4-hydroxyphenyl)-1-methylpropyl]amino}-3'-(methylthio)acetophenone hydrobromide and 3.3 g. of sodium borohydride there was obtained 4-hydroxy-α-<{[3-(4-hydroxyphenyl)-1-methylpropyl]amino}methyl>-3-(methylthio)benzenemethanol which was used directly in a further reaction.

C. A stirred solution containing 0.075 mole of crude 4-hydroxy-α-<{[3-(4-hydroxyphenyl)-1-methylpropyl]amino}methyl>-3-(methylthio)benzenemethanol in 50 ml. of dry dioxane was saturated with hydrogen chloride over 1.5 hrs. After stirring overnight the reaction mixture was diluted with ether, filtered through cotton and then concentrated to a volume of 150 ml. The concentrate was cooled and the precipitated product was collected and dried to give 27.8 g. of 4-hydroxy-α-<{[3-(4-hydroxyphenyl)-1-methylpropyl]amino}methyl>-3-(methylthio)benzyl chloride hydrochloride.

D. To a stirred solution containing 27.8 g. (0.0685 mole) of 4-hydroxy-α-<{[3-(4-hydroxyphenyl)-1-methylpropyl]amino}methyl>-3-(methylthio)benzyl chloride hydrochloride in 150 ml. of N,N-dimethylformamide at 0° C. was added portionwise over 0.25 hr. 4 g. of sodium borohydride. After stirring an additional 0.5 hr. the reaction mixture was acidified with 6N hydrochloric acid, concentrated to near dryness, diluted with saturated aqueous sodium bicarbonate and extracted thoroughly with ethyl acetate. The extracts were washed with saturated aqueous sodium chloride, dried over anhydrous sodium sulfate and evaporated to dryness under vacuum. The residue was dissolved in a mixture of ether and ethyl acetate and the resulting solution was acidified with ethanolic hydrogen chloride and cooled. The solid which crystallized was collected and recrystallized from acetone-methanol-ether to give 15.0 g. of (+)-4-<-2-{[3-(4-hydroxyphenyl)-1-methylpropyl]amino}ethyl>-2-(methylthio)phenol hydrochloride. Recrystallization of a sample from methanol-acetone-ether and then from 2-propanol-ether followed by drying 4 hrs. under vacuum at 100°-115° C. afforded a material having m.p. 150°-151° C.

E. To a stirred solution containing 4.2 g. (0.0114 mole) of (+)-4-<2-{[3-(4-hydroxyphenyl)-1-methylpropyl]amino}ethyl>-2-(methylthio)phenol hydrochloride in 75 ml. of methanol at 0° C. was added over 20 min. 1.73 ml. of commercial 50% peracetic acid in 5 ml. of methanol. When the addition was complete the reaction mixture was evaporated to dryness and the residue was crystallized from acetonitrile/2-propanol to give after drying 3 hrs. under vacuum at 100° C., 5.7 g. of 4-<2-{[3-(4-hydroxyphenyl)-1-methylpropyl]amino}ethyl>-2-(methylsulfinyl)phenol hydrochloride, m.p. 204°-205° C.

EXAMPLE 31

Following a procedure similar to that described in Example 2E but employing 42 g. (0.22 mole) of 3-(3,4-methylenedioxyphenyl)-1-methylpropylamine and 31 g. (0.085 mole) of 2-bromo-4'-hydroxy-3'-(methylthio)acetophenone 4'-benzoate, there was obtained 33 g. of 4'-hydroxy-2-{[3-(3,4-methylenedioxyphenyl)-1-methylpropyl]amino}-3'-(methylthio)acetophenone 4'-benzoate hydrobromide m.p. 146°-148° C.

B. Following a procedure similar to that described in Example 2F but employing 33 g. (0.059 mole) of 4'-hydroxy-2-{[3-(3,4-methylenedioxyphenyl)-1-methylpropyl]amino}-3'-(methylthio)acetophenone 4'-benzoate hydrobromide, 1.2 g. (0.031 mole) of sodium borohydride and 35 ml. of 35% aqueous sodium hydroxide there was obtained 17.5 g. of 4-hydroxy-α-<{[3,(3,4-methylenedioxyphenyl)-1-methylpropyl]amino}methyl>-3-(methylthio)benzenemethanol hydrochloride m.p. 168°-170° C.

C. Following a procedure similar to that described in Example 30E but employing 10.0 g. (0.025 mole) of 4-hydroxy-α-<{[3-(3,4-methylenedioxyphenyl)-1-methylpropyl]amino}methyl>-3-(methylthio)benzenemethanol hydrochloride and 3.75 ml. (0.025 mole) of commercial 40% peracetic acid there was obtained 7.8 g. of 4-hydroxy-α-<{[3-(3,4-methylenedioxyphenyl)-1-methylpropyl]amino}methyl>-3-(methylsulfinyl)benzenemethanol hydrochloride m.p. 175°-180° C.

EXAMPLE 32

A. A mixture containing 46.8 g. (0.257 mole) of 4'-hydroxy-3'-(methylthio)acetophenone, 50 g. (0.327 mole) of bromoethyl ethyl ether and 41.5 g. (0.30 mole) of potassium carbonate in 350 ml. of N,N-dimethylformamide was stirred overnight at 50° C. The reaction mixture was filtered and the filtrate was evaporated to dryness. The residue was dissolved in ether and washed thoroughly with water. The ethereal solution was then filtered to remove a small amount of insoluble material and the filtrate was evaporated to dryness. The resulting yellow oil was distilled at 0.02 mm. to give 59 g. of 4'-[2-(ethoxy)ethoxy]-3'-(methylthio)acetophenone, b.p. 178°-180° C.

B. To a stirred mixture containing 58 g. (0.224 mole) of 4'-[2-(ethoxy)ethoxy]-3'-(methylthio)acetophenone and 25 g. of calcium carbonate in 500 ml. of chloroform was added dropwise over 1.75 hours 36 g. of bromine in 30 ml. chloroform. The reaction mixture was then washed successively with water, saturated aqueous sodium bicarbonate and saturated aqueous sodium chloride. The chloroform layer was dried over anhydrous sodium sulfate and evaporated to dryness to give 72 g. of 2-bromo-4'-[2-(ethoxy)ethoxy]-3'-(methylthio)acetophenone as a pale yellow oil.

C. To a stirred solution containing 85 g. (0.5 mole) of (+)-3-(4-methoxyphenyl)-1-methylpropylamine in 300 ml. of N,N-dimethylformamide at −50° C. was added dropwise over a period of 1.75 hrs. a solution containing 72 g. (0.20 mole) of 2-bromo-4'-[2-(ethoxy)ethoxy]-3'-(methylthio)acetophenone in 150 ml. of N,N-dimethylformamide. When the addition was complete, the mixture was acidified with 48% hydrobromic acid and then partitioned between dichloromethane and water. The organic layer was separated, washed with water and saturated aqueous sodium chloride and evaporated to dryness. The partially crystalline residue was diluted with ether, cooled and filtered to give 68 g. of (+)-4'-[2-(ethoxy)ethoxy]-2-{[3-(4-methoxyphenyl)-1-methylpropyl]amino}-3'-(methylthio)acetophenone hydrobromide.

D. To a stirred solution containing 66 g. (0.129 mole) of (+)-4'-[2-(ethoxy]-2-{[3-(4-methoxyphenyl)-1-methylpropyl]amino}-3'-(methylthio)acetophenone hydrobromide in 400 ml. of methanol at 0° C. was added portionwise over 0.5 hr. 2.6 g. (0.070 mole) of sodium borohydride. When the addition was complete, the reaction mixture was neutralized with 15 ml. of acetic acid and evaporated to dryness. The residue was diluted with dichloromethane and washed with saturated aqueous sodium bicarbonate and saturated aqueous sodium chloride and then dried over anhydrous sodium sulfate and evaporated to dryness under vacuum. The residue was dissolved in a mixture of ether, 2-propanol and isopropyl acetate and the resulting solution acidified with ethanolic hydrogen chloride and cooled. The resulting crystalline product was collected by filtration, washed with a small amount of isopropyl acetate and ether and dried at 60° C. under vacuum to give 53.5 g. of 4-[2-(ethoxy)ethoxy]-α-<{[3-(4-methoxyphenyl)-1-methylpropyl]amino}methyl>-3-(methylthio)benzenemethanol hydrochloride, m.p. 102°–104° C. as a pair of diastereomeric benzenemethanols.

E. To a cold stirred solution containing 11.0 g. (0.024 mole) of 4-[2-(ethoxy)ethoxy]-α-<{[3-(4-methoxyphenyl)-1-methylpropyl]amino}methyl>-3-(methylthio)benzenemethanol hydrochloride in 150 ml. of methanol was added dropwise 3.6 ml. (0.024 mole) of commercial 40% percetic acid. When the addition was complete the reaction mixture was evaporated to dryness, the residue was dissolved in toluene and washed with saturated sodium bicarbonate and saturated aqueous sodium chloride. The toluene solution was dried over anhydrous sodium sulfate and evaporated to dryness. The residue was converted to the hydrochloride salt following conventional procedures to afford 6 g. of 4-[2-(ethoxy)ethoxy]-α-<{[3-(4-methoxyphenyl)-1-methylpropyl]amino}methyl>-3-(methylsulfinyl)benzenemethanol hydrochloride as an off-white amorphous solid containing a mixture of diastereomeric sulfoxides.

EXAMPLES 33

A. Following a procedure similar to that described in Example 29A but employing 23 g. of 4-hydroxy-α{[(1-methyl-3-phenylpropyl)amino]methyl}-3-(methylthio)benzenemethanol prepared according to Example 19B and 25 ml. of thionyl chloride there was obtained 19.5 g. of 4-hydroxy-α-{[(1-methyl-3-phenylpropyl)amino]methyl}-3-(methylthio)benzyl chloride hydrochloride.

B. Following a procedure similar to that described in Example 30D but employing 20 g. of 4-hydroxy-α-{[1-methyl-3-phenylpropyl)amino]methyl}-3-(methylthio)-benzyl chloride hydrochloride and 3 g. of sodium borohydride there was obtained 13.8 g. of 4-<2-{[1-methyl-3-phenylpropyl]amino}ethyl>-2-(methylthio)phenol hydrochloride, m.p. 191°–193° C.

C. To a stirred solution containing 8.5 g. (0.024 mole) of 4-<2-{[1-methyl-3-phenylpropyl]amino}ethyl>-2-(methylthio)phenol hydrochloride in 100 ml. of ethanol at 5° C. was added dropwise over 0.5 hr. 3.7 ml. (0.024 mole) of commercial 40% peracetic acid. When the addition was complete the reaction mixture was evaporated to dryness and the residue was crystallized from 2-propanol affording 7.05 g. of 4-<2-{[1-methyl-3-phenylpropyl]amino}ethyl>-2-(methylsulfinyl)phenol hydrochloride m.p. 217°–219° C.

EXAMPLE 34

A. Following a procedure similar to that described in Example 29A but employing 18 g. of α-<{[1,1-dimethyl-3-(4-methoxyphenyl)propyl]amino}methyl>-4-hydroxy-3-(methylthio)benzenemethanol prepared according to Example 18C and 18 ml. of thionyl chloride there was obtained 9.1 g. of α-<{[1,1-dimethyl-3-(4-methoxyphenyl)propyl]amino}methyl>-4-hydroxy-3-(methylthio)benzyl chloride hydrochloride.

B. Following a procedure similar to that described in Example 30D but employing 9 g. of α-<{[1,1-dimethyl-3-(4-methoxyphenyl)propyl]amino}methyl>-4-hydroxy-3-(methylthio)benzyl chloride hydrochloride and 1 g. of sodium borohydride, there was obtained 6.9 g. of 4-<2-{[3-(4-methoxyphenyl)-1,1-dimethylpropyl]amino}ethyl>-2-(methylthio)phenol hydrochloride m.p. 196°–198° C.

C. Following a procedure similar to that described in Example 33C but employing 6.0 g. (0.015 mole) of 4-<2-{[3-(4-methoxyphenyl)-1,1-dimethylpropyl]amino}ethyl>-2-(methylthio)phenol hydrochloride and 2.3 ml. (0.015 mole) of commercial 40% peracetic acid there was obtained 5.3 g. of 4-<2-{[3-(4-methoxyphenyl)-1,1-dimethylpropyl]amino}ethyl>-2-(methylsulfinyl)phenol hydrochloride, m.p. 231°–232° C.

EXAMPLE 35

A. Following a procedure similar to that described in Example 29A but employing 23 g. of α-{[(1,1-dimethyl-3-phenylpropyl)amino]methyl}-4-hydroxy-3-(methylthio)benzenemethanol and 20 ml. of thionyl chloride there was obtained 18 g. of α-{[(1,1-dimethyl-3-phenylpropyl)amino]methyl}-4-hydroxy-3-(methylthio)benzyl chloride hydrochloride.

B. Following a procedure similar to that described in Example 29B but employing 18 g. of α-{[(1,1-dimethyl-3-phenylpropyl)amino]methyl}-4-hydroxy-3-(methylthio)benzyl chloride hydrochloride and 3 g. of sodium borohydride, there was obtained 12.5 g. of 4-{2-[(1,1-dimethyl-3-phenylpropyl)amino]ethyl}-2-(methylthio)phenol hydrochloride m.p. 181°–183° C.

C. Following a procedure similar to that described in Example 33C but employing 7.5 g. (0.021 mole) of 4-{2-[(1,1-dimethyl-3-phenylpropyl)amino]ethyl}-2-(methylthio)phenol hydrochloride and 3.3 ml. of commercial 40% peracetic acid there was obtained 7.3 g. of 4-{2-[(1,1-dimethyl-3-phenylpropyl)amino]ethyl}-2(methylsulfinyl)phenol hydrochloride, m.p. 244°–246° C.

EXAMPLE 36

A. Following a procedure similar to that described in Example 29A but employing 26 g. of 4-hydroxy-α-<{[3-(4-methoxyphenyl)-1-methylpropyl]amino}methyl>-3-(methylthio)benzenemethanol prepared according to Example 2B and 23 ml. of thionyl chloride there was obtained 16.9 g. of 4-hydroxy-α-<{[3-(4-methoxyphenyl)-1-methylpropyl]amino}methyl>-3-(methylthio)benzyl chloride hydrochloride.

B. Following a procedure similar to that described in Example 30D but employing 16.9 g. of 4-hydroxy-α-<{[3-(4-methoxyphenyl)-1-methylpropyl]amino}methyl>-3-(methylthio)benzyl chloride hydrochloride and 3 g. of sodium borohydride, there was obtained 9.8 g. of 4-<2-{[3-(4-methoxyphenyl)-1-methylpropyl]amino}ethyl>-2-(methylthio)phenol hydrochloride, m.p. 170°–174° C.

C. Following a procedure similar to that described in Example 33C but employing 6.3 g. (0.017 mole) of 4-<2-{[3-(4-methoxyphenyl)-1-methylpropyl]amino}ethyl>-2-(methylthio)phenol hydrochloride and 2.5 ml. (0.017 mole) of commercial 50% peracetic acid there was obtained 5.9 g. of 4-<2-{[3-(4-methoxyphenyl)-1-methylpropyl]amino}ethyl>-2-(methylsulfinyl)phenol hydrochloride, m.p. 217°–218° C.

EXAMPLE 37

A. Following a procedure similar to that described in Example 29A but employing 28 g. of 4-hydroxy-α-<{[3-(4-methoxyphenyl)-1-methylpropyl]amino}methyl>-3-(methylthio)benzenemethanol prepared according to Example 24B and 23 ml. of thionyl chloride there was obtained 23.3 g. of 4-hydroxy-α-<{[3-(4-methoxyphenyl)-1-methylpropyl]amino}methyl>-3-(methylthio)benzyl chloride hydrochloride.

B. Following a procedure similar to that described in Example 30D but employing 23.3 g. of 4-hydroxy-α-<{[3-(4-methoxyphenyl)-1-methylpropyl]amino}methyl>-3-(methylthio)benzyl chloride of Part A and 3 g. of sodium borohydr there was obtained 12.8 g. of (−)-4-<2-{[3-(4-methoxyphenyl)-1-methylpropyl]amino}ethyl>-2-(methylthio)phenol hydrochloride m.p. 184°–185° C., $[\alpha]_D^{25} = -9.28°$.

C. Following a procedure similar to that described in Example 33C but employing 8.8 g. (0.237 mole) of (−)-4-<2-{[3-(4-methoxyphenyl)-1-methylpropyl]amino}ethyl>-2-(methylthio)phenol hydrochloride and 3.6 ml. (0.237 mole) of commercial 50% peracetic acid there was obtained 6.2 g. of 4-<2-{[3-(4-methoxyphenyl)-1-methylpropyl]amino}ethyl>-2-(methylsulfinyl)phenol hydrochloride, m.p. 209°–210° C., $[\alpha]_D^{25} = -8.0°$ as a pair of diastereomeric sulfoxides.

EXAMPLE 38

A. Following a procedure similar to that described in Example 29A but employing 31.7 g. of 4-[2-(ethoxy)ethoxy]-α-<{[3-(4-methoxyphenyl)-1-methylpropyl]amino}methyl>-3-(methylthio)benzenemethanol hydrochloride prepared according to Example 32D and 25 ml. of thionyl chloride there was obtained 30 g. of 4-[2-(ethoxy)ethoxy]-α-<{[3-(4-methoxyphenyl)-1-methylpropyl]amino}methyl>-3-(methylthio)benzyl chloride hydrochloride.

B. Following a procedure similar to that described in Example 30D but employing 30 g. of 4-[2-(ethoxy)ethoxy]-α-<{[3-(4-methoxyphenyl)-1-methylpropyl]amino}methyl>-3-(methylthio)benzyl chloride hydrochloride of Part A and 3.0 g. of sodium borohydride there was obtained 9.9 g. of (+)-4-[2-(ethoxy)ethoxy]-N-[3-(4-methoxyphenyl)-1-methylpropyl]-3-(methylthio)benzeneethanmine hydrochloride, m.p. 95°–99° C.

C. Following a procedure similar to that described in Example 33C but employing 1.65 g. (0.004 mole) of (+)-4-[2-(ethoxy)ethoxy]-N-[3-(4-methoxyphenyl)-1-methylpropyl]-3-(methylthio)benzeneethanamine hydrochloride and 0.56 ml. of commercial 50% peracetic acid there was obtained 1.5 g. of 4-[2-(ethoxy)ethoxy]-N-[3-(4-methoxyphenyl)-1-methylpropyl]-3-(methylsulfinyl)benzeneethanamine hydrochloride, m.p. 80°–85° C. as a pair of diastereomeric sulfoxides.

Additional examples of 3-(lower alkylsulfinyl)benzenemethanols and aminoalkyl 3-(lower alkylsulfinyl)phenyl ketones having respectively Formulas I and II hereinabove, and which, it is contemplated, can be obtained in accordance with the above-described procedures are presented in Table A hereinbelow.

Additional examples of 2-[3-(lower alkylsulfinyl)phenyl]ethylamines having the Formula III hereinabove and which, it is contemplated, can be obtained in accordance with the above-described procedures are presented in Table B hereinbelow.

Additional examples of 3-(lower alkylthio)benzenemethano and aminoalkyl 3-(lower alkylthio)phenyl ketones having respectively Formulas IV and V hereinabove, which are useful intermediates in the preparation of the corresponding 3-(lower alkylsulfinyl compounds of Table A and which, it is contemplated, can be prepared in accordance with the above-described procedures are presented hereinbelow in Table C.

Additional examples of 2-[3-(lower alkylthio)phenyl]ethylamines and 2-halo-2-[3-(lower alkylthio)phenyl]ethylamines having respectively Formulas VI and X which are useful intermediates in the preparation of the compounds of Table B and which, it is contemplated, can be prepared in accordance with the above-described procedures are presented hereinbelow in Table D.

Additional examples of haloketones and the corresponding parent phenyl ketones having respectively Formulas VII and IX hereinabove which are useful intermediates in the preparation of the aminoalkyl 3-(lower alkylthio)phenyl ketones of Formula V (Table C) and which, it is contemplated, can be prepared in accordance with the above-described procedures presented hereinbelow in Tables E and F. The phenyl ketones of Table F can in turn be obtained in accordance with the above-described procedures by acylating the generally known o-(lower alkylthio)phenols with an appropriate acyl halide under Friedel-Crafts conditions followed by esterification or alkylation of the resulting 3-(lower alkylthio)-4-hydroxyphenyl ketones according to conventional esterification or alkylation procedures.

It will be appreciated that among the product aspects of this invention as defined hereinabove by Formulas I, II and III there are of course included the following sub-generia:

The compounds of Formula I hereinabove wherein Y is hydrogen.

The compounds of Formula I wherein Y is lower alkyl or lower alkoxy-lower alkyl.

The compounds of Formula I wherein Y is lower alkanoyl, aroyl, benzenesulfonyl or toluenesulfonyl.

The compounds of Formula II hereinabove wherein Y is hydrogen.

The compounds of Formula II wherein Y is lower alkyl or lower alkoxy-lower alkyl.

The compounds of Formula II wherein Y is lower alkanoyl, aroyl, benzenesulfonyl or toluenesulfonyl.

The compounds of Formula III hereinabove wherein Y is hydrogen.

The compounds of Formula III wherein Y is lower alkyl or lower alkoxy-lower alkyl.

The compounds of Formula III wherein Y is lower alkanoyl, aroyl, benzenesulfonyl or toluenesulfonyl.

TABLE A

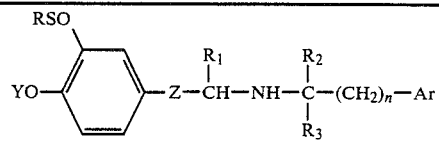

3-(Lower alkylsulfinyl)benzenemethanols of Formula I: Z is CHOH
Aminoalkyl 3-(lower alkylsulfinyl)phenyl ketones of Formula II: Z is C=O

| Y | R | $R_1$ | $R_2$ | $R_3$ | n | Ar |
|---|---|---|---|---|---|---|
| H | $CH_3$ | $C_2H_5$ | H | $CH_3$ | 2 | p-$CH_3OC_6H_4$ |
| p-$CH_3C_6H_4CO$ | $CH_3$ | H | H | $CH_3$ | 2 | p-$CH_3OC_6H_4$ |

TABLE A-continued

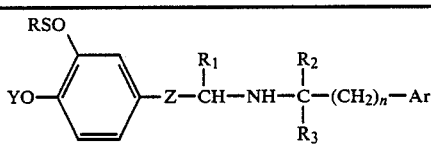

3-(Lower alkylsulfinyl)benzenemethanols of Formula I: Z is CHOH
Aminoalkyl 3-(lower alkylsulfinyl)phenyl ketones of Formula II: Z is C=O

| Y | R | $R_1$ | $R_2$ | $R_3$ | n | Ar |
|---|---|---|---|---|---|---|
| $(CH_3)_3CCO$ | $CH_3$ | H | H | $CH_3$ | 2 | p-$CH_3OC_6H_4$ |
| HCO | $C_2H_5$ | H | H | $C_2H_5$ | 1 | $C_6H_5$ |
| $C_5H_{11}O$ | $CH_3$ | H | H | H | 1 | $C_6H_5$ |
| H | $C_2H_5$ | H | H | $CH_3$ | 2 | p-$CH_3C_6H_4$ |
| H | n-$C_4H_9$ | H | H | $CH_3$ | 1 | m-$CH_3OC_6H_4$ |
| H | $CH_3$ | H | H | $CH(CH_3)_2$ | 1 | $C_6H_5$ |
| H | $CH_3$ | n-$C_4H_9$ | H | H | 1 | p-$(CH_3)_3CC_6H_4$ |
| H | $CH_3$ | H | $CH_3$ | $CH_3$ | 1 | 2,5-$(CH_3)_2$—$C_6H_3$ |
| H | $CH_3$ | H | H | H | 1 | p-$(CH_3)_2CHCH_2OC_6H_4$ |
| H | $CH_3$ | n-$C_3H_7$ | H | $C_4H_9$ | 1 | $C_6H_5$ |
| H | $CH_3$ | H | H | $CH_3$ | 1 | 3,4-$(HO)_2$—$C_6H_3$ |
| H | $CH_3$ | H | H | H | 1 | 3,4,5-$(HO)_3$—$C_6H_2$ |
| H | $CH_3$ | H | H | $CH_3$ | 2 | 3-Br—4-HO—$C_6H_3$ |
| H | $CH_3$ | H | H | H | 1 | 3-F—$C_6H_4$ |
| H | $CH_3$ | H | $CH_3$ | $CH_3$ | 1 | 4-Br—$C_6H_4$ |
| H | $CH_3$ | H | H | $CH_3$ | 1 | 2,5-$(Cl)_2$—$C_6H_3$ |
| H | $CH_3$ | H | H | H | 1 | 3,4,5-$(Cl)_3$—$C_6H_2$ |
| H | $CH_3$ | H | H | H | 1 | 2,4,6-$(CH_3)_3$—$C_6H_2$ |
| H | $CH_3$ | H | H | $CH_3$ | 1 | 2-$(C_4H_9O)$—3-$CH_3O$—$C_6H_3$ |
| $CH_3$ | $CH_3$ | H | H | H | 2 | p-$CH_3OC_6H_4$ |
| $CH_3OCH_2$ | $CH_3$ | H | H | H | 1 | 3,4-$(CH_2\overset{O}{\underset{O}{\diagdown\!\!\diagup}})$—$C_6H_3$ |
| $(CH_3)_2CHCH_2OC_2H_4$ | $CH_3$ | H | H | H | 3 | $C_6H_5$ |
| $C_4H_9O-\overset{C_2H_5}{\underset{}{C}HCH_2}$ | n-$C_3H_7$ | H | H | H | 1 | $C_6H_5$ |
| $C_3H_7OC_3H_6$ | $CH_3$ | H | H | H | 2 | p-$CH_3O$—$C_6H_4$ |
| $C_6H_5SO_2$ | $CH_3$ | H | H | H | 2 | p-$CH_3OC_6H_4$ |
| n-$C_4H_9$ | $CH_3$ | H | H | $CH_3$ | 2 | p-$CH_3OC_6H_4$ |

TABLE B

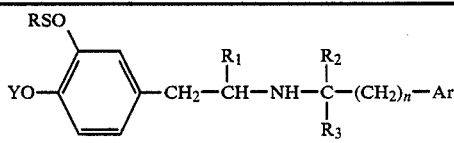

2-[3-(lower alkylsulfinyl)phenyl]ethylamines of Formula III

| Y | R | $R_1$ | $R_2$ | $R_3$ | n | Ar |
|---|---|---|---|---|---|---|
| $CH_3CO$ | $CH_3$ | H | $CH_3$ | $CH_3$ | 1 | $C_6H_5$ |
| H | $CH_3$ | $CH_3$ | $CH_3$ | H | 1 | p-$CH_3OC_6H_4$ |
| H | $CH_3$ | H | H | H | 2 | $C_6H_5$ |
| H | $CH_3$ | H | H | $CH_3$ | 1 | 3,4-$(CH_3O)_2$—$C_6H_3$ |
| H | $CH_3$ | H | H | $CH_3$ | 3 | p-$CH_3OC_6H_4$ |
| $C_6H_5CO$ | $CH_3$ | H | H | $CH_3$ | 2 | 3-Br—4-$CH_3O$—$C_6H_3$ |
| H | $CH_3$ | H | $CH_3$ | $CH_3$ | 2 | p-$CH_3OC_6H_4$ |
| H | $CH_3$ | H | H | H | 1 | 3,4,5-$(CH_3O)_3$—$C_6H_2$ |
| H | $CH_3$ | $C_2H_5$ | H | $CH_3$ | 2 | p-$CH_3OC_6H_4$ |
| p-$CH_3C_6H_4CO$ | $CH_3$ | H | H | $CH_3$ | 2 | p-$CH_3OC_6H_4$ |
| $(CH_3)_3CCO$ | $CH_3$ | H | H | $CH_3$ | 2 | p-$CH_3OC_6H_4$ |
| HCO | $C_2H_5$ | H | H | $C_2H_5$ | 1 | $C_6H_5$ |
| $C_5H_{11}CO$ | $CH_3$ | H | H | H | 1 | $C_6H_5$ |
| H | $C_2H_5$ | H | H | $CH_3$ | 2 | p-$CH_3C_6H_4$ |
| H | n-$C_4H_9$ | H | H | $CH_3$ | 1 | m-$CH_3OC_6H_4$ |
| H | $CH_3$ | H | H | $CH(CH_3)_2$ | 1 | $C_6H_5$ |
| H | $CH_3$ | n-$C_4H_9$ | H | H | 1 | p-$(CH_3)_3CC_6H_4$ |
| H | $CH_3$ | H | $CH_3$ | $CH_3$ | 1 | 2,5-$(CH_3)_2$—$C_6H_3$ |
| H | $CH_3$ | H | H | H | 1 | p-$(CH_3)_2CHCH_2OC_6H_4$ |
| H | $CH_3$ | n-$C_3H_7$ | H | $C_4H_9$ | 1 | $C_6H_5$ |
| H | $CH_3$ | H | H | $CH_3$ | 1 | 3,4-$(HO)_2$—$C_6H_3$ |

TABLE B-continued

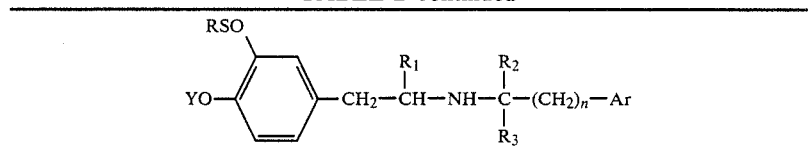

2-[3-(lower alkylsulfinyl)phenyl]ethylamines of Formula III

| Y | R | $R_1$ | $R_2$ | $R_3$ | n | Ar |
|---|---|---|---|---|---|---|
| H | $CH_3$ | H | H | H | 1 | 3,4,5-$(HO)_3$—$C_6H_2$ |
| H | $CH_3$ | H | H | $CH_3$ | 2 | 3-Br—4-HO—$C_6H_3$ |
| H | $CH_3$ | H | H | H | 1 | 3-F—$C_6H_4$ |
| H | $CH_3$ | H | $CH_3$ | $CH_3$ | 1 | 4-Br—$C_6H_4$ |
| H | $CH_3$ | H | H | $CH_3$ | 1 | 2,5-$(Cl)_2$—$C_6H_3$ |
| H | $CH_3$ | H | H | H | 1 | 3,4,5-$(Cl)_3$—$C_6H_2$ |
| H | $CH_3$ | H | H | H | 1 | 2,4,6-$(CH_3)_3$—$C_6H_2$ |
| H | $CH_3$ | H | H | $CH_3$ | 1 | 2-$(C_4H_9O)$—3-$CH_3O$—$C_6H_3$ |
| $CH_3$ | $CH_3$ | H | H | H | 2 | p-$CH_3O$—$C_6H_4$ |
| $CH_3OCH_2$ | $CH_3$ | H | H | H | 1 | 3,4—$(CH_2\begin{smallmatrix}O\\O\end{smallmatrix})$—$C_6H_3$ |
| $(CH_3)_2CHCH_2OC_2H_4$ | $CH_3$ | H | H | H | 3 | $C_6H_5$ |
| $C_4H_9O$—$\underset{\underset{C_2H_5}{\mid}}{CHCH_2}$ | n-$C_3H_7$ | H | H | H | 1 | $C_6H_5$ |
| $C_3H_7OC_3H_6$ | $CH_3$ | H | H | H | 2 | p-$CH_3OC_6H_4$ |
| $C_6H_5SO_2$ | $CH_3$ | H | H | H | 2 | p-$CH_3OC_6H_4$ |
| n-$C_4H_9$ | $CH_3$ | H | H | H | 2 | p-$CH_3OC_6H_4$ |

TABLE C

Intermediates

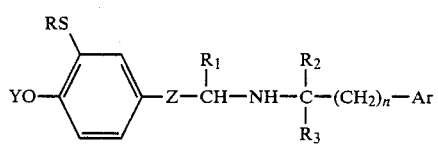

3-(Lower alkylthio)benzenemethanols of Formula IV: Z is CHOH
Aminoalkyl 3-(lower alkylthio)phenyl ketones of Formula V: Z is C=O

| Y | R | $R_1$ | $R_2$ | $R_3$ | n | Ar |
|---|---|---|---|---|---|---|
| H | $CH_3$ | $C_2H_5$ | H | $CH_3$ | 2 | p-$CH_3OC_6H_4$ |
| p-$CH_3C_6H_4CO$ | $CH_3$ | H | H | $CH_3$ | 2 | p-$CH_3OC_6H_4$ |
| $(CH_3)_3CCO$ | $CH_3$ | H | H | $CH_3$ | 2 | p-$CH_3OC_6H_4$ |
| HCO | $C_2H_5$ | H | H | $C_2H_5$ | 1 | $C_6H_5$ |
| $C_5H_{11}CO$ | $CH_3$ | H | H | H | 1 | $C_6H_5$ |
| H | $C_2H_5$ | H | H | $CH_3$ | 2 | p-$CH_3C_6H_4$ |
| H | n-$C_4H_9$ | H | H | $CH_3$ | 1 | m-$CH_3OC_6H_4$ |
| H | $CH_3$ | H | H | $CH(CH_3)_2$ | 1 | $C_6H_5$ |
| H | $CH_3$ | n-$C_4H_9$ | H | H | 1 | p-$(CH_3)_3CC_6H_4$ |
| H | $CH_3$ | H | $CH_3$ | $CH_3$ | 1 | 2,5-$(CH_3)_2$—$C_6H_3$ |
| H | $CH_3$ | H | H | H | 1 | p-$(CH_3)_2CHCH_2OCH_6H_4$ |
| H | $CH_3$ | n-$C_3H_7$ | H | $C_4H_9$ | 1 | $C_6H_5$ |
| H | $CH_3$ | H | H | $CH_3$ | 1 | 3,4-$(HO)_2$—$C_6H_3$ |
| H | $CH_3$ | H | H | H | 1 | 3,4,5-$(HO)_3$—$C_6H_2$ |
| H | $CH_3$ | H | H | $CH_3$ | 2 | 3-Br—4-HO—$C_6H_3$ |
| H | $CH_3$ | H | H | H | 1 | 3-F—$C_6H_4$ |
| H | $CH_3$ | H | $CH_3$ | $CH_3$ | 1 | 4-Br—$C_6H_4$ |
| H | $CH_3$ | H | H | $CH_3$ | 1 | 2,5-$(Cl)_2$—$C_6H_3$ |
| H | $CH_3$ | H | H | H | 1 | 3,4,5-$(Cl)_3$—$C_6H_2$ |
| H | $CH_3$ | H | H | H | 1 | 2,4,6-$(CH_3)_3$—$C_6H_2$ |
| H | $CH_3$ | H | H | $CH_3$ | 1 | 2-$(C_4H_9O)$—3-$CH_3O$—$C_6H_3$ |
| $CH_3$ | $CH_3$ | H | H | H | 2 | p-$CH_3OC_6H_4$ |
| $CH_3OCH_2$ | $CH_3$ | H | H | H | 1 | 3,4-$(CH\begin{smallmatrix}O\\O\end{smallmatrix})$—$C_6H_3$ |
| $(CH_3)_2CHCH_2OC_2H_4$ | $CH_3$ | H | H | H | 3 | $C_6H_5$ |

TABLE C-continued

Intermediates

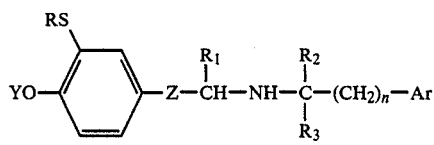

3-(Lower alkylthio)benzenemethanols of Formula IV: Z is CHOH
Aminoalkyl 3-(lower alkylthio)phenyl ketones of Formula V: Z is C=O

| Y | R | $R_1$ | $R_2$ | $R_3$ | n | Ar |
|---|---|---|---|---|---|---|
| $C_4H_9O-\overset{C_2H_5}{\underset{|}{C}}HCH_2$ | $\underline{n}$-$C_3H_7$ | H | H | H | 1 | $C_6H_5$ |
| $C_3H_7OC_3H_6$ | $CH_3$ | H | H | H | 2 | p-$CH_3O-C_6H_4$ |
| $C_6H_5SO_2$ | $CH_3$ | H | H | H | 2 | $\underline{p}$-$CH_3OC_6H_4$ |
| $\underline{n}$-$C_4H_9$ | $CH_3$ | H | H | $CH_3$ | 2 | $\underline{p}$-$CH_3OC_6H_4$ |

TABLE D

Intermediates

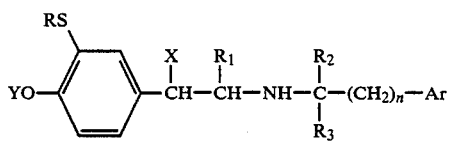

2-[3-(lower alkylthio)phenyl]ethylamines of Formula VI: X is H
2-halo-2-[3-(lower alkylthio)phenyl]ethylamines of Formula X: X is chloro, bromo or iodo

| Y | R | $R_1$ | $R_2$ | $R_3$ | n | Ar |
|---|---|---|---|---|---|---|
| $CH_3CO$ | $CH_3$ | H | $CH_3$ | $CH_3$ | 1 | $C_6H_5$ |
| H | $CH_3$ | $CH_3$ | $CH_3$ | H | 1 | p-$CH_3OC_6H_4$ |
| H | $CH_3$ | H | H | H | 2 | $C_6H_5$ |
| H | $CH_3$ | H | H | $CH_3$ | 1 | 3,4-$(CH_3O)_2$—$C_6H_3$ |
| H | $CH_3$ | H | H | $CH_3$ | 3 | p-$CH_3OC_6H_4$ |
| $C_6H_5CO$ | $CH_3$ | H | H | $CH_3$ | 2 | 3-Br—4-$CH_3O$—$C_6H_3$ |
| H | $CH_3$ | H | $CH_3$ | $CH_3$ | 2 | p-$CH_3OC_6H_4$ |
| H | $CH_3$ | H | H | H | 1 | 3,4,5-$(CH_3O)_3$—$C_6H_2$ |
| H | $CH_3$ | $C_2H_5$ | H | $CH_3$ | 2 | p-$CH_3OC_6H_4$ |
| p-$CH_3C_6H_4CO$ | $CH_3$ | H | H | $CH_3$ | 2 | p-$CH_3OC_6H_4$ |
| $(CH_3)_3CCO$ | $CH_3$ | H | H | $CH_3$ | 2 | p-$CH_3OC_6H_4$ |
| HCO | $C_2H_5$ | H | H | $C_2H_5$ | 1 | $C_6H_5$ |
| $C_5H_{11}CO$ | $CH_3$ | H | H | H | 1 | $C_6H_5$ |
| H | $C_2H_5$ | H | H | $CH_3$ | 2 | p-$CH_3C_6H_4$ |
| H | $\underline{n}$-$C_4H_9$ | H | H | $CH_3$ | 1 | $\underline{m}$-$CH_3OC_6H_4$ |
| H | $CH_3$ | H | H | $CH(CH_3)_2$ | 1 | $C_6H_5$ |
| H | $CH_3$ | $\underline{n}$-$C_4H_9$ | H | H | 1 | p-$(CH_3)_3CC_6H_4$ |
| H | $CH_3$ | H | $CH_3$ | $CH_3$ | 1 | 2,5-$(CH_3)_2$—$C_6H_3$ |
| H | $CH_3$ | H | H | H | 1 | p-$(CH_3)_2CHCH_2OC_6H_4$ |
| H | $CH_3$ | $\underline{n}$-$C_3H_7$ | H | $C_4H_9$ | 1 | $C_6H_5$ |
| H | $CH_3$ | H | H | $CH_3$ | 1 | 3,4-$(HO)_2$—$C_6H_3$ |
| H | $CH_3$ | H | H | H | 1 | 3,4,5-$(HO)_3$—$C_6H_2$ |
| H | $CH_3$ | H | H | $CH_3$ | 2 | 3-Br—4-HO—$C_6H_3$ |
| H | $CH_3$ | H | H | H | 1 | 3-F—$C_6H_4$ |
| H | $CH_3$ | H | $CH_3$ | $CH_3$ | 1 | 4-Br—$C_6H_4$ |
| H | $CH_3$ | H | H | $CH_3$ | 1 | 2,5-$(Cl)_2$—$C_6H_3$ |
| H | $CH_3$ | H | H | H | 1 | 3,4,5-$(Cl)_3$—$C_6H_2$ |
| H | $CH_3$ | H | H | H | 1 | 2,4,6-$(CH_3)_3$—$C_6H_2$ |
| H | $CH_3$ | H | H | $CH_3$ | 1 | 2-$(C_4H_9O)$—3-$CH_3O$—$C_6H_3$ |
| $CH_3$ | $CH_3$ | H | H | H | 2 | p-$CH_3O$—$C_6H_4$ |
| $CH_3OCH_2$ | $CH_3$ | H | H | H | 1 | 3,4-$(CH_2\overset{O}{\underset{O}{\diagup\!\!\diagdown}})$—$C_6H_3$ |
| $(CH_3)_2CHCH_2OC_2H_4$ | $CH_3$ | H | H | H | 3 | $C_6H_5$ |
| $C_4H_9O-\overset{C_2H_5}{\underset{|}{C}}HCH_2$ | $\underline{n}$-$C_3H_7$ | H | H | H | 1 | $C_6H_5$ |
| $C_3H_7OC_3H_6$ | $CH_3$ | H | H | H | 2 | $\underline{p}$-$CH_3OC_6H_4$ |
| $C_6H_5SO_2$ | $CH_3$ | H | H | H | 2 | $\underline{p}$-$CH_3OC_6H_4$ |

TABLE D-continued

Intermediates $$\text{YO}-\text{C}_6\text{H}_3(\text{SR})-\text{CHX}-\text{CHR}_1-\text{NH}-\text{CR}_2\text{R}_3-(\text{CH}_2)_n-\text{Ar}$$

2-[3-(lower alkylthio)phenyl]ethylamines of Formula VI: X is H
2-halo-2-[3-(lower alkylthio)phenyl]ethylamines of Formula X: X is chloro, bromo or iodo

| Y | R | $R_1$ | $R_2$ | $R_3$ | n | Ar |
|---|---|---|---|---|---|---|
| n—$C_4H_9$ | $CH_3$ | H | H | H | 2 | p-$CH_3OC_6H_4$ |

TABLE E

Intermediates $$\text{YO}-\text{C}_6\text{H}_3(\text{SR})-\text{CO}-\text{CHR}_1-\text{X}$$

Haloketones of Formula VII

| Y | R | $R_1$ | X |
|---|---|---|---|
| H | $CH_3$ | $C_2H_5$ | Br |
| p-$CH_3C_6H_4CO$ | $CH_3$ | H | Br |
| $(CH_3)_3CCO$ | $CH_3$ | H | Br |
| HCO | $C_2H_5$ | H | Cl |
| $C_5H_{11}O$ | $CH_3$ | H | Br |
| H | $C_2H_5$ | H | Br |
| $CH_3CO$ | n-$C_4H_9$ | H | Cl |
| H | $CH_3$ | n-$C_4H_9$ | Br |
| H | $CH_3$ | n-$C_3H_7$ | Br |
| $CH_3$ | $CH_3$ | H | Br |
| $CH_3OCH_2$ | $CH_3$ | H | Br |
| $(CH_3)_2CHCH_2OC_2H_4$ | $CH_3$ | H | Br |
| $C_4H_9OCHCH_2$ (with $C_2H_5$ branch) | n-$C_3H_7$ | H | Br |
| $C_3H_7OC_3H_6$ | $CH_3$ | H | Br |
| $C_6H_5SO_2$ | $CH_3$ | H | Br |
| n-$C_4H_9$ | $CH_3$ | H | Br |

TABLE F

Intermediates $$\text{YO}-\text{C}_6\text{H}_3(\text{SR})-\text{CO}-\text{CH}_2-\text{R}_1$$

3-(Lower alkylthio)phenyl ketones of Formula IX

| Y | R | $R_1$ |
|---|---|---|
| $CH_3CO$ | $CH_3$ | $C_2H_5$ |
| p-$CH_3C_6H_4CO$ | $CH_3$ | H |
| $(CH_3)_3CCO$ | $CH_3$ | H |
| HCO | $C_2H_5$ | H |
| $C_5H_{11}CO$ | $CH_3$ | H |
| $CH_3CO$ | $C_2H_5$ | H |
| $CH_3CO$ | n-$C_4H_9$ | H |
| $CH_3CO$ | $CH_3$ | n-$C_4H_9$ |
| $CH_3CO$ | $CH_3$ | n-$C_3H_7$ |
| $CH_3$ | $CH_3$ | H |
| $CH_3OCH_2$ | $CH_3$ | H |
| $(CH_3)_2CHCH_2OC_2H_4$ | $CH_3$ | H |
| $C_4H_9OCHCH_2$ (with $C_2H_5$ branch) | n-$C_3H_7$ | H |

TABLE F-continued

Intermediates $$\text{YO}-\text{C}_6\text{H}_3(\text{SR})-\text{CO}-\text{CH}_2-\text{R}_1$$

3-(Lower alkylthio)phenyl ketones of Formula IX

| Y | R | $R_1$ |
|---|---|---|
| $C_3H_7OC_3H_6$ | $CH_3$ | H |
| $C_6H_5SO_2$ | $CH_3$ | H |
| n-$C_4H_9$ | $CH_3$ | H |

The compounds of this invention having Formula I have been shown to have useful antihypertensive, vasodilator and β-adrenergic blocking activity and the compounds of Formulas II and III have been shown to have antihypertensive and β-adrenerg blocking activity as can be seen from the results of standard pharmacological tests carried out on representative examples as described below.

Antihypertensive activity was determined on the basis of the observed reduction in systolic blood pressure measured according to the method of H. Kersten et al., J. Lab. and Clin. Med. 32, 1090 (1947) following a single oral medication in the unanesthetized spontaneous hypertensive rat described by Okamato et al., Japan Circulation J. 27, 282 (1963).

Antihypertensive activity was also judged on the basis of sustained reduction of blood pressure observed in the unanesthetized trained renal hypertensive dog following repeated oral medication according to the procedure described by Lape et al., Arch. Int. Pharmacodyn. 160, 342 (1966).

Vasodilator activity was judged on the basis of observed reduction in perfusion pressure in the hind limb vasculature of the anesthetized dog determined according to the procedure described by Jandhyala et al., European J. Pharm. 17, 357 (1972), and also on the basis of percent reduction in perfusion pressure as measured in the isolated rabbit ear artery according to the method described by De LaLande et al., Aust. J. Exp. Biol. Med. Sci. 43, 639 (1965).

The β-adrenergic blocking activity was determined in the pentobarbitalized dog as judged by the ability of the test compound to inhibit the elevation in heart rate elicited by a 0.5 mcg./kg. i.v. injection of isoproterenol.

Acute intravenous and oral toxicity in mice was determined for the compound of Example 2G as follows: The compound was dissolved in distilled water and administered as the base at a volume of 10 ml./kg. for the i.v. $ALD_{50}$ or 10–40 ml./kg. for the p.o. $ALD_{50}$. The compound was administered in graded doses to groups of three mice each (Swiss-Webster strain males weighing 20±2 g.). Mortality occurred within 1 minute after i.v. administration and within 10 minutes after oral administration. Symptoms of acute intoxication for the fatalities included atoxia, loss of righting reflux, clonic convulsions and dyspnea followed by respiratory arrest. There were no untoward symptoms observed for up to 7 days for the survivors. The i.v. $ALD_{50}$ was 75 mg./kg. and the p.o. $ALD_{50}$ was 1500 mg./kg.

The 7-day oral $LD_{50}$ in rats was determined for two separate batches of the compound of Example 5E and was found to be 1850 and 1940 mg./kg. respectively. No changes in body weight and no gross tissue changes were observed in animals sacrificed 7 days post-medication.

The results of the above-described pharmacological tests are presented in Table G hereinbelow.

As noted hereinabove, certain of the compounds of this invention also have antiarrhythmic activity. The latter was determined in vivo and efficacy was judged on the ability of the test compound to convert to normal rhythm the arrhythmia induced by barium ion or ouabain intoxication. The test procedures were carried out as follows.

Ba++—induced arrhythmia

Adult rabbits or either sex weighing between 1.7 and 2.3 kg. were anesthetized with 30 to 35 mg./kg. Na-pentobarbital i.v. via a marginal ear vein. Monopolar ECG pin electrodes were inserted for a lead II display on a Model 5 Grass Polygraph using standard electrocardiographic procedures. A 23 ga. hypodermic needle, attached via a polyethylene catheter to a 10 cc. syringe, was inserted into the same vein as was used for anesthesia. A $BaCl_2.2H_2O$ solution in saline was then infused at a constant volume of 0.2 cc./min. from a Harvard Apparatus Model 600 infusion pump. This infusion was not stopped until termination of the experiment. In some studies barium chloride in distilled water was used without detectable differences. The standard rate of $BaCl_2.2H_2O$ infusion was established at 0.3 mg./kg./min. ($1.2 \times 10^{-6}$ M/kg./min.), and the concentration was adjusted appropriately in each case to accommodate the weight of the rabbit.

When the desired arrhythmia was established, the test compound was introduced as a water or saline solution into the marginal ear vein of the unused ear. The volume used was between 0.5 and 2.0 cc./kg. and was injected as a bolus over approximately 30 seconds. Deviations from standard vehicle, rate of injection and total volume administered were at the discretion of the operator. The standard initial dose of an unknown compound on the first rabbit was $5 \times 10^{-5}$ M/kg. In general, two to three rabbits were used to determine antiarrhythmic activity and the dose range of activity; multiple doses were administered. Once activity and dose was indicated, two additional rabbits were employed to confirm anti-arrhythmic activity against a multifocal tachycardia.

Ouabain-induced arrhythmia

Adult mongrel dogs of either sex after fasting for 16 to 2-hours, were anesthetized with 35 mg./kg. Na-pentobarbital i.v. and tied supine on an operating table. A patent airway was provided by inserting an endotracheal cannula, and the animal respired spontaneously. A femoral vein was double cannulated with one cannula for injection and the other as a site for ouabain infusion. The ipsilateral femoral artery was cannulated for blood pressure measurement. Na-pentobarbital supplements were given i.v. as needed.

Statham P23A blood pressure transducers were used to measure blood pressure, and electrocardiograms (lead II or $V_1$) were taken with monopolar pin electrodes. Both parameters were printed out on a Grass polygraph. Each dog was given 36 mcg./kg. ouabain i.v. over 1 minute (the solution contained 50 mcg./ml. ouabain in isotonic saline) followed by a constant ouabain infusion (0.6 mcg./kg./min.) starting 5 minutes later. The infusion solution was prepared so that the appropriate dose per minute was delivered in 0.5 ml.

When the predominant rhythm of the ensuing arrhythmia was a ventricular tachycardia (or sometimes nodal) an attempt was made to convert this arrhythmia with the test compound. Up to $10^{-4}$ M/kg. of test drug was delivered in a volume of 1 ml./kg. over a 5 minute infusion period. If a conversion or cardiotoxic effect was seen before $10^{-4}$ M/kg. was delivered, the dose was noted and repeated on a second dog.

The test was routinely conducted using pairs of dogs with a 15 minute difference in starting time. All ECG interval and duration measurements were made on lead II with a chart speed of 100 mm./sec. Heart rates were made on lead II with a chart speed of 100 mm./sec. Heart rates were taken from lead II QRS complexes at 25 mm./sec. Blood pressure was measured using a sensitivity of 10 mm. Hg/mm. pen deflection.

The results of the above-described tests are presented in Table H hereinbelow. The test compounds are indicated to be active (A) or inactive (I) at the dose tested expressed in M/kg.

TABLE G

| | Pharmacological Properties | | | | |
|---|---|---|---|---|---|
| | Antihypertensive Activity | | Vasodilator Activity | | Adrenergic Activity |
| Cpd. of Ex. No. | SH Rat $AHD_{40}^{(a)}$ mg./kg. P.O. | Renal Hypertensive Dog $MED_{10}^{(b)}$ mg./kg. tid. | Dog-Leg Perfusion $AED_{50}^{(c)}$ mg./kg. | Rabbit Ear Artery vasodilation$^{(d)}$ (molar conc.) | Dog β-blockade $AED_{50}^{(e)}$ mg./kg. |
| 1I | 2.0 | 1.25 | 0.25 | 53% ($6.25 \times 10^{-5}$M) | 0.04 |
| 2G | 2.0 | 0.0316 | 0.5 | 50% ($5 \times 10^{-5}$M) | 0.025 |
| 2H | 9.0 | | 0.5 | 20% ($5 \times 10^{-5}$M) | 0.025 |
| 4C | >20.0 (−33)$^{(f)}$ | | 0.5 | 10% ($1 \times 10^{-4}$M) | Ca 0.5 |
| 5D | 3.0 | 0.0316 | 0.5 | 49% | 0.125 |

TABLE G-continued

| | Pharmacological Properties | | | | |
|---|---|---|---|---|---|
| | Antihypertensive Activity | | Vasodilator Activity | | Adrenergic Activity |
| Cpd. of Ex. No. | SH Rat AHD$_{40}$[a] mg./kg. P.O. | Renal Hypertensive Dog MED$_{10}$[b] mg./kg. tid. | Dog-Leg Perfusion AED$_{50}$[c] mg./kg. | Rabbit Ear Artery vasodilation[d] (molar conc.) | Dog β-blockade AED$_{50}$[e] mg./kg. |
| 5F | 4.0 | | | 50% ($5 \times 10^{-5}$M) | <0.25 (70%) |
| 5G | 4.0 | | | 71% ($5 \times 10^{-5}$M) | |
| 5H | | | | 64% ($1 \times 10^{-4}$M) | |
| 6E | 15.0 | | >0.025 (25%)[h] | 58% ($1 \times 10^{-4}$M) | 0.25 |
| 7E | 30 | Ca .10[j] | | | >1.0 (12%) |
| 8 | 9 | | | | |
| 9D | 20.0 | | >0.025 (25%) | 61% ($5 \times 10^{-5}$M) | 0.0125 |
| 10 | >16.0 (−17) | >0.5 (8%)[g] | | 50% ($2 \times 10^{-4}$M) | >0.10 (23%) |
| 11 | >16.0 (−14) | <0.5 (14%) | | 38% ($1 \times 10^{-4}$M) | 0.25 |
| 12 | 5 | <0.5 (14%) | | 50% ($2 \times 10^{-4}$M) | 0.05 |
| 13C | 3 | <0.5 (17%) | 50% | 0.0125 ($1 \times 10^{-4}$M) | |
| 14D | 20.0 | | 0.5 | 29% ($1 \times 10^{-6}$M) | <1.0 (87%) |
| 15F | >20.0 (−25) | | | | |
| 16C | 15.0 | | 0.5 | 75% ($5 \times 10^{-5}$M) | >0.1 (38%) |
| 17C | >20.0 (−37) | | 0.5 | 50% ($5 \times 10^{-5}$M) | 0.05 |
| 18D | >20.0 (−26) | >0.125 (0) | 0.5 | 42% ($1 \times 10^{-4}$M) | <1.0 (100%) |
| 19C | 20.0 | >0.125 (0) | 0.5 | 50% ($5 \times 10^{-5}$M) | <0.025 (6%) |
| 20C | 7.0 | >0.125 (0) | 0.5 | (constrictor) | <0.1 (67%) |
| 21D | 40.0 | | | 50% ($1 \times 10^{-3}$M) | |
| 22D | >50.0 (−12) | | | | |
| 23C | 40.0 | | | | <0.025 (80%) |
| 24C | >50 (−12) | | ca. 0.50 | | |
| 25 | >50 (−12) | | | | |
| 26B | ca. 40.0 | >20 (0)[j] | | | >1.0 (18%) |
| 27C | >50 (−26)) | | | | ca. 0.10 |
| 28C | >50 (−15) | | | | |
| 29C | <20 (−54) | >40[j] | | | >1.0 (43%) |
| 30E | >50 (−3) | | | | ca. 0.50 |
| 31C | <50 (−54) | | | | <0.025 (60%) |
| 32E | >150 (−16) | | | | |
| 33C | >50 (−28) | | | | 1.0 |
| 34C | >50 (−8) | | | | >1.0 (40%) |
| 35C | >50 (−20) | | | | 0.6 |
| 36C | >150 (−28) | | | | |
| 37C | >150 (−21) | | | | |

[a]AHD$_{40}$ = single oral dose required to induce a 40 mm. average reduction in systolic blood pressure in the unanesthetized spontaneous hypertensive rat.
[b]MED$_{10}$ = minimum repeated oral daily dose required to effect a sustained lowering of blood pressure of 10% or greater in the unanesthetized trained renal hypertensive dog.
[c]AED$_{50}$ = approximate intraarterial dose required to cause a 50% reduction in perfusion pressure in the hind limb of the anesthetized dog.
[d]Vasodilation is expressed as the percentage reduction in perfusion pressure from the control level at the indicated molar dose.
[e]AED$_{50}$ = approximate intravenous dose required to cause 50% inhibition of the heart rate increase elicited by isoproterenol in the pentobarbitalized dog.
[f]Actual reduction in blood pressure (in mm. Hg) observed at the indicated dose.
[g]Actual percentage reduction in blood pressure observed at the indicated dose.
[h]Actual percentage reduction in perfusion pressure observed at the indicated dose.
[i]Actual percentage inhibition of heart rate increase above control level observed at the indicated dose.
[j]Administered once per day.

TABLE H

| | Antiarrhythmic Activity | |
|---|---|---|
| Cpd of Ex. No. | Conversion of Ouabain-induced Arrhythmia | Conversion of Ba++-induced Arrhythmia |
| 5H, I | A, $5 \times 10^{-6}$[a] | A, $1 \times 10^{-5}$ |
| 17C | A, $5 \times 10^{-6}$ | A, $2.5 \times 10^{-6}$ |

TABLE H-continued

| | Antiarrhythmic Activity | |
|---|---|---|
| Cpd of Ex. No. | Conversion of Ouabain-induced Arrhythmia | Conversion of Ba++-induced Arrhythmia |
| 18D | | A, $5 \times 10^{-6}$ |
| 19C | A, $5 \times 10^{-5}$ | A, $2.5 \times 10^{-6}$ |
| 30E | A, $1 \times 10^{-5}$ | A, $2 \times 10^{-5}$ |
| 34C | A, $2 \times 10^{-5}$ | A, $2.5 \times 10^{-6}$ |

(a) M/kg.

I claim:

1. A compound having the formula

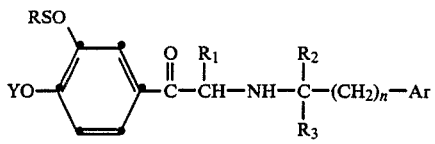

wherein:
$R_1$, $R_2$ and $R_3$ are independently hydrogen or lower alkyl;
n is an integer from 1 to 3;
Ar is phenyl, methylenedioxyphenyl or phenyl having from one to three substituents selected from the group consisting of halo, lower alkyl, hydroxy and lower alkoxy;
R is lower alkyl;
Y is hydrogen, lower alkyl, lower alkoxy-lower alkyl, lower alkanoyl, aroyl, benzenesulfonyl or toluenesulfonyl;
or an acid addition salt thereof.

2. A compound according to claim 1 wherein Y is hydrogen.

3. A compound according to claim 1 wherein Y is lower alkyl or lower-alkoxy-lower alkyl.

4. A compound according to claim 1 wherein Y is lower-alkanoyl, aroyl, benzenesulfonyl or toluenesulfonyl.

5. A compound according to claim 1 wherein:
Ar is phenyl or phenyl having from one to three substituents selected from the group consisting of halo, lower alkyl, hydroxy and lower alkoxy; and
Y is hydrogen, lower alkanoyl, aroyl, benzenesulfonyl or toluenesulfonyl.

6. A compound according to claim 5 wherein:
Ar is phenyl or phenyl having one or two substituents selected from the group consisting of lower alkyl, hydroxy and lower alkoxy.

7. A compound according to claim 6 wherein $R_1$ is hydrogen.

8. A compound according to claim 7 wherein R is methyl.

9. A compound according to claim 8 wherein Ar is phenyl.

10. A compound according to claim 8 wherein Ar is hydroxyphenyl.

11. A compound according to claim 8 wherein Ar is mono- or di-lower alkoxyphenyl.

12. A compound according to claim 8 wherein Ar is 4-methoxyphenyl.

13. 4'-Hydroxy-2-{[3-(4-methoxyphenyl)-1-methylpropyl]amino}-3'-(methylsulfinyl)acetophenone 4'-benzoate or an acid addition salt thereof according to claim 12.

14. A compound according to claim 6 wherein $R_1$ is methyl.

15. A compound according to claim 14 wherein R is methyl.

16. A compound according to claim 15 wherein Ar is lower alkoxyphenyl.

17. 4'-Hydroxy-2-{[3-(4-methoxyphenyl)-1-methylpropyl]amino}-3'-(methylsulfinyl)acetophenone or an acid addition salt thereof according to claim 12.

18. A pharmaceutical composition comprising a compound according to claim 1 in admixture with a pharmaceutically acceptable excipient.

19. The method of lowering blood pressure in a mammal which comprises administering to said mammal a blood pressure lowering effective amount of a compound according to claim 1.

* * * * *